United States Patent
Horlick et al.

(10) Patent No.: US 12,365,738 B2
(45) Date of Patent: Jul. 22, 2025

(54) METHOD OF TREATING AN INTERLEUKIN-11-ASSOCIATED OR -MEDIATED FIBROTIC DISEASE OR CONDITION BY ADMINISTERING AN ANTI-INTERLEUKIN-11 RECEPTOR SUBUNIT ALPHA (IL-11RA) ANTIBODY

(71) Applicant: Lassen Therapeutics, Inc., San Diego, CA (US)

(72) Inventors: Robert A. Horlick, San Diego, CA (US); Helen Toni Jun, San Diego, CA (US); David J. King, Encinitas, CA (US)

(73) Assignee: Lassen Therapeutics, Inc., San Diego, CA (US)

(*) Notice: Subject to any disclaimer, the term of this patent is extended or adjusted under 35 U.S.C. 154(b) by 0 days.

(21) Appl. No.: 18/896,799

(22) Filed: Sep. 25, 2024

(65) Prior Publication Data

US 2025/0011444 A1 Jan. 9, 2025

Related U.S. Application Data

(60) Division of application No. 18/590,853, filed on Feb. 28, 2024, now Pat. No. 12,129,303, which is a continuation of application No. PCT/US2022/075680, filed on Aug. 30, 2022.

(60) Provisional application No. 63/334,923, filed on Apr. 26, 2022, provisional application No. 63/238,443, filed on Aug. 30, 2021.

(51) Int. Cl.
*C07K 16/28* (2006.01)
*A61P 11/00* (2006.01)
*A61P 43/00* (2006.01)

(52) U.S. Cl.
CPC .......... *C07K 16/2866* (2013.01); *A61P 11/00* (2018.01); *A61P 43/00* (2018.01); *C07K 2317/24* (2013.01); *C07K 2317/52* (2013.01); *C07K 2317/565* (2013.01); *C07K 2317/71* (2013.01); *C07K 2317/76* (2013.01); *C07K 2317/92* (2013.01)

(58) Field of Classification Search
CPC ............ C07K 16/2866; C07K 2317/24; C07K 2317/52; C07K 2317/565; C07K 2317/71; C07K 2317/76; C07K 2317/92; C07K 2317/41; C07K 2317/75; C07K 2317/732; C07K 2317/734; A61P 11/00; A61P 43/00; A61P 35/00; A61P 37/02; A61K 2039/505
See application file for complete search history.

(56) References Cited

U.S. PATENT DOCUMENTS

| | | |
|---|---|---|
| 4,946,778 A | 8/1990 | Ladner et al. |
| 5,091,513 A | 2/1992 | Huston et al. |
| 5,132,405 A | 7/1992 | Huston et al. |
| 5,464,758 A | 11/1995 | Gossen et al. |
| 5,624,821 A | 4/1997 | Winter et al. |
| 5,814,618 A | 9/1998 | Bujard et al. |
| 6,210,922 B1 | 4/2001 | Côté et al. |
| 6,376,190 B1 | 4/2002 | Gold et al. |
| 6,387,620 B1 | 5/2002 | Smith et al. |
| 6,596,541 B2 | 7/2003 | Murphy et al. |
| 6,765,087 B1 | 7/2004 | Casterman et al. |
| 6,838,254 B1 | 1/2005 | Hamers et al. |
| 7,029,872 B2 | 4/2006 | Gerngross |
| 7,030,226 B2 | 4/2006 | Sun et al. |
| 7,112,715 B2 | 9/2006 | Chambon et al. |
| 7,166,697 B1 | 1/2007 | Galanis et al. |
| 7,217,797 B2 | 5/2007 | Hinton et al. |
| 7,244,592 B2 | 7/2007 | Hoogenboom et al. |
| 7,326,681 B2 | 2/2008 | Gerngross |
| 7,425,619 B2 | 9/2008 | Koenig et al. |
| 7,462,697 B2 | 12/2008 | Couto et al. |
| 7,629,163 B2 | 12/2009 | Gerngross |
| 7,662,925 B2 | 2/2010 | Lazar et al. |
| 7,700,321 B2 | 4/2010 | McPherson et al. |
| 7,732,570 B2 | 6/2010 | Hinton et al. |
| 8,182,814 B2 | 5/2012 | Baca et al. |
| 8,518,888 B2 | 8/2013 | Jenkins et al. |
| 9,340,618 B2 | 5/2016 | Edwards et al. |
| 9,796,782 B2 | 10/2017 | Edwards et al. |
| 12,129,303 B2 | 10/2024 | Horlick et al. |
| 2003/0108532 A1 | 6/2003 | Benson et al. |
| 2003/0118592 A1 | 6/2003 | Ledbetter et al. |
| 2003/0190311 A1 | 10/2003 | Dall'Acqua et al. |

(Continued)

FOREIGN PATENT DOCUMENTS

| | | |
|---|---|---|
| WO | WO-9311161 A1 | 6/1993 |
| WO | WO-9413804 A1 | 6/1994 |

(Continued)

OTHER PUBLICATIONS

Paul, WE (1993) Fundamental Immunology, 3rd ed. Raven Press, NY, Chap. 9, pp. 292-295.*

(Continued)

*Primary Examiner* — Robert S Landsman

(74) *Attorney, Agent, or Firm* — COOLEY LLP

(57) ABSTRACT

Provided are antibodies and antigen binding fragments thereof that bind to human interleukin-11 receptor subunit α (IL-11Rα) and related compositions, which may be used in any of a variety of therapeutic or diagnostic methods, including the treatment or diagnosis of cancers, inflammatory diseases, autoimmune diseases, and others.

16 Claims, 7 Drawing Sheets

Specification includes a Sequence Listing.

(56) References Cited

U.S. PATENT DOCUMENTS

| | | |
|---|---|---|
| 2004/0175756 A1 | 9/2004 | Kolkman et al. |
| 2005/0037421 A1 | 2/2005 | Honda et al. |
| 2005/0048512 A1 | 3/2005 | Kolkman et al. |
| 2005/0053973 A1 | 3/2005 | Kolkman et al. |
| 2005/0089932 A1 | 4/2005 | Kolkman et al. |
| 2005/0221384 A1 | 10/2005 | Kolkman et al. |
| 2006/0058510 A1 | 3/2006 | Skerra et al. |
| 2006/0173170 A1 | 8/2006 | Chamberlain et al. |
| 2007/0082365 A1 | 4/2007 | Lipovsek et al. |
| 2007/0092521 A1 | 4/2007 | McPherson et al. |
| 2007/0111281 A1 | 5/2007 | Sondermann et al. |
| 2007/0148170 A1 | 6/2007 | Desjarlais et al. |
| 2008/0139791 A1 | 6/2008 | Lipovsek et al. |
| 2008/0206246 A1 | 8/2008 | Ravetch et al. |
| 2008/0220049 A1 | 9/2008 | Chen et al. |
| 2009/0010921 A1 | 1/2009 | Umana et al. |
| 2009/0017023 A1 | 1/2009 | Koenig et al. |
| 2009/0082274 A1 | 3/2009 | Stumpp et al. |
| 2009/0163699 A1 | 6/2009 | Chamberlain et al. |
| 2009/0202533 A1 | 8/2009 | Baca et al. |
| 2009/0226421 A1 | 9/2009 | Parren et al. |
| 2010/0080794 A1 | 4/2010 | Tsuji et al. |
| 2010/0092997 A1 | 4/2010 | Nakamura et al. |
| 2010/0093976 A1 | 4/2010 | Azuma et al. |
| 2010/0143254 A1 | 6/2010 | Dall'Acqua et al. |
| 2010/0183544 A1 | 7/2010 | Jenkins et al. |
| 2010/0203046 A1 | 8/2010 | Van Vlijmen et al. |
| 2010/0209424 A1 | 8/2010 | Roopenian et al. |
| 2010/0249382 A1 | 9/2010 | Desjarlais et al. |
| 2010/0255013 A1 | 10/2010 | Presta |
| 2013/0245104 A1 | 9/2013 | De Fougerolles et al. |
| 2014/0147454 A1 | 5/2014 | Chakraborty et al. |
| 2014/0219919 A1 | 8/2014 | Edwards et al. |
| 2014/0243399 A1 | 8/2014 | Schrum et al. |
| 2015/0111248 A1 | 4/2015 | Bancel et al. |
| 2024/0199753 A1 | 6/2024 | Horlick et al. |
| 2024/0425606 A1 | 12/2024 | Horlick et al. |

FOREIGN PATENT DOCUMENTS

| | | |
|---|---|---|
| WO | WO-9701353 A1 | 1/1997 |
| WO | WO-9836061 A2 | 8/1998 |
| WO | WO-0042072 A2 | 7/2000 |
| WO | WO-0078336 A1 | 12/2000 |
| WO | WO-0220565 A2 | 3/2002 |
| WO | WO-03099322 A2 | 12/2003 |
| WO | WO-2004016750 A2 | 2/2004 |
| WO | WO-2005014643 A2 | 2/2005 |
| WO | WO-2005047337 A1 | 5/2005 |
| WO | WO-2006079372 A1 | 8/2006 |
| WO | WO-2008007648 A1 | 1/2008 |
| WO | WO-2009052588 A1 | 4/2009 |
| WO | WO-2014121325 A1 | 8/2014 |
| WO | WO-2017103108 A1 | 6/2017 |
| WO | WO-2017172981 A2 | 10/2017 |
| WO | WO-2018109170 A2 | 6/2018 |
| WO | WO-2018109174 A2 | 6/2018 |
| WO | WO-2019238882 A1 | 12/2019 |
| WO | WO-2022180145 A2 | 9/2022 |
| WO | WO-2022180172 A1 | 9/2022 |
| WO | WO-2023034809 A1 | 3/2023 |
| WO | WO-2024148240 A1 | 7/2024 |

OTHER PUBLICATIONS

Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi. 1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*
Aalberse, R.C. et al. (2002). "IgG4 breaking the rules," Immunology 105:9-19.
Alileche A., et al., "IL-2 production by myofibroblasts from post-radiation fibrosis in breast cancer patients," International Immunology, 66(10):1585-1591 (1994).
Allen, D., et al.; "Validation of peptide mapping for protein identity and genetic stability. Biologics and biotechnology section, pharmaceutical research and manufacturers of America," Biologicals.; 24(3):255-574 (1996).
Altschul, S. F., et al., "Gapped BLAST and PSI-BLAST: a new generation of protein database search programs", Nucleic Acids Research (1997); 25(17):3389-3402.
Anicetti, et al., Purity analysis of protein pharmaceuticals produced by recombinant DNA technology, Trends in Biotechnology, Dec. 1989, 7(12); pp. 342-349.
Author Unknown, "What You Need to Know About Pulmonary Fibrosis and Asthma: What is Pulmonary Fibrosis?" PulmonaryFibrosisNow.org., URL: https://pulmonaryfibrosisnow.org/2018/09/16/can-asthma-cause-pulmonary-fibrosis/ [retrieved online Feb. 18, 2020], 5 pages.
Barton, V.A., et al.; "Identification of three distinct receptor binding sites of murine interleukin-11," J Biol Chem., (1999); 274(9):5755-5761.
Bedinger et al., "Development and characterization of human monoclonal antibodies that neutralize multiple TGFβ isoforms," MABS, 8(2):389-404 (2016).
Bird et al., Single-chain antigen-binding proteins. Science; 242(4877):423-426 (1988).
Bitter et al. Expression and secretion vectors for yeast. Methods Enzymol 153:516-544 (1987).
Blanc, C., et al.; "Monoclonal antibodies against the human interleukin-11 receptor alpha-chain (IL-11Ralpha) and their use in studies of human mononuclear cells," J Immunol Methods., (2000); 241(1-2):43-59.
Boerma M, et al., "Local Administration of Interleukin-11 Ameliorates Intestinal Radiation Injury in Rats," Cancer Res, 67(19):9501-9506 (2007).
Bowers et al., Humanization of antibodies using heavy chain complementarity-determining region 3 grafting coupled with in vitro somatic hypermutation. J Biol Chem., 288(11):7688-7696 (2013).
Bozza, Mary et al., "Interleukin-11 Reduces T-Cell-Dependent Experimental Liver Injury in Mice," Hepatoloav, 30(6):1441-1447 (1999).
BPS Bioscience: One-StepTM Luciferase Assay System; Catalog No. 60690-1, Data Sheet, 4 pages (2024).
Brinkman et al., The making of bispecific antibodies, Mabs; 9(2):182-212 (2017).
Broglie, et al., Light-regulated expression of a pea ribulose-1,5-bisphosphate carboxylase small subunit gene in transformed plant cells, Science, May 1984, 224(4651); pp. 838-843.
Bruner et al.: Size exclusion HPLC method for the determination of acidic fibroblast growth factor in viscous formulations. Journal of Pharmaceutical and Biomedical Analysis; 15(12):1929-1935 (1997).
Cardo-Vila, M., et al.; "A ligand peptide motif selected from a cancer patient is a receptor-interacting site within human interleukin-11," PLoS One (2008); 3(10):e3452, 11 pages.
Carr et al., "Asthma heterogeneity and severity," World Allergy Organ J.; 9(1):41, 8 pages (2016).
Carter et al., "Humanization of an anti-p185HER2 antibody for human cancer therapy," Proceedings of the National Academy of Sciences, May 1992, 89(10), pp. 4285-4289.
Case No. PGR2019-00053 Petition for Post Grant Review *Lassen Therapeutics 1, Inc.* (Petitioner) v. *Singapore Health Services PTE Ltd.*, and National University of Singapore (Patent Owner), U.S. Pat. No. 10,106,603, filed Jul. 23, 2019, 73 pages.

(56) References Cited

OTHER PUBLICATIONS

Chao et al., "Isolating and engineering human antibodies using yeast surface display," Nature Protocols, Aug. 2006, 1(2), pp. 755-768.
Chen, Q. et al., "IL-11 Receptor alpha in the Pathogenesis of IL-13 Induced Inflammation and Remodeling," J. Immunol, 2005 174(4):2305-2313.
Chiaramonte M.G., et al., "An IL-13 inhibitor blocks the development of hepatic fibrosis during a T-helper type 2-dominated inflammatory response," The Journal of Clinical Investigation 1999; 104(6):777-785.
ClinicalTrials.gov NCT05331300: A Study to Evaluate the Safety and Pharmacokinetic Properties of LASN01 in Healthy Subjects and in Patients With Pulmonary Fibrosis or Thyroid Eye Disease. Apr. 14, 2022 (v1), 8 pages.
ClinicalTrials.gov NCT05331300: A Study to Evaluate the Safety and Pharmacokinetic Properties of LASN01 in Healthy Subjects and in Patients With Pulmonary Fibrosis or Thyroid Eye Disease. Aug. 24, 2022 (v3), 8 pages.
Clynes R., et al., "Fc Receptors are Required in Passive and Active Immunity to Melanoma," Proceedings of the National Academy of Sciences of the United States of America, Jan. 20, 1998, vol. 95, No. 2, pp. 652-656.
Co, M. S., et al., "Humanized antibodies for antiviral therapy," Proceedings of the National Academy of Sciences (1991) 88(7):2869-2873.
Colbere-Garapin, F., et al.; "A new dominant hybrid selective marker for higher eukaryotic cells," Journal of Molecular biology, Jul. 1981, 150(1):1-14.
Cook et al., "Hiding in Plain Sight: Interleukin-11 Emerges as a Master Regulator of Fibrosis, Tissue Integrity, and Stromal Inflammation," Annu Rev Med. (2020), 71:263-276.
Coruzzi, G., et al.; "Tissue-specific and light-regulated expression of a pea nuclear gene encoding the small subunit of ribulose-1,5-bisphosphate carboxylase," EMBO J. (1984); 3(8):1671-1679.
Creative Biolabs, MHH-551 "Recombinant Human Anti-human IL11 Antibody," Product Information [retrieved online May 1, 2024] from URL: https://www.creativebiolabs.net/pdf/MHH-551.pdf, 2 pages.
Curtis, D.J., et al., "Recombinant soluble interleukin-11 (IL-11) receptor alpha-chain can act as an IL-11 antagonist," Blood 1997; 90(11):4403-4412.
Czupryn, M., et al.; "Alanine-scanning mutagenesis of human interleukin-11: identification of regions important for biological activity," Ann N Y Acad Sci., (1995); 762:152-164.
Czupryn, M.J., et al.; "Structure-function relationships in human interleukin-11. Identification of regions involved in activity by chemical modification and site-directed mutagenesis," J Biol Chem., (1995); 270(2):978-985.
Dams-Kozlowska et al., A designer hyper interleukin 11 (H11) is a biologically active cytokine. BMC Biotechnol.; 12:8, 11 pages (2012).
Davies J., et al., "Expression of GnTIII in a Recombinant Anti-CD20 CHO Production Cell Line: Expression of Antibodies with Altered Glycoforms Leads to an Increase in ADCC Through Higher Affinity for FCgammaRIII," Biotechnology Bioengineering, Aug. 20, 2001, vol. 74, No. 04, pp. 288-294.
Declaration by Dr. Sebastian Schaefer filed in EP Application No. 16822941 Opposition dated Aug. 23, 2019, 1 page.
Declaration by Prof. Scott L Friedman filed in EP Application No. 16822941 Opposition dated Apr. 30, 2020, 79 pages.
Declaration No. 1 of Stuart Cook filed in EP Application No. 16822941 Opposition dated May 1, 2020, 25 pages.
Declaration No. 2 by Stuart Cook filed in EP Application No. 16822941 Opposition dated Mar. 8, 2021, 20 pages.
DeNardo et al., Comparison of 1,4,7,10-tetraazacyclododecane-N,N',N",N"'-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts. Clin Cancer Res.; 4(10):2483-2490 (1998).
Du et al., "A Bone Marrow Stromal-Derived Growth Factor, Interleukin-11, Stimulates Recovery of Small Intestinal Mucosal Cells After Cytoablative Therapy," Blood, 83(1):33-37 (1994).
Ehrlich, P. et al., "Isolation of an active heavy-chain variable domain from a homogeneous rabbit antibody by cathepsin B digestion of the aminoethylated heavy chain," Biochemistry, Aug. 1, 1980, vol. 19, No. 17, pp. 4091-4096.
Ellington et al., "In vitro selection of RNA molecules that bind specific ligands," Nature; 346(6287):818-822 (1990).
Engelhard, et al., The insect tracheal system: a conduit for the systemic spread of Autographa californica M nuclear polyhedrosis virus, Proceedings of the National Academy of Sciences, Apr. 1994, 91(8); pp. 3224-3227.
EP Application No. 16822941.7 Annex 1 of the Response to the response of the patentee Singapore Health Services Pte Ltd and National University of Singapore, dated Sep. 24, 2019, 2 pages.
EP Application No. 16822941.7 Consolidated List of Cited Opposition documents filed Oct. 6, 2021, 4 pages.
EP Application No. 16822941.7 Information of Relevance of Third Party Observation filed May 8, 2018, dated May 11, 2018, 3 pages.
EP Application No. 16822941.7 Observations on the Opponent's submission filed Sep. 15, 2023, dated Dec. 4, 2023, 9 pages.
EP Application No. 16822941.7 Opponent's Letter dealing with oral proceedings during the appeal procedure filed Apr. 30, 2024, 8 pages.
EP Application No. 16822941.7 Third Party Observation filed May 8, 2018, 3 pages.
Expert Panel Report 3: Guidelines for the Diagnosis and Management of Asthma. Bethesda (MD): National Heart, Lung, and Blood Institute (US); Aug. 2007. Section 2, Definition, Pathophysiology and Pathogenesis of Asthma, and Natural History of Asthma. Available from: URL: https://www.ncbi.nlm.nih.gov/books/NBK7223/, 24 pages.
Extended European Search Report for EP Application No. 08842066.6 dated Dec. 30, 2010, 5 pages.
Extended European Search Report for EP Application No. 14749445.4 dated Sep. 9, 2016, 8 pages.
Finlay, W. J. J. et al., "Anti-PD1 'SHR-1210' aberrantly targets proangiogenic receptors and this polyspecificity can be ablated by paratope refinement," mAbs, 11(1):26-44 (2019).
Forth, W., "Allgemeine und spezielle Pharmakologie und Toxikologie," Urban & Fischer Verlag, Chapter 16, (2013); pp. 362-364, with English Translation, "General and special pharmacology and toxicology," 13 pages.
Friedlander, M., "Fibrosis and diseases of the eye," J. Clin. Invest. (2007), 117(3):576-586, doi:10.1172/JCI31030.
Fuhrmann-Benzakein, et al., "Inducible and irreversible control of gene expression using a single transgene," 28(23):E99, 5 pages (2000).
Gerngross, Advances in the production of human therapeutic proteins in yeasts and filamentous fungi, Nat Biotechnol., Nov. 2004, 22(11); pp. 1409-1414.
Gorman et al. "Reshaping a therapeutic CD4 antibody." Proceedings of the National Academy of Sciences (1991); 88.10: 4181-4185.
Graham, T.L. et al. (1977). "Characteristics of a Human Cell Line Transformed by DNA From Human Adenovirus Type 5," J. Gen. Virol., vol. 36, pp. 59-72.
Ham et al., "Critical role of interleukin-11 in isoflurane-mediated protection against ischemic acute kidney injury in mice," Anesthesiology, 119(6):1389-1401 (2013).
Hamilton, et al., Humanization of yeast to produce complex terminally sialylated glycoproteins, Science, Sep. 2006, 313(5792); pp. 1441-1443.
Hamilton et al., Production of complex human glycoproteins in yeast. Science; 301(5637):1244-1246 (2003).
Hartman, et al., Two Dominant-Acting Selectable Markers for Gene Transfer Studies in Mammalian Cells, Proceedings of the National Academy of Sciences of the United States of America, Nov. 1988, 85(21); pp. 8047-8051.
Hennersdorf, M. G., et al.; "Das Herz bei arterieller Hypertonie," Der Internist., (2007); 3(48):236-245, with English Translation, "The heart in hypertension," 22 pages.

(56) References Cited

OTHER PUBLICATIONS

Hermann et al., "Important immunoregulatory role of interleukin-11 in the inflammatory process in rheumatoid arthritis," Arthritis Rheum, 1998, 41(8):1388-1397.

Hess et al., Prevalidation of the ex-vivo model PCLS for prediction of respiratory toxicity. Toxicol In Vitro.; 32:347-361 (2016).

Hochman, J. et al., "Folding and interaction of subunits at the antibody combining site," Biochemistry, Jun. 1, 1976, vol. 15, No. 12, pp. 2706-2710.

Holgate, S.T, et al., The mechanisms, diagnosis, and management of severe asthma in adults, Polosa R, Lancet 2006; 368:780-793.

Holliger, P., et al., ""Diabodies": small bivalent and bispecific antibody fragments", Proceedings of the National Academy of Sciences (1993); 90(14): 6444-6448.

Holliger, P., et al., "Engineering bispecific antibodies", Current Opinion in Biotechnology (1993); 4(4):446-449.

Hu, S., et al., "Minibody: a novel engineered anti-carcinoembryonic antigen antibody fragment (single-chain Fv-CH3) which exhibits rapid, high-level targeting of xenografts", Cancer Research (1996); 56(13):3055-3061.

Husain, A.N.: "Chapter 15: The Lung," Pathologic Basis of Disease, Elsevier 2010, 8th Edition, ed. Robbins et al., pp. 677-737.

Huston, J. S., et al., "Protein engineering of antibody binding sites: recovery of specific activity in an anti-digoxin single-chain Fv analogue produced in *Escherichia coli*", Proceedings of the National Academy of Sciences (1988); 85(16):5879-5883.

Ill, C. et al., "Design and construction of a hybrid immunoglobulin domain with properties of both heavy and light chain variable regions," Protein Engineering, Design and Selection, Aug. 1997, vol. 10, Issue 8, pp. 949-957.

Inbar et al., "Localization of antibody-combining sites within the variable portions of heavy and light chains". Proceedings of the National Academy of Sciences. Sep. 1972; 69(9):2659-62.

Indra, A.K., et al.; "Temporally-controlled site-specific mutagenesis in the basal layer of the epidermis: comparison of the recombinase activity of the tamoxifen-inducible Cre-ER(T) and Cre-ER(T2) recombinases," Nucleic Acids Research, Nov. 1999, 27(22); pp. 4324-4327.

International Preliminary Report on Patentability for International Application No. PCT/AU2008/001587 dated Apr. 27, 2010, 5 pages.

International Preliminary Report on Patentability for International Application No. PCT/US2022/075680 dated Mar. 14, 2024, 8 pages.

International Search Report and Written Opinion for International Application No. PCT/AU2008/001587 dated Jan. 7, 2009, 5 pages.

International Search Report and Written Opinion for International Application No. PCT/AU2014/000083, dated Jun. 13, 2014, 10 pages.

International Search Report and Written Opinion for International Application No. PCT/EP2017/083051 dated Aug. 13, 2018, 23 pages.

International Search Report and Written Opinion for International Application No. PCT/US2022/075680 dated Feb. 6, 2023, 14 Pages.

Invitation to Pay Fee for International Application No. PCT/US2022/075680 dated Nov. 21, 2022, 3 pages.

Johnstone, N. C., et al., "Emerging roles for IL-11 signaling in cancer development and progression: Focus on breast cancer," Cytokine & Growth Factor Reviews, 26(5):489-498 (2015).

Kapina, M.A., et al.; "Interleukin-11 drives early lung inflammation during *Mycobacterium tuberculosis* infection in genetically susceptible mice," PLoS One (2011); 6(7):e21878, 7 pages.

Karpovich et al., "Expression and function of interleukin-11 and its receptor alpha in the human endometrium," Molecular Human Reproduction; 9(2):75-80 (2003).

Keith et al., "IL-11, a pleiotropic cytokine: exciting new effects of IL-11 on gastrointestinal mucosal biology," Stem Cells, 12(Suppl 1):79-90 (1994).

Kelly et al., "How to study proteins by circular dichroism," Biochim Biophys Acta; 1751(2):119-139 (2005).

Kettleborough et al., "Humanization of a mouse monoclonal antibody by CDR-grafting: the importance of framework residues on loop conformation." Protein Engineering (1991); 4.7:773-783.

Kiessling, S., et al.; "Functional expression of the interleukin-11 receptor alpha-chain and evidence of antiapoptotic effects in human colonic epithelial cell," J Biol Chem., (2004); 279(11):10304-10315.

Kimura et al., Interleukin-11 (IL-11) enhances clonal proliferation of acute myelogenous leukemia cells with strong expression of the IL-11 receptor alpha chain and signal transducing gp130. Leukemia; 13(7):1018-1027 (1999).

Kimura, Ryusuke et al., "Identification of cardiac myocytes as the target of interleukin 11, a cardioprotective cytokine" Cytokine, 38(2):107-115 (2007).

King, K.R.: "A scary movie, starring IL-11," Science Translational Medicine (2017), 9(418): eaar2443, 3 pages.

Kohler et al., Derivation of specific antibody-producing tissue culture and tumor lines by cell fusion. Eur. J. Immunol. ;6(7):511-519 (1976).

Kormann, et al., Expression of therapeutic proteins after delivery of chemically modified mRNA in mice. Nat Biotechnol.; 29(2):154-157 (2011).

Kramer et al., "Transgene control engineering in mammalian cells," Methods Mol. Biol., 308:123-143 (2005).

Kwon, K., et al.; "High quality protein microarray using in situ protein purification," BMC Biotechnol., Aug. 2009, 9:72; 10 pages.

Lawitz et al., "A pilot study of interleukin-11 in subjects with chronic hepatitis C and advanced liver disease nonresponsive to antiviral therapy," American Journal of Gastroenterology (2004), 99:(12):2359-2364.

Lee, C. G. et al., "Endogenous IL-11 signaling is essential in Th2- and IL-13-induced inflammation and mucus production," Am J Respir Cell Mol Biol., (2008), 39(6):739-746.

Lemoli, R.M., et al.; "Interleukin-11 (IL-11) acts as a synergistic factor for the proliferation of human myeloid leukaemic cells," Br J Haematol. (1995); 91(2):319-326.

Lentsch et al., "Regulatory effects of interleukin-11 during acute lung inflammatory injury," J Leukoc Biol., (1999), 66(1):151-157.

Li, et al., Optimization of humanized IgGs in glycoengineered Pichia pastoris, Nature Biotechnology, Feb. 2006, 24(2); pp. 210-215.

Lin, et al., Automated 96-well purification of hexahistidine-tagged recombinant proteins on MagneHis Ni(2)+-particles, Methods Mol Biol., 2009, 498; pp. 129-141.

Lindahl et al., "Microarray profiling reveals suppressed interferon stimulated gene program in fibroblasts from scleroderma-associated interstitial lung disease," Respiratory Research 2013, 14(1):80, 14 pages.

Lobuglio et al., "Mouse/human chimeric monoclonal antibody in man: kinetics and immune response." Proceedings of the National Academy of Sciences (1989); 86.11:4220-4224.

Logan, et al., Adenovirus tripartite leader sequence enhances translation of mRNAs late after infection, Proc. Natl. Acad. Sci. U.S.A., 1984, 81(12); pp. 3655-3659.

Lonberg and Huszar, "Human Antibodies from Transgenic Mice," International Reviews of Immunology, Jan. 1995, 13(1), pp. 65-93.

Lowy I., et al., "Isolation of Transforming Dna: Cloning The Hamster Aprt Gene," Cell, Dec. 1980, vol. 22 (3), pp. 817-823.

Maddox, et al., Elevated serum levels in human pregnancy of a molecule immunochemically similar to eosinophil granule major basic protein, J Exp Med., Oct. 1983, 158(4); pp. 1211-1226.

Maeda et al. "Construction of reshaped human antibodies with HIV-neutralizing activity." Human Antibodies (1991); 2(3):124-134.

Maeshima, Kyoichiro, "A Protective Role of Interleukin 11 on Hepatic Injury in Acute Endotoxemia" Shock, 2004, 21(2):134-8.

Marra F., et al., "Mononuclear cells in liver fibrosis," Semin Immunopathol, 2009; 31(3):345-358.

Martin, F. et al., "The affinity-selection of a minibody polypeptide inhibitor of human interleukin-6," EMBO Journal, Nov. 15, 1994, 13(22):5303-5309.

(56) References Cited

OTHER PUBLICATIONS

Mather, et al., Culture of testicular cells in hormone-supplemented serum-free medium, Annals of the New York Academy of Sciences, Jun. 1982, 383; pp. 44-68.
Mather, J.P. (1980). "Establishment and Characterization of Two Distinct Mouse Testicular Epithelial Cell Lines," Biol. Reprod., vol. 23, pp. 243-251.
Maxwell, et al., A simple in vivo assay for increased protein solubility, Protein Sci., Sep. 1999, 8(9); pp. 1908-1911.
McCoy et al., "IL-11 produced by breast cancer cells augments osteoclastogenesis by sustaining the pool of osteoclast progenitor cells," BMC Cancer (2013); 13:16, 11 pages.
Meagher, et al., Deconvolution of the fluorescence emission spectrum of human antithrombin and identification of the tryptophan residues that are responsive to heparin binding, J Biol Chem., 273(36):23283-23289 (1998).
Mims J.W., et al., "Asthma: definitions and pathophysiology," Int Forum Allergy Rhinol., 2015; 5(Suppl 1):S2-S6.
Murphy and Piwnica-Worms, Overview of the Baculovirus Expression System, Current protocols in protein science, 2001, Chapter 5, Unit 5.4, 4 pages.
Muyldermans, S. et al., "Sequence and structure of VH domain from naturally occurring camel heavy chain immunoglobulins lacking light chains," Protein Eng. 7(9):1129-1135 (1994).
Nagamine, et al., Electrochemical screening of recombinant protein solubility in *Escherichia coli* using scanning electrochemical microscopy (SECM), Biotechnol Bioeng., Apr. 2007, 96(5); pp. 1008-1013.
Neuberger, M., "Generating high-avidity human Mabs in mice," Nature Biotechnology, Jul. 1996, 14(7), pp. 826 (1page).
Ng, Benjamin et al., "Interleukin-11 is a therapeutic target in idiopathic pulmonary fibrosis," BioRxiv pre-print; Sci Transl Med.; 11(511):eaaw1237, 31 pages (2018).
Ng, Benjamin et al., "Interleukin-11 is a therapeutic target in idiopathic pulmonary fibrosis," Sci Transl Med.; 11(511):eaaw1237, 14 pages (2019).
Nishina, Takashi, "Interleukin-11 links oxidative stress and compensatory proliferation," Science Signaling, 2012, 5(207):ra5, 12 pages.
No, et al., Ecdysone-inducible gene expression in mammalian cells and transgenic mice, Proceedings of the National Academy of Sciences, Apr. 1996, 93(8); pp. 3346-3351.
Obana et al., "Therapeutic activation of signal transducer and activator of transcription 3 by interleukin-11 ameliorates cardiac fibrosis after myocardial infarction," Circulation, 121(5):684-691 (2010), with Supplemental Material and Methods [14 pages]; 22 pages total.
Obana, Masanori, "Therapeutic administration of IL-11 exhibits the postconditioning effects against ischemia-reperfusion injury via STAT3 in the heart" Physiol Heart Circ., 2012, 303(5):H569-77.
Opposition document filed in EP16822941; patentee Singapore Health Services Pte Ltd and National University of Singapore, dated Sep. 24, 2019, "Neutralizing Interleukin-11 Antibodies Reduce Pressure Overload Induced Cardiac Fibrosis In Mice," 4 pages.
Park et al., "Monoclonal antibody therapy," Advances in Protein Chemistry (2001), 56:369-421.
Peterson, et al., Enzymatic cleavage of peptide-linked radiolabels from immunoconjugates, Bioconjug Chem.; 10(4):553-537 (1999).
Presta, L. G. et al., "Engineering therapeutic antibodies for improved function," Biochemical Society Transactions (2002) 30(4):487-490.
Putoczki, T.L., et al.; "Interleukin-11 is the dominant IL-6 family cytokine during gastrointestinal tumorigenesis and can be targeted therapeutically," Cancer Cell. (2013); 24(2):257-271.
Qing, et al., Cold-shock induced high-yield protein production in *Escherichia coli*, Nat Biotechnol., Jul. 2004, 22(7):877-882.
Queen C. et al. (Dec. 1989), "A Humanized Antibody That Binds To The Interleukin 2 Receptor," Proceedings of the National Academy of Sciences, vol. 86, No. 24, pp. 10029-10033.
R&D Systems: Human IL-11 Antibody; Monoclonal Mouse IgG2A Clone# 22626; Catalog No. MAB218, 1 page (2018).

R&D Systems: Human IL-11Ra Antibody; Monoclonal Mouse IgG1 Clone# 473143; Catalog No. MAB1977, 1 page (2018).
Ray et al., "Regulated overexpression of interleukin 11 in the lung. Use to dissociate development-dependent and -independent phenotypes," J Clin Invest., 1997, 100(10):2501-2511.
Redlich et al., "IL-11 enhances survival and decreases TNF production after radiation-induced thoracic injury," J Immunol., 1996, 157(4):1705-1710.
Reiter, Y., et al., "Engineering antibody Fv fragments for cancer detection and therapy: Disulfide-stabilized Fv fragments," Nature Biotechnology (Oct. 1996); 14(10):1239-1245.
Rhodes, et al., Transformation of maize by electroporation of embryos, Methods Mol Biol., 1995, 55; pp. 121-131.
Richter M & Jacobsen B, "Subcutaneous absorption of biotherapeutics: knowns and unknowns", Drug Metabolism and Disposition (2014), 42:1881-1889.
Ridgway, J. B. B., et al., "'Knobs-into-holes' engineering of antibody CH3 domains for heavy chain heterodimerization", Protein Engineering, Design and Selection (1996); 9(7):617-621.
Riechmann, L., et al., "Reshaping human antibodies for therapy", Nature (1988); 332(6162):323-327.
Rosser, et al., Transient transfection of CHO-K1-S using serum-free medium in suspension: a rapid mammalian protein expression system, Protein Expr Purif., Apr. 2005, 40(2); pp. 237-243.
Sarosiek S., et al., "Review of siltuximab in the treatment of multicentric Castleman's disease," Ther Adv Hematol (2016), 7(6):360-366.
Sato et al. "Reshaping a human antibody to inhibit the interleukin 6-dependent tumor cell growth." Cancer Research (1993); 53.4:851-856.
Schaefer et al., "IL-11 is a crucial determinant of cardiovascular fibrosis," Nature 2017, 552(7683):110-115.
Scharf et al., "Heat stress promoters and transcription factors," Results Probl Cell Differ., 1994, 20:125-162.
Schwertschlag et al., "Hematopoietic, immunomodulatory and epithelial effects of interleukin-11," Leukemia (1999) 13(9):1307-1315.
Serabian, M.A., et al., "PLA # 96-1433," Neumega; Genetics Institute, Inc., Pharmacologists Review 1997; pp. 1-56.
Sheridan et al., "Interleukin-11 attenuates pulmonary inflammation and vasomotor dysfunction in endotoxin-induced lung injury," American Physiological Society (1999), 277(5):L861-L867.
Shields, et al., "Lack of Fucose on Human IgG1 N-Linked Oligosaccharide Improves Binding to Human FcγRIII and Antibody-dependent Cellular Toxicity." The Journal of Biological Chemistry (2002); 277(30):26733-26740.
Shields, R. L., et al., "High resolution mapping of the binding site on human IgG1 for FcγRI, FcγRII, FcγRIII, and FcRn and design of IgG1 variants with improved binding to the FcγR", Journal of Biological Chemistry (2001); 276(9):6591-6604.
Shimp, et al., Production and characterization of clinical grade *Escherichia coli* derived Plasmodium falciparum 42 kDa merozoite surface protein 1 (MSP1(42)) in the absence of an affinity tag, Protein Expr Purif., Nov. 2006, 50(1); pp. 58-67.
Shinkawa T., et al., "The Absence of Fucose but Not the Presence of Galactose or Bisecting N-Acetylglucosamine of Human IgG1 Complex-type Oligosaccharades Shows the Critical Role of Enhancing Antibody-dependent Cellular Cytotoxicity," The Journal of Biological Chemistry, Jan. 31, 2003, vol. 278, No. 5, pp. 3466-3473.
Silverman J., et al., "Multivalent Avimer Proteins Evolved by Exon Shuffling of a Family of Human Receptor Domains," Nature Biotechnology, Nature Publishing Group, Dec. 2005, vol. 23, No. 12, pp. 1556-1561.
Sitaraman, et al., High-throughput protein expression using cell-free system, Methods Mol Biol. 2009, 498; pp. 229-244.
Skerra, A. "Alternative binding proteins: anticalins—harnessing the structural plasticity of the lipocalin ligand pocket to engineer novel binding activities", FEBS J. (2008); 275(11):2677-2683.
Sohal S. S., et al., "Clinical significance of epithelial mesenchymal transition (EMT) in chronic obstructive pulmonary disease (COPD): potential target for prevention of airway fibrosis and lung cancer," Clinical and Translational Medicine, 2014, 3(1):33, 4 pages.

(56) References Cited

OTHER PUBLICATIONS

Sommer, J., et al.; "Constitutively active mutant gp130 receptor protein from inflammatory hepatocellular adenoma is inhibited by an anti-gp130 antibody that specifically neutralizes interleukin 11 signaling," J Biol Chem. (2012); 287(17):13743-13751.

Sopel et al., "Myocardial fibrosis in response to Angiotensin II is preceded by the recruitment of mesenchymal progenitor cells," Lab Invest, Apr. 2011; 91(4):565-78. Epub Nov. 29, 2010.

Stangou et al., "Effect of IL-11 on glomerular expression of TGF-beta and extracellular matrix in nephrotoxic nephritis in Wistar Kyoto rats," J Nephrol., 24(1):106-111 (2011).

Stenvall, et al., High-throughput solubility assay for purified recombinant protein immunogens, Biochim Biophys Acta., 1752(1):6-10 (2005).

Structural Genomics Consortium et al., "Protein Production and Purification," Nature Methods, 2008, vol. 5 No. 2, pp. 135-146.

Stumpp et al., "DARPins: a true alternative to antibodies," Curr Opin Drug Discov Devel., 10(2):153-159 (2007).

Tacken, I., et al.; "Definition of receptor binding sites on human interleukin-11 by molecular modeling-guided mutagenesis," Eur J Biochem., (1999); 265(2):645-655.

Takamatsu et al., "Expression of bacterial chloramphenicol acetyltransferase gene in tobacco plants mediated by TMV-RNA," EMBO J., (1987); 6(2):307-311.

Tan, Y., et al.; "IL11-mediated stromal cell activation may not be the master regulator of pro-fibrotic signaling downstream of TGFBeta," Frontiers in Immunology (Feb. 2024); 15:1293883, 15 pages.

Tang L.K., et al., "Airway remodelling in asthma: current understanding and implications for future therapies," Pharmacology & Therapeutics 2006; 112(2):474-488.

Tang, W., et al., "Targeted expression of IL-11 in the murine airway causes lymphocytic inflammation, bronchial remodeling, and airways obstruction," The Journal of Clinical Investigation, 1996, 98(12):2845-2853.

Tang, W. et al., "Transforming growth factor-beta stimulates interleukin-11 transcription via complex activating protein-1-dependent pathways," The Journal of Biological Chemistry, 1998, 273(10):5506-5513.

Tempest P.R., et al., "Reshaping a Human Monoclonal Antibody to Inhibit Human Respiratory Syncytial Virus Infection In Vivo." Nature Biotechnology, Mar. 1991, vol. 9 (3), pp. 266-271.

Traunecker, A. et al., "Janusin: New molecular design for bispecific reagents," Int J Cancer Suppl., Jan. 1992, vol. 7, pp. 51-52.

Traunecker et al., "Bispecific single chain molecules (Janusins) target cytotoxic lymphocytes on HIV infected cells," The EMBO Journal, Dec. 1991, 10(12), pp. 3655-3659.

Trepicchio WL. et al., "Interleukin-11 therapy selectively downregulates type I cytokine proinflammatory pathways in psoriasis lesions," J. Clin. Invest. (1999), 104(11):1527-1537.

Trepicchio, William L., et al., "Protective effect of rhIL-11 in a murine model of acetaminophen-induced hepatotoxicity," Toxicological Patholoav, 2001, 29(2):242-249.

Tuerk et al., "Systematic evolution of ligands by exponential enrichment: RNA ligands to bacteriophage T4 DNA polymerase," Science, 1990, 249(4968):505-510.

Umana P., et al., "Engineered Glycoforms of an Antineuroblastoma IgG1 With Optimized Antibody-dependent Cellular Cytotoxic Activity," Nature Biotechnology, Feb. 1999, vol. 17, No. 2, pp. 176-180.

Underhill-Day, N., et al.; "Functional characterization of W147A: a high-affinity interleukin-11 antagonist," Endocrinology (2003); 144(8):3406-3414.

Urlaub et al., "Isolation of Chinese hamster cell mutants deficient in dihydrofolate reductase activity," Proc. Natl. Acad. Sci. USA, 1980, 77(7), pp. 4216-4220.

U.S. Appl. No. 18/687,781, filed Feb. 28, 2024, by Inventors Robert A. Horlick, et al.

Van Heeke et al., "Expression of Human Asparagine Synthetase in *Escherichia coli*," The Journal of Biological Chemistry, 264(10):5503-5509 (1989).

Verhoeyen, M. et al., "Reshaping Human Antibodies: Grafting an Antilysozyme Activity," Science 239(4847):1534-1536 (1988).

Viola, M., et al., "Subcutaneous delivery of monoclonal antibodies: How do we get there?" J Control Release., 2018; 286:301-314.

Wang et al., "IL-11 selectively inhibits aeroallergen-induced pulmonary eosinophilia and Th2 cytokine production," J Immunol., 2000; 165(4):2222-2231.

Ward et al., Binding activities of a repertoire of single immunoglobulin variable domains secreted from *Escherichia coli*, Nature (1989) 341(6242):544-546.

Waxman et al., "Targeted lung expression of interleukin-11 enhances murine tolerance of 100% oxygen and diminishes hyperoxia-induced DNA fragmentation," J Clin Invest., 1998; 101(9):1970-1982.

Wei L., "Immunological aspect of cardiac remodeling: T lymphocyte subsets in inflammation-mediated cardiac fibrosis," Experimental and Molecular Pathology, 2011; 90(1):74-78.

Widjaja et al., "Inhibiting Interleukin 11 Signaling Reduces Hepatocyte Death and Liver Fibrosis, Inflammation, and Steatosis in Mouse Models of Nonalcoholic Steatohepatitis," Gastroenterology (2019); 157(3):777-792; 792e1-e14, 30 pages.

Wigler et al., "Transformation of mammalian cells with an amplifiable dominant-acting gene," Proceedings of the National Academy and Sciences, vol. 77, No. 6, Jun. 1980, pp. 3567-3570.

Wigler M., et al.; "Transfer Of Purified Herpes Virus Thymidine Kinase Gene to Cultured Mouse Cells," Cell, 11(1):223-232 (1977).

Wigley, et al., "Protein solubility and folding monitored in vivo by structural complementation of a genetic marker protein," Nature Biotechnology, 19(2):131-136 (2001).

Wildt, et al., The humanization of N-glycosylation pathways in yeast, Nat Rev Microbiol, Feb. 2005, 53(2):119-128.

Winter, et al., The expression of heat shock protein and cognate genes during plant development, Results Probl Cell Differ. 1991, 17; pp. 85-105.

Wollin L et al., "Antifibrotic and anti-inflammatory activity of the tyrosine kinase inhibitor Nintedanib in experimental models of lung fibrosis," J Pharmacol Exp Ther., 2014; 349(2):209-220.

Worn, A. et al. "Stability Engineering of Antibody Single-chain Fv Fragments," J. Mol.Biol., 2001, 305(5):989-1010.

Wyeth Pharmaceuticals Inc., Neumega (oprelvekin) RX label (US) 2009, [Available online URL: https://www.accessdata.fda.gov/drugsatfda_docs/label/2009/103694s1008lbl.pdf] 28 pages.

Wynn, T. A., et al., "Fibrotic disease and the T(H)1/T(H)2 paradigm," Nat Rev Immunol., 2004, 4(8):583-594.

Wynn, T.A., et al., "Cellular and molecular mechanisms of fibrosis," J Pathol., 2008; 214(2):199-210.

Yazaki, et al., "Expression of recombinant antibodies in mammalian cell lines," Methods Mol Biol., 248:255-268 (2004).

Yokota et al., "Quantitative in vitro bioassay for recombinant human interleukin-11," J AOAC Int., 2000; 83(5):1053-1057.

Zhang et al., "Interleukin-11 promotes the progress of gastric carcinoma via abnormally expressed versican," Int J Biol Sci., 8(3):383-393 (2012).

Zhu et al., "IL-11 Attenuates Liver Ischemia/Reperfusion Injury (IRI) through STAT3 Signaling Pathway in Mice," PLoS One., 2015; 10(5):e0126296, 15 pages.

Zhu et al. "Pulmonary expression of interleukin-13 causes inflammation, mucus hypersecretion, subepithelial fibrosis, physiologic abnormalities, and eotaxin production," J Clin Invest., 1999, 103(6):779-788.

Zimmermann, K., "A triglycine linker improves tumor uptake and biodistributions of 67-Cu-labeled anti-neuroblastoma MAb chCE7 F(ab')2 fragments," Nucl Med Biol., 1999; 26(8):943-950.

Zuckerman et al., "The characterization and functional significance of plasma membrane Fc Receptors," CRC Crit Rev Microbiol., 7(1):1-26 (1978).

\* cited by examiner

METHOD OF TREATING AN INTERLEUKIN-11-ASSOCIATED OR -MEDIATED FIBROTIC DISEASE OR CONDITION BY ADMINISTERING AN ANTI-INTERLEUKIN-11 RECEPTOR SUBUNIT ALPHA (IL-11RA) ANTIBODY

CROSS-REFERENCE TO RELATED APPLICATIONS

This application is a divisional of U.S. patent application Ser. No. 18/590,853, filed Feb. 28, 2024, now U.S. Pat. No. 12,129,303, issued Oct. 29, 2024, which is a continuation of International PCT Patent Application Serial No. PCT/US2022/075680, filed Aug. 30, 2022, which claims priority to U.S. Provisional Application No. 63/238,443, filed Aug. 30, 2021; and U.S. Provisional Application No. 63/334,923, filed Apr. 26, 2022, each of which is incorporated by reference in its entirety.

STATEMENT REGARDING SEQUENCE LISTING

The Sequence Listing XML associated with this application is provided in XML file format and is hereby incorporated by reference into the specification. The name of the XML file containing the Sequence Listing XML is LASS_005_04US_SeqList_ST26.xml. The XML file is about 329,266 bytes, was created on Sep. 25, 2024, and is being submitted electronically via USPTO Patent Center.

BACKGROUND

Technical Field

The present disclosure relates to antibodies and antigen binding fragments thereof that bind to human interleukin-11 receptor subunit α (IL-11Rα) and related compositions, which may be used in any of a variety of therapeutic or diagnostic methods, including the treatment or diagnosis of cancers, inflammatory diseases, autoimmune diseases, and others.

Description of the Related Art

Interleukin-11 (IL-11) is a member of the IL-6 family, and plays a prominent role in chronic inflammation, autoimmunity, cancer, and other diseases. It also plays a critical role in the initiation and maintenance of chronic fibrotic responses. Thus, IL-11 signaling inhibitors represent a promising therapeutic approach for treating a variety of diseases, including inflammatory diseases, autoimmune diseases, chronic fibrotic diseases, and cancers.

Exemplary IL-11 signaling inhibitors under development include antibodies that bind to the interleukin-11 receptor subunit α (IL-11Rα) (see, for example, U.S. Pat. Nos. 9,796,782; and 9,340,618). However, there is a need in the art for anti-IL-11Rα antibodies with increased potency and optimal developability characteristics.

BRIEF SUMMARY

Embodiments of the present disclosure include an isolated antibody, or an antigen binding fragment thereof, which binds to interleukin-11 receptor subunit α (IL-11Rα), wherein the at least one antibody, or antigen binding fragment thereof, comprises:

a heavy chain variable region ($V_H$) that comprises complementary determining region $V_H$CDR1, $V_H$CDR2, and $V_H$CDR3 sequences selected from Table A1 and variants thereof which specifically bind to IL-11Rα; and a light chain variable region ($V_L$) that comprises complementary determining region $V_L$CDR1, $V_L$CDR2, and $V_L$CDR3 sequences selected from Table A1 and variants thereof which specifically bind to IL-11Rα.

In some embodiments:

the $V_H$CDR1, $V_H$CDR2, and $V_H$CDR3 sequences comprise SEQ ID NOs: 1-3, respectively, and the $V_L$CDR1, $V_L$CDR2, and $V_L$CDR3 sequences comprise SEQ ID NOs: 4-6, respectively;

the $V_H$CDR1, $V_H$CDR2, and $V_H$CDR3 sequences comprise SEQ ID NOs: 7-9, respectively, and the $V_L$CDR1, $V_L$CDR2, and $V_L$CDR3 sequences comprise SEQ ID NOs: 10-12, respectively;

the $V_H$CDR1, $V_H$CDR2, and $V_H$CDR3 sequences comprise SEQ ID NOs: 13-15, respectively, and the $V_L$CDR1, $V_L$CDR2, and $V_L$CDR3 sequences comprise SEQ ID NOs: 16-18, respectively;

the $V_H$CDR1, $V_H$CDR2, and $V_H$CDR3 sequences comprise SEQ ID NOs: 19-21, respectively, and the $V_L$CDR1, $V_L$CDR2, and $V_L$CDR3 sequences comprise SEQ ID NOs: 22-24, respectively;

the $V_H$CDR1, $V_H$CDR2, and $V_H$CDR3 sequences comprise SEQ ID NOs: 25-27, respectively, and the $V_L$CDR1, $V_L$CDR2, and $V_L$CDR3 sequences comprise SEQ ID NOs: 28-30, respectively;

the $V_H$CDR1, $V_H$CDR2, and $V_H$CDR3 sequences comprise SEQ ID NOs: 31-33, respectively, and the $V_L$CDR1, $V_L$CDR2, and $V_L$CDR3 sequences comprise SEQ ID NOs: 34-36, respectively;

the $V_H$CDR1, $V_H$CDR2, and $V_H$CDR3 sequences comprise SEQ ID NOs: 34-39, respectively, and the $V_L$CDR1, $V_L$CDR2, and $V_L$CDR3 sequences comprise SEQ ID NOs: 40-42, respectively;

the $V_H$CDR1, $V_H$CDR2, and $V_H$CDR3 sequences comprise SEQ ID NOs: 43-45, respectively, and the $V_L$CDR1, $V_L$CDR2, and $V_L$CDR3 sequences comprise SEQ ID NOs: 46-48, respectively;

the $V_H$CDR1, $V_H$CDR2, and $V_H$CDR3 sequences comprise SEQ ID NOs: 49-51, respectively, and the $V_L$CDR1, $V_L$CDR2, and $V_L$CDR3 sequences comprise SEQ ID NOs: 52-54, respectively;

the $V_H$CDR1, $V_H$CDR2, and $V_H$CDR3 sequences comprise SEQ ID NOs: 55-57, respectively, and the $V_L$CDR1, $V_L$CDR2, and $V_L$CDR3 sequences comprise SEQ ID NOs: 58-60, respectively;

the $V_H$CDR1, $V_H$CDR2, and $V_H$CDR3 sequences comprise SEQ ID NOs: 61-63, respectively, and the $V_L$CDR1, $V_L$CDR2, and $V_L$CDR3 sequences comprise SEQ ID NOs: 64-66, respectively;

the $V_H$CDR1, $V_H$CDR2, and $V_H$CDR3 sequences comprise SEQ ID NOs: 67-69, respectively, and the $V_L$CDR1, $V_L$CDR2, and $V_L$CDR3 sequences comprise SEQ ID NOs: 70-72, respectively;

the $V_H$CDR1, $V_H$CDR2, and $V_H$CDR3 sequences comprise SEQ ID NOs: 73-75, respectively, and the $V_L$CDR1, $V_L$CDR2, and $V_L$CDR3 sequences comprise SEQ ID NOs: 76-78, respectively;

the $V_H$CDR1, $V_H$CDR2, and $V_H$CDR3 sequences comprise SEQ ID NOs: 79-81, respectively, and the $V_L$CDR1, $V_L$CDR2, and $V_L$CDR3 sequences comprise SEQ ID NOs: 82-84, respectively;

the V$_H$CDR1, V$_H$CDR2, and V$_H$CDR3 sequences comprise SEQ ID NOs: 85-87, respectively, and the V$_L$CDR1, V$_L$CDR2, and V$_L$CDR3 sequences comprise SEQ ID NOs: 88-90, respectively;

the V$_H$CDR1, V$_H$CDR2, and V$_H$CDR3 sequences comprise SEQ ID NOs: 91-93, respectively, and the V$_L$CDR1, V$_L$CDR2, and V$_L$CDR3 sequences comprise SEQ ID NOs: 94-96, respectively;

the V$_H$CDR1, V$_H$CDR2, and V$_H$CDR3 sequences comprise SEQ ID NOs: 97-99, respectively, and the V$_L$CDR1, V$_L$CDR2, and V$_L$CDR3 sequences comprise SEQ ID NOs: 100-102, respectively;

the V$_H$CDR1, V$_H$CDR2, and V$_H$CDR3 sequences comprise SEQ ID NOs: 103-105, respectively, and the V$_L$CDR1, V$_L$CDR2, and V$_L$CDR3 sequences comprise SEQ ID NOs: 106-108, respectively;

the V$_H$CDR1, V$_H$CDR2, and V$_H$CDR3 sequences comprise SEQ ID NOs: 109-111, respectively, and the V$_L$CDR1, V$_L$CDR2, and V$_L$CDR3 sequences comprise SEQ ID NOs: 112-114, respectively;

the V$_H$CDR1, V$_H$CDR2, and V$_H$CDR3 sequences comprise SEQ ID NOs: 115-117, respectively, and the V$_L$CDR1, V$_L$CDR2, and V$_L$CDR3 sequences comprise SEQ ID NOs: 118-120, respectively;

the V$_H$CDR1, V$_H$CDR2, and V$_H$CDR3 sequences comprise SEQ ID NOs: 121-123, respectively, and the V$_L$CDR1, V$_L$CDR2, and V$_L$CDR3 sequences comprise SEQ ID NOs: 124-126, respectively;

the V$_H$CDR1, V$_H$CDR2, and V$_H$CDR3 sequences comprise SEQ ID NOs: 127-129, respectively, and the V$_L$CDR1, V$_L$CDR2, and V$_L$CDR3 sequences comprise SEQ ID NOs: 130-132, respectively;

the V$_H$CDR1, V$_H$CDR2, and V$_H$CDR3 sequences comprise SEQ ID NOs: 133-135, respectively, and the V$_L$CDR1, V$_L$CDR2, and V$_L$CDR3 sequences comprise SEQ ID NOs: 136-138, respectively;

the V$_H$CDR1, V$_H$CDR2, and V$_H$CDR3 sequences comprise SEQ ID NOs: 139-141, respectively, and the V$_L$CDR1, V$_L$CDR2, and V$_L$CDR3 sequences comprise SEQ ID NOs: 142-144, respectively;

the V$_H$CDR1, V$_H$CDR2, and V$_H$CDR3 sequences comprise SEQ ID NOs: 145-147, respectively, and the V$_L$CDR1, V$_L$CDR2, and V$_L$CDR3 sequences comprise SEQ ID NOs: 148-150, respectively;

the V$_H$CDR1, V$_H$CDR2, and V$_H$CDR3 sequences comprise SEQ ID NOs: 151-153, respectively, and the V$_L$CDR1, V$_L$CDR2, and V$_L$CDR3 sequences comprise SEQ ID NOs: 154-156, respectively;

the V$_H$CDR1, V$_H$CDR2, and V$_H$CDR3 sequences comprise SEQ ID NOs: 157-159, respectively, and the V$_L$CDR1, V$_L$CDR2, and V$_L$CDR3 sequences comprise SEQ ID NOs: 160-162, respectively;

the V$_H$CDR1, V$_H$CDR2, and V$_H$CDR3 sequences comprise SEQ ID NOs: 163-165, respectively, and the V$_L$CDR1, V$_L$CDR2, and V$_L$CDR3 sequences comprise SEQ ID NOs: 166-168, respectively;

the V$_H$CDR1, V$_H$CDR2, and V$_H$CDR3 sequences comprise SEQ ID NOs: 169-171, respectively, and the V$_L$CDR1, V$_L$CDR2, and V$_L$CDR3 sequences comprise SEQ ID NOs: 172-174, respectively;

the V$_H$CDR1, V$_H$CDR2, and V$_H$CDR3 sequences comprise SEQ ID NOs: 175-177, respectively, and the V$_L$CDR1, V$_L$CDR2, and V$_L$CDR3 sequences comprise SEQ ID NOs: 178-180, respectively;

the V$_H$CDR1, V$_H$CDR2, and V$_H$CDR3 sequences comprise SEQ ID NOs: 181-183, respectively, and the V$_L$CDR1, V$_L$CDR2, and V$_L$CDR3 sequences comprise SEQ ID NOs: 184-186, respectively; or the V$_H$CDR1, V$_H$CDR2, and V$_H$CDR3 sequences comprise SEQ ID NOs: 187-189, respectively, and the V$_L$CDR1, V$_L$CDR2, and V$_L$CDR3 sequences comprise SEQ ID NOs: 190-192, respectively.

In some embodiments, the V$_H$ comprises a sequence at least 80, 85, 90, 95, 97, 98, 99, or 100% identical to a sequence selected from Table A2, optionally wherein the V$_H$ has 1, 2, 3, 4, 5, 6, 7, 8, 9, or 10 alterations in the framework regions. In some embodiments, the V$_L$ comprises a sequence at least 80, 85, 90, 95, 97, 98, 99, or 100% identical to a sequence selected from Table A2, optionally wherein the V$_L$ has 1, 2, 3, 4, 5, 6, 7, 8, 9, or 10 alterations in the framework regions.

In certain embodiments:

the V$_H$ comprises a sequence at least 80, 85, 90, 95, 97, 98, 99, or 100% identical to SEQ ID NO: 193, and the V$_L$ comprises a sequence at least 80, 85, 90, 95, 97, 98, 99, or 100% identical to SEQ ID NO: 194;

the V$_H$ comprises a sequence at least 80, 85, 90, 95, 97, 98, 99, or 100% identical to SEQ ID NO: 195, and the V$_L$ comprises a sequence at least 80, 85, 90, 95, 97, 98, 99, or 100% identical to SEQ ID NO: 196;

the V$_H$ comprises a sequence at least 80, 85, 90, 95, 97, 98, 99, or 100% identical to SEQ ID NO: 197, and the V$_L$ comprises a sequence at least 80, 85, 90, 95, 97, 98, 99, or 100% identical to SEQ ID NO: 198;

the V$_H$ comprises a sequence at least 80, 85, 90, 95, 97, 98, 99, or 100% identical to SEQ ID NO: 199, and the V$_L$ comprises a sequence at least 80, 85, 90, 95, 97, 98, 99, or 100% identical to SEQ ID NO: 200;

the V$_H$ comprises a sequence at least 80, 85, 90, 95, 97, 98, 99, or 100% identical to SEQ ID NO: 201, and the V$_L$ comprises a sequence at least 80, 85, 90, 95, 97, 98, 99, or 100% identical to SEQ ID NO: 202;

the V$_H$ comprises a sequence at least 80, 85, 90, 95, 97, 98, 99, or 100% identical to SEQ ID NO: 203, and the V$_L$ comprises a sequence at least 80, 85, 90, 95, 97, 98, 99, or 100% identical to SEQ ID NO: 204;

the V$_H$ comprises a sequence at least 80, 85, 90, 95, 97, 98, 99, or 100% identical to SEQ ID NO: 205, and the V$_L$ comprises a sequence at least 80, 85, 90, 95, 97, 98, 99, or 100% identical to SEQ ID NO: 206;

the V$_H$ comprises a sequence at least 80, 85, 90, 95, 97, 98, 99, or 100% identical to SEQ ID NO: 207, and the V$_L$ comprises a sequence at least 80, 85, 90, 95, 97, 98, 99, or 100% identical to SEQ ID NO: 208;

the V$_H$ comprises a sequence at least 80, 85, 90, 95, 97, 98, 99, or 100% identical to SEQ ID NO: 209, and the V$_L$ comprises a sequence at least 80, 85, 90, 95, 97, 98, 99, or 100% identical to SEQ ID NO: 210;

the V$_H$ comprises a sequence at least 80, 85, 90, 95, 97, 98, 99, or 100% identical to SEQ ID NO: 211, and the V$_L$ comprises a sequence at least 80, 85, 90, 95, 97, 98, 99, or 100% identical to SEQ ID NO: 212;

the V$_H$ comprises a sequence at least 80, 85, 90, 95, 97, 98, 99, or 100% identical to SEQ ID NO: 213, and the V$_L$ comprises a sequence at least 80, 85, 90, 95, 97, 98, 99, or 100% identical to SEQ ID NO: 214;

the V$_H$ comprises a sequence at least 80, 85, 90, 95, 97, 98, 99, or 100% identical to SEQ ID NO: 215, and the V$_L$ comprises a sequence at least 80, 85, 90, 95, 97, 98, 99, or 100% identical to SEQ ID NO: 216;

the V$_H$ comprises a sequence at least 80, 85, 90, 95, 97, 98, 99, or 100% identical to SEQ ID NO: 217, and the $V_L$ comprises a sequence at least 80, 85, 90, 95, 97, 98, 99, or 100% identical to SEQ ID NO: 218;

the $V_H$ comprises a sequence at least 80, 85, 90, 95, 97, 98, 99, or 100% identical to SEQ ID NO: 219, and the $V_L$ comprises a sequence at least 80, 85, 90, 95, 97, 98, 99, or 100% identical to SEQ ID NO: 220;

the $V_H$ comprises a sequence at least 80, 85, 90, 95, 97, 98, 99, or 100% identical to SEQ ID NO: 221, and the $V_L$ comprises a sequence at least 80, 85, 90, 95, 97, 98, 99, or 100% identical to SEQ ID NO: 222;

the $V_H$ comprises a sequence at least 80, 85, 90, 95, 97, 98, 99, or 100% identical to SEQ ID NO: 223, and the $V_L$ comprises a sequence at least 80, 85, 90, 95, 97, 98, 99, or 100% identical to SEQ ID NO: 224;

the $V_H$ comprises a sequence at least 80, 85, 90, 95, 97, 98, 99, or 100% identical to SEQ ID NO: 225, and the $V_L$ comprises a sequence at least 80, 85, 90, 95, 97, 98, 99, or 100% identical to SEQ ID NO: 226;

the $V_H$ comprises a sequence at least 80, 85, 90, 95, 97, 98, 99, or 100% identical to SEQ ID NO: 227, and the $V_L$ comprises a sequence at least 80, 85, 90, 95, 97, 98, 99, or 100% identical to SEQ ID NO: 228;

the $V_H$ comprises a sequence at least 80, 85, 90, 95, 97, 98, 99, or 100% identical to SEQ ID NO: 229, and the $V_L$ comprises a sequence at least 80, 85, 90, 95, 97, 98, 99, or 100% identical to SEQ ID NO: 230;

the $V_H$ comprises a sequence at least 80, 85, 90, 95, 97, 98, 99, or 100% identical to SEQ ID NO: 231, and the $V_L$ comprises a sequence at least 80, 85, 90, 95, 97, 98, 99, or 100% identical to SEQ ID NO: 232;

the $V_H$ comprises a sequence at least 80, 85, 90, 95, 97, 98, 99, or 100% identical to SEQ ID NO: 233, and the $V_L$ comprises a sequence at least 80, 85, 90, 95, 97, 98, 99, or 100% identical to SEQ ID NO: 234;

the $V_H$ comprises a sequence at least 80, 85, 90, 95, 97, 98, 99, or 100% identical to SEQ ID NO: 235, and the $V_L$ comprises a sequence at least 80, 85, 90, 95, 97, 98, 99, or 100% identical to SEQ ID NO: 236;

the $V_H$ comprises a sequence at least 80, 85, 90, 95, 97, 98, 99, or 100% identical to SEQ ID NO: 237, and the $V_L$ comprises a sequence at least 80, 85, 90, 95, 97, 98, 99, or 100% identical to SEQ ID NO: 238;

the $V_H$ comprises a sequence at least 80, 85, 90, 95, 97, 98, 99, or 100% identical to SEQ ID NO: 239, and the $V_L$ comprises a sequence at least 80, 85, 90, 95, 97, 98, 99, or 100% identical to SEQ ID NO: 240;

the $V_H$ comprises a sequence at least 80, 85, 90, 95, 97, 98, 99, or 100% identical to SEQ ID NO: 241, and the $V_L$ comprises a sequence at least 80, 85, 90, 95, 97, 98, 99, or 100% identical to SEQ ID NO: 242;

the $V_H$ comprises a sequence at least 80, 85, 90, 95, 97, 98, 99, or 100% identical to SEQ ID NO: 243, and the $V_L$ comprises a sequence at least 80, 85, 90, 95, 97, 98, 99, or 100% identical to SEQ ID NO: 244;

the $V_H$ comprises a sequence at least 80, 85, 90, 95, 97, 98, 99, or 100% identical to SEQ ID NO: 245, and the $V_L$ comprises a sequence at least 80, 85, 90, 95, 97, 98, 99, or 100% identical to SEQ ID NO: 246;

the $V_H$ comprises a sequence at least 80, 85, 90, 95, 97, 98, 99, or 100% identical to SEQ ID NO: 247, and the $V_L$ comprises a sequence at least 80, 85, 90, 95, 97, 98, 99, or 100% identical to SEQ ID NO: 248;

the $V_H$ comprises a sequence at least 80, 85, 90, 95, 97, 98, 99, or 100% identical to SEQ ID NO: 249, and the $V_L$ comprises a sequence at least 80, 85, 90, 95, 97, 98, 99, or 100% identical to SEQ ID NO: 250;

the $V_H$ comprises a sequence at least 80, 85, 90, 95, 97, 98, 99, or 100% identical to SEQ ID NO: 251, and the $V_L$ comprises a sequence at least 80, 85, 90, 95, 97, 98, 99, or 100% identical to SEQ ID NO: 252;

the $V_H$ comprises a sequence at least 80, 85, 90, 95, 97, 98, 99, or 100% identical to SEQ ID NO: 253, and the $V_L$ comprises a sequence at least 80, 85, 90, 95, 97, 98, 99, or 100% identical to SEQ ID NO: 254; or the $V_H$ comprises a sequence at least 80, 85, 90, 95, 97, 98, 99, or 100% identical to SEQ ID NO: 255, and the $V_L$ comprises a sequence at least 80, 85, 90, 95, 97, 98, 99, or 100% identical to SEQ ID NO: 256.

In some embodiments, the isolated antibody, or antigen binding fragment thereof, binds to human IL-11Rα (see Table B1). In specific embodiments, the isolated antibody, or antigen binding fragment thereof, binds to a fibronectin domain III of human IL-11Rα, or approximately residues 112-219 of SEQ ID NO: 257. In some embodiments, the isolated antibody, or antigen binding fragment thereof, has one or more of the following characteristics:

a binding affinity for human IL-11Rα of less than about 500, 400, 300, 200, 100, 90, 80, 70, 60, 50, 40, or 30 pM, and optionally has increased binding affinity for human IL-11Rα relative to that of the TS7 and 8E2 antibodies; antagonizes the binding and/or signaling activity between IL-11Rα and IL-11, and optionally has increased potency as an IL-11 signaling antagonist relative to that of the TS7 and 8E2 antibodies; reduces IL-11Rα/gp130 dimerization or complex formation, optionally in a cell-based assay; and/or reduced N-linked glycosylation in $V_L$CDR3, optionally relative to the TS7 and 8E2 antibodies.

In some embodiments, an isolated antibody, or antigen binding fragment thereof, comprises an IgA (including subclasses IgA1 and IgA2), IgD, IgE, IgG (including subclasses IgG1, IgG2, IgG3, and IgG4), or IgM Fc domain, optionally a human Fc domain, or a hybrid and/or variant thereof. In some embodiments, an isolated antibody, or antigen binding fragment thereof, comprises an IgG Fc domain with high effector function in humans, optionally an IgG1 or IgG3 Fc domain. In some embodiments, an isolated antibody, or antigen binding fragment thereof, comprises an IgG Fc domain with low effector function in humans, optionally an IgG2 or IgG4 Fc domain. In specific embodiments, an isolated antibody, or antigen binding fragment thereof, comprises a human IgG1 or IgG4 Fc domain, optionally selected from Table Ft.

In some embodiments, an isolated antibody, or antigen binding fragment thereof, is a monoclonal antibody. In some embodiments, an isolated antibody, or antigen binding fragment thereof, comprises is a humanized antibody, including wherein the antibody, or antigen binding fragment thereof, is a humanized monoclonal antibody that comprises a human IgG4 Fc domain with an S228P mutation (EU numbering). In some embodiments, an isolated antibody, or antigen binding fragment thereof, is selected from an Fv fragment, a single chain Fv (scFv) polypeptide, an adnectin, an anticalin, an aptamer, an avimer, a camelid antibody, a designed ankyrin repeat protein (DARPin), a minibody, a nanobody, and a unibody.

Also included are isolated polynucleotide(s) encoding an isolated antibody, or antigen binding fragment thereof, as described herein, expression vector(s) comprising the isolated polynucleotide(s), and an isolated host cell(s) comprising the vector(S).

Certain embodiments relate to pharmaceutical compositions, comprising an isolated antibody, or antigen binding fragment thereof, described herein, and a pharmaceutically acceptable carrier. In some embodiments, the composition has a purity of at least about 80%, 85%, 90%, 95%, 98%, or 99% on a protein basis with respect to the at least one antibody or antigen binding fragment, and is substantially aggregate- and endotoxin-free. In some embodiments, the composition has reduced or undetectable heterogeneity of N-linked glycosylation (optionally relative to the TS7 and 8E2 antibodies), optionally in the $V_L$CDR3 sequence. In some embodiments, the composition is a sterile, injectable solution, optionally suitable for intravenous, intramuscular, subcutaneous, or intraperitoneal administration.

Also included are methods of treating a disease or condition in a subject in need thereof, comprising administering to the subject a pharmaceutical composition described herein. In some embodiments, the disease or condition is an IL-11-associated or IL-11-mediated disease or condition.

In some embodiments, the disease or condition is a cancer, an inflammatory disease, an autoimmune disease, a wasting disease, a bone disease, or fibrosis.

In some embodiments, the disease is a cancer, optionally a cancer that expresses or overexpresses IL-11Rα and/or IL-11, optionally wherein the cancer displays IL-11Rα/IL-11-dependent growth, adhesion, migration, invasion, and/or chemoresistance. In some embodiments, the cancer is selected from one or more of bone cancer, prostate cancer, melanoma (e.g., metastatic melanoma), pancreatic cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia, hairy cell leukemias, acute lymphoblastic leukemias), lymphoma (e.g., non-Hodgkin's lymphomas, Hodgkin's lymphoma), hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer. In some embodiments, the cancer is a metastatic cancer, optionally a metastatic cancer which has metastasized to the bone.

In particular embodiments, the inflammatory disease is selected from one or more of airway or lung inflammation (e.g., inflammatory lung disease), asthma, rhinitis, chronic obstructive pulmonary disorder (COPD), dermatitis, psoriasis, hepatitis, gastric inflammation, irritable bowel syndrome (IBS), ulcerative colitis, Crohn's disease, colitis, diverticulitis, lupus erythematous, nephritis, Parkinson's disease, multiple sclerosis (MS), Alzheimer's disease, arthritis, rheumatoid arthritis, sepsis, infection-induced inflammation, cardiovascular diseases such as atherosclerosis and vasculitis, diabetes, and gout.

In certain embodiments, the autoimmune disease is selected from one or more of arthritis (including rheumatoid arthritis, reactive arthritis), systemic lupus erythematosus (SLE), psoriasis, inflammatory bowel disease (IBD), ulcerative colitis, Crohn's disease, encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, fibromyalgia, pemphigus vulgaris, Sjogren's syndrome, Kawasaki's Disease, hyperthyroidism/ Graves' disease, hypothyroidism/Hashimoto's disease, endometriosis, scleroderma, pernicious anemia, Goodpasture syndrome, Guillain-Barré syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis, rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

In some embodiments, the wasting disease is selected from one or more of cachexia, optionally cachexia associated with cancer or renal failure, and sarcopenia.

In some embodiments, the bone disease is selected from osteoporosis (including post-menopausal osteoporosis), bone fracture, Paget's disease of bone, and bone resorption/ damage associated with cancer or cancer therapy, including chemotherapy, hormone ablation, and hormone inhibition.

In some embodiments, the fibrosis is selected from fibrosis of the lungs, cardiovascular system, liver, brain, joints (optionally knee, hip, ankle, foot joints, shoulder, elbow, wrist, hand joints, or spinal vertebrae), intestine, skin, kidney, liver, thyroid, bone marrow, retroperitoneum, and eye. In certain embodiments, the fibrosis of the lungs is selected from fibrothorax, pulmonary fibrosis (optionally cystic fibrosis or interstitial lung disease (ILD)), autosomal recessive genetic disease optionally Hermansky-Pudlak syndrome, and radiation-induced lung injury. In specific embodiments, the ILD is idiopathic ILD, optionally selected from idiopathic pulmonary fibrosis (IPF), desquamative interstitial pneumonia (DIP), acute interstitial pneumonia (AIP) or Hamman-Rich syndrome, nonspecific interstitial pneumonia (NSIP), respiratory bronchiolitis-associated interstitial lung disease (RB-ILD), cryptogenic organizing pneumonia (COP), and lymphoid interstitial pneumonia (LIP). In certain embodiments, the ILD is secondary ILD, optionally selected from ILD related to connective tissue and autoimmune diseases (optionally sarcoidosis, rheumatoid arthritis, systemic lupus erythematosus, systemic sclerosis, polymyositis, dermatomyositis, or antisynthetase syndrome), inhaled substances (optionally silicosis, asbestosis, berylliosis, industrial printing chemicals, or chronic hypersensitivity pneumonitis), drugs (optionally antibiotics, chemotherapeutics, or anti-arrhythmic agents), infections (optionally SARS CoV-2, atypical pneumonia, pneumocystis pneumonia, tuberculosis, *Chlamydia trachomatis*, or respiratory syncytial virus), malignancies (optionally lymphangitic carcinomatosis), and pediatric ILDs (optionally developmental disorders, growth abnormalities deficient alveolarization, infant conditions of undefined cause, and ILD related to alveolar surfactant region).

In some embodiments, the fibrosis of the cardiovascular system is myocardial fibrosis (for example, interstitial fibrosis or replacement fibrosis).

from Donor 1 (3A) and Donor 2 (3B). LDH release is given as % of octylphenol ethoxylate (TRITON™ X) lysed control (set to 100%). Bars show mean±SD, with dots representing technical replicates (duplicate wells with 2 PCLS each). For donor 2 (3B), supernatants of duplicate wells were pooled before measurement. Region 1 is subpleural, region 2 is central.

Figure 4A:
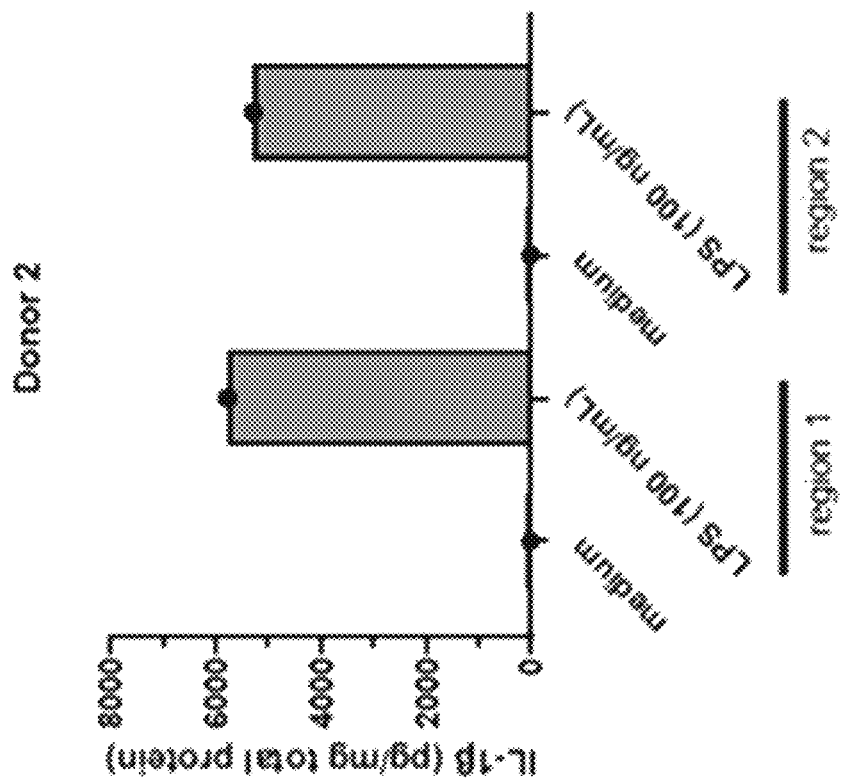
Figure 4B:
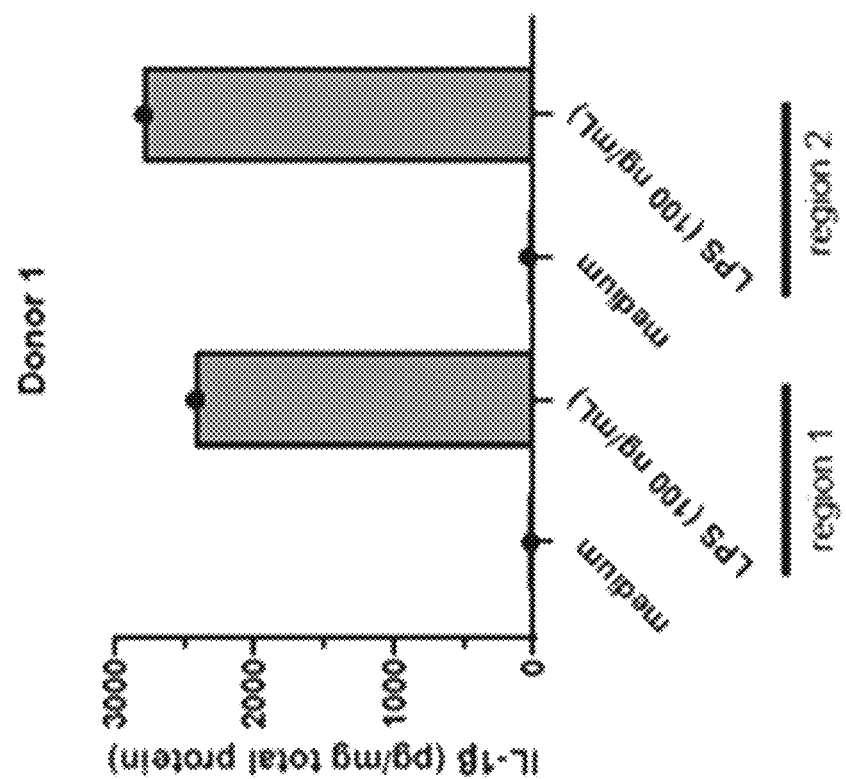

FIGS. 4A-4B show IL-1β upregulation in LPS treated PCLS from Donor 1 (4A) and Donor 2 (4B). IL-1β was determined in PCLS lysates by ELISA and normalized to total protein concentration of the tissue. Data are shown as mean±SD. For each condition, lysates from duplicate wells (with 2 PCLS each) were pooled before measurement. Region 1 is subpleural, region 2 is central.

Figure 5:
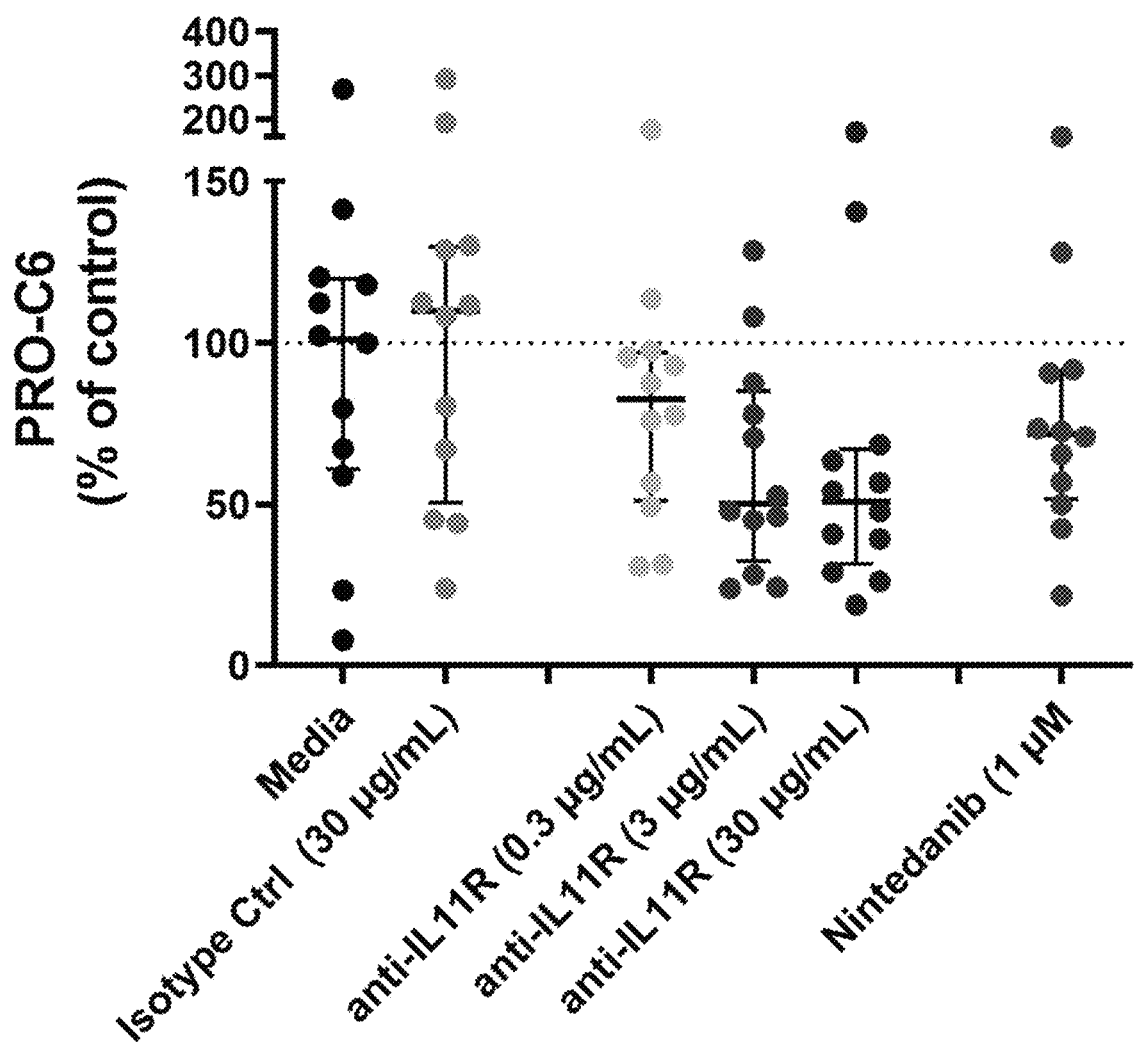

FIG. 5 shows type VI collagen formation evaluated by PRO-C6 across all donors and regions. Region 1 is subpleural, region 2 is central. Data are presented as percentage of the no treatment (media) control and shown as individual data points for three replicates from each region from each donor (total of 12) and with indication of the median and interquartile range.

DETAILED DESCRIPTION

The present disclosure relates to antibodies, and antigen binding fragments thereof, which specifically bind to interleukin-11 receptor subunit α (IL-11Rα), in particular antibodies having epitopic specificity and improved characteristics. Examples of such improved characteristics include increased binding affinity for IL-11Rα, increased potency as interleukin-11 (IL-11) signaling inhibitors/antagonists, and improved developability, such as increased manufacturing homogeneity, for example, due to decreased heterogeneity at potential N-linked glycosylation sites. Some embodiments thus include specific humanized antibodies and fragments thereof capable of binding to IL-11Rα, blocking IL-11Rα binding with its ligand IL-11, and inhibiting downstream cell signaling and biological effects. In certain embodiments, an anti-IL-11Rα antibody, or antigen binding fragment thereof, is a IL-11Rα antagonist or inhibitor.

IL-11Rα antagonist antibodies described herein are useful in the treatment and prevention of various diseases and conditions, such as cancers, autoimmune diseases, and inflammatory diseases, including diseases and conditions associated with or mediated by IL-11 signaling. Some embodiments thus relate to the use of anti-IL-11Rα antibodies, or antigen binding fragments thereof, for the diagnosis, assessment, and treatment of diseases and conditions, including those associated with IL-11 activity or aberrant expression thereof.

The practice of the present disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y.(2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes. As used herein, the term "antigen" includes substances that are capable, under appropriate conditions, of inducing an immune response to the substance and of reacting with the products of the immune response. For example, an antigen can be recognized by antibodies (humoral immune response) or sensitized T-lymphocytes (T helper or cell-mediated immune response), or both. Antigens can be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" includes any substance to which an antibody binds, or for which antibodies are desired, regardless of whether the substance is immunogenic. For such antigens, antibodies can be identified by recombinant methods, independently of any immune response.

An "antagonist" refers to an agent (e.g., antibody) that interferes with or otherwise reduces the physiological action of another agent or molecule. In some instances, the antagonist specifically binds to the other agent or molecule. Included are full and partial antagonists.

An "agonist" refers to an agent (e.g., antibody) that increases or enhances the physiological action of another agent or molecule. In some instances, the agonist specifically binds to the other agent or molecule. Included are full and partial agonists.

As used herein, the term "amino acid" is intended to mean both naturally occurring and non-naturally occurring amino acids as well as amino acid analogs and mimetics. Naturally-occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, the term "antibody" encompasses not only intact polyclonal or monoclonal antibodies, but also fragments thereof (such as dAb, Fab, Fab', F(ab')2, Fv), single chain (scFv), synthetic variants thereof, naturally occurring variants, fusion proteins comprising an antibody portion with an antigen binding fragment of the required specificity, humanized antibodies, chimeric antibodies, and any other modified configuration of the immunoglobulin molecule that comprises an antigen binding site or fragment (epitope recognition site) of the required specificity. Certain features and characteristics of antibodies (and antigen binding fragments thereof) are described in greater detail herein.

An antibody or antigen binding fragment can be of essentially any type. As is well known in the art, an antibody is an immunoglobulin molecule capable of specific binding to a target, such as an immune checkpoint molecule, through at least one epitope recognition site, located in the variable region of the immunoglobulin molecule.

The term "antigen binding fragment" as used herein refers to a polypeptide fragment that contains at least one CDR of an immunoglobulin heavy and/or light chain that binds to the antigen of interest. In this regard, an antigen binding fragment of the herein described antibodies may comprise 1, 2, 3, 4, 5, or all 6 CDRs of a $V_H$ and $V_L$ sequence from antibodies that bind to a target molecule.

The binding properties of antibodies and antigen binding fragments thereof can be quantified using methods well known in the art (see Davies et al., Annual Rev. Biochem. 59:439-473, 1990). In some embodiments, an antibody or antigen binding fragment thereof specifically binds to a target molecule, for example, an IL-11Rα polypeptide or an epitope or complex thereof, with an equilibrium dissociation constant that is about or ranges from about $\leq 10^{-7}$ M to about $\leq 10^{-8}$ M. In some embodiments, the equilibrium dissociation constant is about or ranges from about $\leq 10^{-9}$ M to about $\leq 10^{-10}$ M. In certain illustrative embodiments, an antibody or antigen binding fragment thereof has an affinity ($K_D$ or $EC_{50}$) for a target molecule (to which it specifically binds) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

A molecule such as a polypeptide or antibody is said to exhibit "specific binding" or "preferential binding" if it reacts or associates more frequently, more rapidly, with greater duration and/or with greater affinity with a particular cell, substance, or particular epitope than it does with alternative cells or substances, or epitopes. An antibody "specifically binds" or "preferentially binds" to a target molecule or epitope if it binds with greater affinity, avidity, more readily, and/or with greater duration than it binds to other substances or epitopes, for example, by a statistically significant amount. Typically one member of the pair of molecules that exhibit specific binding has an area on its surface, or a cavity, which specifically binds to and is therefore complementary to a particular spatial and/or polar organization of the other member of the pair of molecules. Thus, the members of the pair have the property of binding specifically to each other. For instance, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. The term is also applicable where, for example, an antibody is specific for a particular epitope which is carried by a number of antigens, in which case the specific binding member carrying the antigen binding fragment or domain will be able to bind to the various antigens carrying the epitope; for example, it may be cross reactive to a number of different forms of a target antigen from multiple species that share a common epitope Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant $K_D$. As used herein, the term "affinity" includes the equilibrium constant for the reversible binding of two agents and is expressed as $K_D$ or $EC_{50}$. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution. In some embodiments, affinity is expressed in the terms of the half maximal effective concentration ($EC_{50}$), which refers to the concentration of an agent, such as an antibody, or an anti-IL-11Rα antibody, as disclosed herein, which induces a response halfway between the baseline and maximum after a specified exposure time. The $EC_{50}$ is commonly used as a measure of an antibody's potency.

Antibodies can be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest can be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S.

Pat. No. 7,244,592; Chao et al., Nature Protocols. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

In certain embodiments, antibodies and antigen binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen binding site, particularly the FR residues directly adjacent to the CDRs. Within FRs, certain amino residues and certain structural features are very highly conserved. In this regard, most V region sequences contain an internal disulfide loop of around 90 amino acid residues. When the V regions fold into a binding-site, the CDRs are displayed as projecting loop motifs which form an antigen binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')2, Fv), single chain (scFv), variants thereof, fusion proteins comprising an antigen binding portion, humanized monoclonal antibodies, chimeric monoclonal antibodies, and any other modified configuration of the immunoglobulin molecule that comprises an antigen binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen binding site. The enzyme pepsin is able to cleave IgG molecules to provide several fragments, including the F(ab')2 fragment which comprises both antigen binding sites. An Fv fragment for use according to certain embodiments can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH::VL heterodimer including an antigen binding site which retains much of the antigen recognition and binding capabilities of the native antibody molecule (Inbar et al., PNAS USA. 69:2659-2662, 1972; Hochman et al., Biochem. 15:2706-2710, 1976; and Ehrlich et al., Biochem. 19:4091-4096, 1980). In some embodiments, Fvs are stabilized by other means, for example, incorporation of at least one disulfide bond (Wörn & Pluckthun, J. Mol. Biol. 305, 989-1010, 2001)

In certain embodiments, single chain Fv (scFV) antibodies are contemplated. For example, Kappa bodies (Ill et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., EMBO J 10: 3655-59, 1991; and Traunecker et al., Int. J. Cancer Suppl. 7:51-52, 1992), may be prepared using standard molecular biology techniques following the teachings of the present application with regard to selecting antibodies having the desired specificity.

A single chain Fv (scFv) polypeptide is a covalently linked VH::VL heterodimer which is expressed from a gene fusion including VH- and VL-encoding genes linked by a peptide-encoding linker. Huston et al. (PNAS USA. 85(16): 5879-5883, 1988). A number of methods have been described to discern chemical structures for converting the naturally aggregated—but chemically separated—light and heavy polypeptide chains from an antibody V region into an scFv molecule which will fold into a three dimensional structure substantially similar to the structure of an antigen binding site. See, e.g., U.S. Pat. Nos. 5,091,513 and 5,132,405, to Huston et al.; and U.S. Pat. No. 4,946,778, to Ladner et al.

In certain embodiments, the antibodies or antigen binding fragments described herein are in the form of a "diabody." Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward et al., Nature 341:544-546, 1989). Diabodies and other multivalent or multispecific fragments can be constructed, for example, by gene fusion (see WO94/13804; and Holliger et al., PNAS USA. 90:6444-6448, 1993)).

Minibodies comprising a scFv joined to a CH3 domain are also included (see Hu et al., Cancer Res. 56:3055-3061, 1996). See also Ward et al., Nature. 341:544-546, 1989; Bird et al., Science. 242:423-426, 1988; Huston et al., PNAS USA. 85:5879-5883, 1988); PCT/US92/09965; WO94/13804; and Reiter et al., Nature Biotech. 14:1239-1245, 1996.

Where bispecific antibodies are to be used, these may be conventional bispecific antibodies, which can be manufactured in a variety of ways (Holliger and Winter, Current Opinion Biotechnol. 4:446-449, 1993), e.g., prepared chemically or from hybrid hybridomas, or may be any of the bispecific antibody fragments mentioned above.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by a number of methods (Brinkman & Kontermann, mAbs 9:182-212, 2017) including knobs-into-holes engineering (Ridgeway et al., Protein Eng. 9:616-621, 1996).

In certain embodiments, the antibodies or antigen binding fragments described herein are in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies and antigen binding fragments described herein are in the form of a nanobody. Nanobodies are encoded by single genes and are efficiently produced in almost all prokaryotic and eukaryotic hosts, for example, E. coli (see U.S. Pat. No. 6,765,087), molds (for example Aspergillus or Trichoderma) and yeast (for example Saccharomyces, Kluyveromyces, Hansenula or Pichia (see U.S. Pat. No. 6,838,254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nanobodies against a desired target, based on automated high-throughput selection of B-cells.

In some embodiments, the antibodies or antigen binding fragments described herein are in the form of an aptamer (see, e.g., Ellington et al., Nature. 346, 818-22, 1990; and Tuerk et al., Science. 249, 505-10, 1990, incorporated by reference). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620, incorporated by reference.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments utilize the bacterial protein Thioredoxin-A as a scaffold protein, the variable loop being inserted within the reducing active site (-Cys-Gly-Pro-Cys-loop in the wild protein), with the two cysteines lateral chains being able to form a disulfide bridge. Methods for identifying peptide aptamers are described, for example, in U.S. Application No. 2003/0108532, incorporated by reference. Peptide aptamer selection can be performed using different systems known in the art, including the yeast two-hybrid system.

In some embodiments, the antibodies or antigen binding fragments described herein are in the form of an avimer. Avimers refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., Nature Biotechnology. 23:1556-1561, 2005; U.S. Pat. No. 7,166,697; and U.S. Application Nos. 2004/0175756, 2005/0048512, 2005/0053973, 2005/0089932 and 2005/0221384, incorporated by reference.

In some embodiments, the antibodies or antigen binding fragments described herein are in the form of an adnectin. Adnectins refer to a class of targeted biologics derived from human fibronectin, an abundant extracellular protein that naturally binds to other proteins. See, e.g., U.S. Application Nos. 2007/0082365; 2008/0139791; and 2008/0220049, incorporated by reference. Adnectins typically consists of a natural fibronectin backbone, as well as the multiple targeting domains of a specific portion of human fibronectin. The targeting domains can be engineered to enable an adnectin to specifically recognize an IL-11Rα polypeptide or an epitope thereof.

In some embodiments, the antibodies or antigen binding fragments described herein are in the form of an anticalin.

Anticalins refer to a class of antibody mimetics that are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable β-barrel scaffold) that are pairwise connected by four peptide loops and an attached α-helix. In certain aspects, conformational deviations to achieve specific binding are made in the hypervariable loop region(s). See, e.g., Skerra, FEBS J. 275:2677-83, 2008, incorporated by reference.

In some embodiments, the antibodies or antigen binding fragments described herein are in the form of a designed ankyrin repeat protein (DARPin). DARPins include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple receptors with one molecule composed of several DARPins. See, e.g., Stumpp et al., Curr Opin Drug Discov Devel. 10:153-159, 2007; U.S. Application No. 2009/0082274; and PCT/EP2001/10454, incorporated by reference.

Also included are heavy chain dimers, such as antibodies from camelids and sharks. Camelid and shark antibodies comprise a homodimeric pair of two chains of V-like and C-like domains (neither has a light chain). Since the $V_H$ of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Shark Ig-NARs comprise a homodimer of one variable domain (termed a V-NAR domain) and five C-like constant domains (C-NAR domains).

In camelids, the diversity of antibody repertoire is determined by the complementary determining regions (CDR) 1, 2, and 3 in the VH or VHH regions. The CDR3 in the camelid VHH region is characterized by its relatively long length averaging 16 amino acids (Muyldermans et al., 1994, Protein Engineering 7(9): 1129). This is in contrast to CDR3 regions of antibodies of many other species. For example, the CDR3 of mouse VH has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421, published Feb. 17, 2005

In certain embodiments, the antibodies or antigen binding fragments thereof are humanized. These embodiments refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen binding site may comprise either complete variable domains fused onto constant domains or only the CDRs (entire or in part) grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991; Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In some embodiments, only some of the CDR sequences are grafted from the nonhuman antibody (Bowers et al., J. Biol. Chem. 288:7688-7696, 2013). In certain embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies are "chimeric" antibodies. In this regard, a chimeric antibody is comprised of an antigen binding fragment of an antibody operably linked or otherwise fused to a heterologous Fc portion of a different antibody. In certain embodiments, the Fc domain or heterologous Fc domain is of human origin. In certain embodiments, the Fc domain or heterologous Fc domain is of mouse origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

The term "binding" refers to a direct association between two molecules, due to, for example, covalent, electrostatic, hydrophobic, and ionic and/or hydrogen-bond interactions, including interactions such as salt bridges and water bridges.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "effector function", or "ADCC effector function" in the context of antibodies refers to the ability of that antibody to engage with other arms of the immune system, including for example, the activation of the classical complement pathway, or through engagement of Fc receptors. Complement dependent pathways are primarily driven by the interaction of C1q with the C1 complex with clustered antibody Fc domains. Antibody dependent cellular cytotoxicity (ADCC), is primarily driven by the interaction of Fc receptors (FcRs) on the surface of effector cells (natural killer cells, macrophages, monocytes and eosinophils) which bind to the Fc region of an IgG which itself is bound to a target cell. Fc receptors (FcRs) are key immune regulatory receptors connecting the antibody mediated (humoral) immune response to cellular effector functions. Receptors for all classes of immunoglobulins have been identified, including FcγR (IgG), FcεRI (IgE), FcαRI (IgA), FcµR (IgM) and FcδR (IgD). There are at least three classes of receptors for human IgG found on leukocytes: CD64 (FcγRI), CD32 (FcγRIIa, FcγRIIb and FcγRIIc) and CD16 (FcγRIIIa and FcγRIIIb). FcγRI is classed as a high affinity receptor (nanomolar range $K_D$) while FcγRII and FcγRIII are low to intermediate affinity (micromolar range $K_D$). Upon Fc binding a signaling pathway is triggered which results in the secretion of various substances, such as lytic enzymes, perform, granzymes and tumor necrosis factor, which mediate in the destruction of the target cell. The level of ADCC effector function various for human IgG subtypes. Although this is dependent on the allotype and specific FcvR, in simple terms ADCC effector function is "high" for human IgG1 and IgG3, and "low" for IgG2 and IgG4.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The term "epitope" includes any determinant, preferably a polypeptide determinant, capable of specific binding to an immunoglobulin or T-cell receptor. An epitope includes a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen, for example, an IL-11Rα polypeptide. In particular embodiments, an epitope comprises, consists, or consists essentially of about, at least about, or no more than about 3, 4, 5, 6, 7, 8, 9, 10, 11, 12, 13, 14, 15, 16, 17, 18, 19, or 20 contiguous amino acids (i.e., a linear epitope) or non-contiguous amino acids (i.e., conformational epitope) of a reference sequence (see, e.g., Table B1) or target molecule described herein.

An "epitope" includes that portion of an antigen or other macromolecule capable of forming a binding interaction that interacts with the variable region binding pocket of a binding protein. Such binding interaction can be manifested as an intermolecular contact with one or more amino acid residues of a CDR. Antigen binding can involve a CDR3 or a CDR3 pair. An epitope can be a linear peptide sequence (i.e., "continuous") or can be composed of noncontiguous amino acid sequences (i.e., "conformational" or "discontinuous"). A binding protein can recognize one or more amino acid sequences; therefore an epitope can define more than one distinct amino acid sequence. Epitopes recognized by binding protein can be determined by peptide mapping and sequence analysis techniques well known to one of skill in the art. A "cryptic epitope" or a "cryptic binding site" is an epitope or binding site of a protein sequence that is not exposed or substantially protected from recognition within an unmodified polypeptide, but is capable of being recognized by a binding protein of a denatured or proteolyzed polypeptide. Amino acid sequences that are not exposed, or are only partially exposed, in the unmodified polypeptide structure are potential cryptic epitopes. If an epitope is not exposed, or only partially exposed, then it is likely that it is buried within the interior of the polypeptide. Candidate cryptic epitopes can be identified, for example, by examining the three-dimensional structure of an unmodified polypeptide.

The term "half maximal effective concentration" or "$EC_{50}$" refers to the concentration of an agent (e.g., antibody) as described herein at which it induces a response halfway between the baseline and maximum after some specified exposure time; the $EC_{50}$ of a graded dose response curve therefore represents the concentration of a compound at which 50% of its maximal effect is observed. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of an agent (e.g., antibody) is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, an agent will have an $EC_{50}$ value of about 1 nM or less.

"Immune response" means any immunological response originating from immune system, including responses from the cellular and humeral, innate and adaptive immune systems. Exemplary cellular immune cells include for example, lymphocytes, macrophages, T cells, B cells, NK cells, neutrophils, eosinophils, dendritic cells, mast cells, monocytes, and all subsets thereof. Cellular responses include for example, effector function, cytokine release, phagocytosis, efferocytosis, translocation, trafficking, proliferation, differentiation, activation, repression, cell-cell interactions, apoptosis, etc. Humeral responses include for example IgG, IgM, IgA, IgE, responses and their corresponding effector functions.

The "half-life" of an agent such as an antibody can refer to the time it takes for the agent to lose half of its pharmacologic, physiologic, or other activity, relative to such activity at the time of administration to the serum or tissue of an organism, or relative to any other defined time-point. "Half-life" can also refer to the time it takes for the amount or concentration of an agent to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing", "reducing", or "inhibiting", typically in a statistically significant or a physiologically significant amount or degree relative to a control. An "increased," "stimulated" or "enhanced" amount is typically a "statistically significant" amount, and may include an increase that is 1.1, 1.2, 1.5, 2, 3, 4, 5, 6, 7, 8, 9, 10, 15, 20, 30, 40, 50, 60, 70, 80, 90, 100 or more times (e.g., 500, 1000 times) (including all integers and ranges in between e.g., 1.5, 1.6, 1.7, 1.8, etc.) the amount produced by no composition (e.g., the absence of agent) or a control composition. A "decreased" or "reduced" or "inhibited" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "polynucleotide" and "nucleic acid" includes mRNA, RNA, cRNA, cDNA, and DNA. The term typically refers to polymeric form of nucleotides of at least 10 bases in length, either ribonucleotides or deoxynucleotides or a modified form of either type of nucleotide. The term includes single and double stranded forms of DNA. The terms "isolated DNA" and "isolated polynucleotide" and "isolated nucleic acid" refer to a molecule that has been isolated free of total genomic DNA of a particular species. Therefore, an isolated DNA segment encoding a polypeptide refers to a DNA segment that contains one or more coding sequences yet is substantially isolated away from, or purified free from, total genomic DNA of the species from which the DNA segment is obtained. Also included are non-coding polynucleotides (e.g., primers, probes, oligonucleotides), which do not encode a polypeptide. Also included are recombinant vectors, including, for example, expression vectors, viral vectors, plasmids, cosmids, phagemids, phage, viruses, and the like.

Additional coding or non-coding sequences may, but need not, be present within a polynucleotide described herein, and a polynucleotide may, but need not, be linked to other molecules and/or support materials. Hence, a polynucleotide or expressible polynucleotides, regardless of the length of the coding sequence itself, may be combined with other sequences, for example, expression control sequences.

"Expression control sequences" include regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, which have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease Si) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the -10 and -35 consensus sequences.

A large number of promoters, including constitutive, inducible and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-REx™ system (Invitrogen Carlsbad, CA), LacSwitch® (Stratagene, (San Diego, CA) and the Cre-ERT tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

An "expressible polynucleotide" includes a cDNA, RNA, mRNA or other polynucleotide that comprises at least one coding sequence and optionally at least one expression control sequence, for example, a transcriptional and/or translational regulatory element, and which can express an encoded polypeptide upon introduction into a cell, for example, a cell in a subject.

Various viral vectors that can be utilized to deliver an expressible polynucleotide include adenoviral vectors, herpes virus vectors, vaccinia virus vectors, adeno-associated virus (AAV) vectors, and retroviral vectors. In some instances, the retroviral vector is a derivative of a murine or avian retrovirus, or is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein. Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector.

In particular embodiments, the expressible polynucleotide is a modified RNA or modified mRNA polynucleotide, for example, a non-naturally occurring RNA analog. In certain embodiments, the modified RNA or mRNA polypeptide comprises one or more modified or non-natural bases, for example, a nucleotide base other than adenine (A), guanine (G), cytosine (C), thymine (T), and/or uracil (U). In some embodiments, the modified mRNA comprises one or more modified or non-natural internucleotide linkages. Expressible RNA polynucleotides for delivering an encoded therapeutic polypeptide are described, for example, in Kormann et al., Nat Biotechnol. 29:154-7, 2011; and U.S. Application Nos. 2015/0111248; 2014/0243399; 2014/0147454; and 2013/0245104, which are incorporated by reference in their entireties.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (e.g., antibody) in a composition may be defined. For instance, certain compositions may comprise an agent that is at least 80%, 85%, 90%, 91%, 92%, 93%, 94%, 95%, 96%, 97%, 98%, 99%, or 100% pure on a protein basis or a weight-weight basis, including all decimals and ranges in between, as measured, for example and by no means limiting, by high performance liquid chromatography (HPLC), a well-known form of column chromatography used frequently in biochemistry and analytical chemistry to separate, identify, and quantify compounds.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

Certain embodiments include biologically active "variants" and "fragments" of the polypeptides (e.g., antibodies) described herein, and the polynucleotides that encode the same. "Variants" contain one or more substitutions, additions, deletions, and/or insertions relative to a reference polypeptide or polynucleotide (see, e.g., the Tables and the Sequence Listing). A variant polypeptide or polynucleotide comprises an amino acid or nucleotide sequence with at least about 50%, 55%, 60%, 65%, 70%, 75%, 80%, 85%, 90%, 91%, 92%, 93%, 94%, 95%, 96%, 97%, 98%, 99% or more sequence identity or similarity or homology to a reference sequence, as described herein, and substantially retains the activity of that reference sequence. Also included are sequences that consist of or differ from a reference sequences by the addition, deletion, insertion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids or nucleotides and which substantially retain the activity of that reference sequence. In certain embodiments, the additions or deletions include C-terminal and/or N-terminal additions and/or deletions.

The terms "sequence identity" or, for example, comprising a "sequence at least 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (e.g., antibody) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaPO$_4$). In specific embodiments, solubility is measured at relatively lower pH (e.g., pH 6.0) and relatively higher salt (e.g., 500 mM NaCl and 10 mM NaPO$_4$). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents.

As used herein, the terms "therapeutically effective amount", "therapeutic dose," "prophylactically effective amount," or "diagnostically effective amount" is the amount of an agent (e.g., anti-IL-11Rα antibody, immunotherapy agent) needed to elicit the desired biological response following administration.

As used herein, "treatment" of a subject (e.g., a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied mutatis mutandis to every other embodiment unless expressly stated otherwise.

Anti-IL-11Rα Antibodies

Certain embodiments include antibodies, and antigen binding fragments thereof, which bind to interleukin-11 receptor subunit α (IL-11Rα). In some embodiments, an antibody or antigen binding fragment thereof modulates (e.g., interferes with, antagonizes, inhibits) binding of IL-11Rα to its ligand, interleukin 11 (IL-11). In certain embodiments, an antibody or antigen binding fragment thereof is characterized by or comprises a heavy chain variable region ($V_H$) that comprises complementary determining region $V_H$CDR1, $V_H$CDR2, and $V_H$CDR3 sequences, and a light chain variable region ($V_L$) that comprises complementary determining region $V_L$CDR1, $V_L$CDR2, and $V_L$CDR3 sequences. Exemplary $V_H$ $V_H$CDR1, $V_H$CDR2, $V_H$CDR3, $V_L$, $V_L$CDR1, $V_L$CDR2, and $V_L$CDR3 sequences are provided in Table A1 and Table A2 below.

TABLE A1

Exemplary CDR Sequences

| Description | Sequence | SEQ ID NO: |
|---|---|---|
| mAb1 | | |
| $V_H$CDR1 | WYSMT | 1 |
| $V_H$CDR2 | SIVPSGGHTQYADSVKG | 2 |
| $V_H$CDR3 | GPDWGSFDL | 3 |
| $V_L$CDR1 | QASQDINNYLN | 4 |
| $V_L$CDR2 | DASNLQT | 5 |
| $V_L$CDR3 | QQHESQSPT | 6 |
| mAb2 | | |
| $V_H$CDR1 | WYSMT | 7 |
| $V_H$CDR2 | SIVPSGGHTQYADSVKG | 8 |
| $V_H$CDR3 | GPDWGSFDL | 9 |
| $V_L$CDR1 | QASQDINNYLN | 10 |
| $V_L$CDR2 | DASNLQT | 11 |
| $V_L$CDR3 | QQHEFQSPT | 12 |
| mAb3 | | |
| $V_H$CDR1 | WYSMT | 13 |
| $V_H$CDR2 | SIVPYGDLTQYADSVKG | 14 |
| $V_H$CDR3 | GPDWGSFDL | 15 |
| $V_L$CDR1 | QASQDINNYLN | 16 |
| $V_L$CDR2 | DASNLQT | 17 |
| $V_L$CDR3 | QQHESQSPT | 18 |
| mAb4 | | |
| $V_H$CDR1 | WYSMT | 19 |
| $V_H$CDR2 | SIVPYGDLTQYADSVKG | 20 |
| $V_H$CDR3 | GPDWGSFDL | 21 |
| $V_L$CDR1 | QASQDINNYLN | 22 |
| $V_L$CDR2 | DASNLQT | 23 |
| $V_L$CDR3 | QQHEFQSPT | 24 |
| mAb5 | | |
| $V_H$CDR1 | WYSMT | 25 |
| $V_H$CDR2 | SIVPYGDLTQYADSVKG | 26 |
| $V_H$CDR3 | GPGWGSFDL | 27 |
| $V_L$CDR1 | QASQDINNYLN | 28 |
| $V_L$CDR2 | DASNLQT | 29 |
| $V_L$CDR3 | QQHESQSPT | 30 |
| mAb6 | | |
| $V_H$CDR1 | WYSMT | 31 |
| $V_H$CDR2 | SIVPYGDLTQYADSVKG | 32 |
| $V_H$CDR3 | GPGWGSFDL | 33 |
| $V_L$CDR1 | QASQDINNYLN | 34 |
| $V_L$CDR2 | DASNLQT | 35 |
| $V_L$CDR3 | QQHEFQSPT | 36 |
| mAb7 | | |
| $V_H$CDR1 | NYAMS | 37 |
| $V_H$CDR2 | SIVPYGDLTQYADSVKG | 38 |
| $V_H$CDR3 | GPGWGSFDL | 39 |
| $V_L$CDR1 | QASQDINNYLN | 40 |
| $V_L$CDR2 | DASNLQT | 41 |
| $V_L$CDR3 | QQHESQSPT | 42 |
| mAb8 | | |
| $V_H$CDR1 | SYAMS | 43 |
| $V_H$CDR2 | SIVPYGDLTQYADSVKG | 44 |
| $V_H$CDR3 | GPGWGSFDL | 45 |
| $V_L$CDR1 | QASQDINNYLN | 46 |
| $V_L$CDR2 | DASNLQT | 47 |
| $V_L$CDR3 | QQHESQSPT | 48 |
| mAb9 | | |
| $V_H$CDR1 | WYSMT | 49 |
| $V_H$CDR2 | GIVPYGDLTQYADSVKG | 50 |
| $V_H$CDR3 | GPGWGSFDL | 51 |
| $V_L$CDR1 | QASQDINNYLN | 52 |
| $V_L$CDR2 | DASNLQT | 53 |
| $V_L$CDR3 | QQHESQSPT | 54 |
| mAb10 | | |
| $V_H$CDR1 | WYSMT | 55 |
| $V_H$CDR2 | SIVAYGDLTQYADSVKG | 56 |
| $V_H$CDR3 | GPGWGSFDL | 57 |
| $V_L$CDR1 | QASQDINNYLN | 58 |
| $V_L$CDR2 | DASNLQT | 59 |
| $V_L$CDR3 | QQHESQSPT | 60 |
| mAb11 | | |
| $V_H$CDR1 | WYSMT | 61 |
| $V_H$CDR2 | SIVDYGDLTQYADSVKG | 62 |
| $V_H$CDR3 | GPGWGSFDL | 63 |
| $V_L$CDR1 | QASQDINNYLN | 64 |
| $V_L$CDR2 | DASNLQT | 65 |
| $V_L$CDR3 | QQHESQSPT | 66 |
| mAb12 | | |
| $V_H$CDR1 | WYSMT | 67 |
| $V_H$CDR2 | SIVPYGDLTQYADSVKG | 68 |
| $V_H$CDR3 | GPGWYSFDL | 69 |
| $V_L$CDR1 | QASQDINNYLN | 70 |
| $V_L$CDR2 | DASNLQT | 71 |
| $V_L$CDR3 | QQHESQSPT | 72 |
| mAb13 | | |
| $V_H$CDR1 | WYSMT | 73 |
| $V_H$CDR2 | SIVPYGDLTQYADSVKG | 74 |
| $V_H$CDR3 | PEDWGRFDL | 75 |
| $V_L$CDR1 | QASQDINNYLN | 76 |
| $V_L$CDR2 | DASNLQT | 77 |
| $V_L$CDR3 | QQHESQSPT | 78 |
| mAb14 | | |
| $V_H$CDR1 | WYSMT | 79 |
| $V_H$CDR2 | SIVPYGDLTQYAESVKG | 80 |
| $V_H$CDR3 | GPGWGSFDL | 81 |
| $V_L$CDR1 | QASQDINNYLN | 82 |
| $V_L$CDR2 | DASNLQT | 83 |
| $V_L$CDR3 | QQHESQSPT | 84 |
| mAb15 | | |
| $V_H$CDR1 | WYSMT | 85 |
| $V_H$CDR2 | SIVPYGDLTQYADSVKG | 86 |
| $V_H$CDR3 | GPGWGSFDL | 87 |
| $V_L$CDR1 | QASQDINNYLN | 88 |
| $V_L$CDR2 | DASNLQT | 89 |
| $V_L$CDR3 | QQHETQTPT | 90 |
| mAb16 | | |
| $V_H$CDR1 | AYSMT | 91 |
| $V_H$CDR2 | SIVPYGDLTQYADSVKG | 92 |
| $V_H$CDR3 | GPGWGSFDL | 93 |
| $V_L$CDR1 | QASQDINNYLN | 94 |
| $V_L$CDR2 | DASNLQT | 95 |
| $V_L$CDR3 | QQHESQSPT | 96 |
| mAb17 | | |
| $V_H$CDR1 | DYSMT | 97 |
| $V_H$CDR2 | SIVPYGDLTQYADSVKG | 98 |
| $V_H$CDR3 | GPGWGSFDL | 99 |
| $V_L$CDR1 | QASQDINNYLN | 100 |
| $V_L$CDR2 | DASNLQT | 101 |
| $V_L$CDR3 | QQHESQSPT | 102 |

TABLE A1-continued

Exemplary CDR Sequences

| Description | Sequence | SEQ ID NO: |
|---|---|---|
| mAb18 | | |
| V$_H$CDR1 | EYSMT | 103 |
| V$_H$CDR2 | SIVPYGDLTQYADSVKG | 104 |
| V$_H$CDR3 | GPGWGSFDL | 105 |
| V$_L$CDR1 | QASQDINNYLN | 106 |
| V$_L$CDR2 | DASNLQT | 107 |
| V$_L$CDR3 | QQHESQSPT | 108 |
| mAb19 | | |
| V$_H$CDR1 | FYSMT | 109 |
| V$_H$CDR2 | SIVPYGDLTQYADSVKG | 110 |
| V$_H$CDR3 | GPGWGSFDL | 111 |
| V$_L$CDR1 | QASQDINNYLN | 112 |
| V$_L$CDR2 | DASNLQT | 113 |
| V$_L$CDR3 | QQHESQSPT | 114 |
| mAb20 | | |
| V$_H$CDR1 | GYSMT | 115 |
| V$_H$CDR2 | SIVPYGDLTQYADSVKG | 116 |
| V$_H$CDR3 | GPGWGSFDL | 117 |
| V$_L$CDR1 | QASQDINNYLN | 118 |
| V$_L$CDR2 | DASNLQT | 119 |
| V$_L$CDR3 | QQHESQSPT | 120 |
| mAb21 | | |
| V$_H$CDR1 | HYSMT | 121 |
| V$_H$CDR2 | SIVPYGDLTQYADSVKG | 122 |
| V$_H$CDR3 | GPGWGSFDL | 123 |
| V$_L$CDR1 | QASQDINNYLN | 124 |
| V$_L$CDR2 | DASNLQT | 125 |
| V$_L$CDR3 | QQHESQSPT | 126 |
| mAb22 | | |
| V$_H$CDR1 | IYSMT | 127 |
| V$_H$CDR2 | SIVPYGDLTQYADSVKG | 128 |
| V$_H$CDR3 | GPGWGSFDL | 129 |
| V$_L$CDR1 | QASQDINNYLN | 130 |
| V$_L$CDR2 | DASNLQT | 131 |
| V$_L$CDR3 | QQHESQSPT | 132 |
| mAb23 | | |
| V$_H$CDR1 | KYSMT | 133 |
| V$_H$CDR2 | SIVPYGDLTQYADSVKG | 134 |
| V$_H$CDR3 | GPGWGSFDL | 135 |
| V$_L$CDR1 | QASQDINNYLN | 136 |
| V$_L$CDR2 | DASNLQT | 137 |
| V$_L$CDR3 | QQHESQSPT | 138 |
| mAb24 | | |
| V$_H$CDR1 | LYSMT | 139 |
| V$_H$CDR2 | SIVPYGDLTQYADSVKG | 140 |
| V$_H$CDR3 | GPGWGSFDL | 141 |
| V$_L$CDR1 | QASQDINNYLN | 142 |
| V$_L$CDR2 | DASNLQT | 143 |
| V$_L$CDR3 | QQHESQSPT | 144 |
| mAb25 | | |
| V$_H$CDR1 | MYSMT | 145 |
| V$_H$CDR2 | SIVPYGDLTQYADSVKG | 146 |
| V$_H$CDR3 | GPGWGSFDL | 147 |
| V$_L$CDR1 | QASQDINNYLN | 148 |
| V$_L$CDR2 | DASNLQT | 149 |
| V$_L$CDR3 | QQHESQSPT | 150 |
| mAb26 | | |
| V$_H$CDR1 | NYSMT | 151 |
| V$_H$CDR2 | SIVPYGDLTQYADSVKG | 152 |

TABLE A1-continued

Exemplary CDR Sequences

| Description | Sequence | SEQ ID NO: |
|---|---|---|
| V$_H$CDR3 | GPGWGSFDL | 153 |
| V$_L$CDR1 | QASQDINNYLN | 154 |
| V$_L$CDR2 | DASNLQT | 155 |
| V$_L$CDR3 | QQHESQSPT | 156 |
| mAb27 | | |
| V$_H$CDR1 | PYSMT | 157 |
| V$_H$CDR2 | SIVPYGDLTQYADSVKG | 158 |
| V$_H$CDR3 | GPGWGSFDL | 159 |
| V$_L$CDR1 | QASQDINNYLN | 160 |
| V$_L$CDR2 | DASNLQT | 161 |
| V$_L$CDR3 | QQHESQSPT | 162 |
| mAb28 | | |
| V$_H$CDR1 | RYSMT | 163 |
| V$_H$CDR2 | SIVPYGDLTQYADSVKG | 164 |
| V$_H$CDR3 | GPGWGSFDL | 165 |
| V$_L$CDR1 | QASQDINNYLN | 166 |
| V$_L$CDR2 | DASNLQT | 167 |
| V$_L$CDR3 | QQHESQSPT | 168 |
| mAb29 | | |
| V$_H$CDR1 | SYSMT | 169 |
| V$_H$CDR2 | SIVPYGDLTQYADSVKG | 170 |
| V$_H$CDR3 | GPGWGSFDL | 171 |
| V$_L$CDR1 | QASQDINNYLN | 172 |
| V$_L$CDR2 | DASNLQT | 173 |
| V$_L$CDR3 | QQHESQSPT | 174 |
| mAb30 | | |
| V$_H$CDR1 | TYSMT | 175 |
| V$_H$CDR2 | SIVPYGDLTQYADSVKG | 176 |
| V$_H$CDR3 | GPGWGSFDL | 177 |
| V$_L$CDR1 | QASQDINNYLN | 178 |
| V$_L$CDR2 | DASNLQT | 179 |
| V$_L$CDR3 | QQHESQSPT | 180 |
| mAb31 | | |
| V$_H$CDR1 | VYSMT | 181 |
| V$_H$CDR2 | SIVPYGDLTQYADSVKG | 182 |
| V$_H$CDR3 | GPGWGSFDL | 183 |
| V$_L$CDR1 | QASQDINNYLN | 184 |
| V$_L$CDR2 | DASNLQT | 185 |
| V$_L$CDR3 | QQHESQSPT | 186 |
| mAb32 | | |
| V$_H$CDR1 | YYSMT | 187 |
| V$_H$CDR2 | SIVPYGDLTQYADSVKG | 188 |
| V$_H$CDR3 | GPGWGSFDL | 189 |
| V$_L$CDR1 | QASQDINNYL | 190 |
| V$_L$CDR2 | DASNLQT | 191 |
| V$_L$CDR3 | QQHESQSPT | 192 |

Thus, in certain embodiments, an antibody or antigen binding fragment thereof comprises a V$_H$ sequence that comprises complementary determining region V$_H$CDR1, V$_H$CDR2, and V$_H$CDR3 sequences selected from Table A1 and variants thereof which bind to IL-11Rα; and a V$_L$ sequence that comprises complementary determining region V$_L$CDR1, V$_L$CDR2, and V$_L$CDR3 sequences selected from Table A1 and variants thereof which bind to IL-11Rα.

In certain embodiments, the CDR sequences are as follows:

the $V_H$CDR1, $V_H$CDR2, and $V_H$CDR3 sequences comprise SEQ ID NOs: 1-3, respectively, and the $V_L$CDR1, $V_L$CDR2, and $V_L$CDR3 sequences comprise SEQ ID NOs: 4-6, respectively;

the $V_H$CDR1, $V_H$CDR2, and $V_H$CDR3 sequences comprise SEQ ID NOs: 7-9, respectively, and the $V_L$CDR1, $V_L$CDR2, and $V_L$CDR3 sequences comprise SEQ ID NOs: 10-12, respectively;

the $V_H$CDR1, $V_H$CDR2, and $V_H$CDR3 sequences comprise SEQ ID NOs: 13-15, respectively, and the $V_L$CDR1, $V_L$CDR2, and $V_L$CDR3 sequences comprise SEQ ID NOs: 16-18, respectively;

the $V_H$CDR1, $V_H$CDR2, and $V_H$CDR3 sequences comprise SEQ ID NOs: 19-21, respectively, and the $V_L$CDR1, $V_L$CDR2, and $V_L$CDR3 sequences comprise SEQ ID NOs: 22-24, respectively;

the $V_H$CDR1, $V_H$CDR2, and $V_H$CDR3 sequences comprise SEQ ID NOs: 25-27, respectively, and the $V_L$CDR1, $V_L$CDR2, and $V_L$CDR3 sequences comprise SEQ ID NOs: 28-30, respectively;

the $V_H$CDR1, $V_H$CDR2, and $V_H$CDR3 sequences comprise SEQ ID NOs: 31-33, respectively, and the $V_L$CDR1, $V_L$CDR2, and $V_L$CDR3 sequences comprise SEQ ID NOs: 34-36, respectively;

the $V_H$CDR1, $V_H$CDR2, and $V_H$CDR3 sequences comprise SEQ ID NOs: 37-39, respectively, and the $V_L$CDR1, $V_L$CDR2, and $V_L$CDR3 sequences comprise SEQ ID NOs: 40-42, respectively;

the $V_H$CDR1, $V_H$CDR2, and $V_H$CDR3 sequences comprise SEQ ID NOs: 43-45, respectively, and the $V_L$CDR1, $V_L$CDR2, and $V_L$CDR3 sequences comprise SEQ ID NOs: 46-48, respectively;

the $V_H$CDR1, $V_H$CDR2, and $V_H$CDR3 sequences comprise SEQ ID NOs: 49-51, respectively, and the $V_L$CDR1, $V_L$CDR2, and $V_L$CDR3 sequences comprise SEQ ID NOs: 52-54, respectively;

the $V_H$CDR1, $V_H$CDR2, and $V_H$CDR3 sequences comprise SEQ ID NOs: 55-57, respectively, and the $V_L$CDR1, $V_L$CDR2, and $V_L$CDR3 sequences comprise SEQ ID NOs: 58-60, respectively;

the $V_H$CDR1, $V_H$CDR2, and $V_H$CDR3 sequences comprise SEQ ID NOs: 61-63, respectively, and the $V_L$CDR1, $V_L$CDR2, and $V_L$CDR3 sequences comprise SEQ ID NOs: 64-66, respectively;

the $V_H$CDR1, $V_H$CDR2, and $V_H$CDR3 sequences comprise SEQ ID NOs: 67-69, respectively, and the $V_L$CDR1, $V_L$CDR2, and $V_L$CDR3 sequences comprise SEQ ID NOs: 70-72, respectively;

the $V_H$CDR1, $V_H$CDR2, and $V_H$CDR3 sequences comprise SEQ ID NOs: 73-75, respectively, and the $V_L$CDR1, $V_L$CDR2, and $V_L$CDR3 sequences comprise SEQ ID NOs: 76-78, respectively;

the $V_H$CDR1, $V_H$CDR2, and $V_H$CDR3 sequences comprise SEQ ID NOs: 79-81, respectively, and the $V_L$CDR1, $V_L$CDR2, and $V_L$CDR3 sequences comprise SEQ ID NOs: 82-84, respectively;

the $V_H$CDR1, $V_H$CDR2, and $V_H$CDR3 sequences comprise SEQ ID NOs: 85-87, respectively, and the $V_L$CDR1, $V_L$CDR2, and $V_L$CDR3 sequences comprise SEQ ID NOs: 88-90, respectively;

the $V_H$CDR1, $V_H$CDR2, and $V_H$CDR3 sequences comprise SEQ ID NOs: 91-93, respectively, and the $V_L$CDR1, $V_L$CDR2, and $V_L$CDR3 sequences comprise SEQ ID NOs: 94-96, respectively;

the $V_H$CDR1, $V_H$CDR2, and $V_H$CDR3 sequences comprise SEQ ID NOs: 97-99, respectively, and the $V_L$CDR1, $V_L$CDR2, and $V_L$CDR3 sequences comprise SEQ ID NOs: 100-102, respectively;

the $V_H$CDR1, $V_H$CDR2, and $V_H$CDR3 sequences comprise SEQ ID NOs: 103-105, respectively, and the $V_L$CDR1, $V_L$CDR2, and $V_L$CDR3 sequences comprise SEQ ID NOs: 106-108, respectively;

the $V_H$CDR1, $V_H$CDR2, and $V_H$CDR3 sequences comprise SEQ ID NOs: 109-111, respectively, and the $V_L$CDR1, $V_L$CDR2, and $V_L$CDR3 sequences comprise SEQ ID NOs: 112-114, respectively;

the $V_H$CDR1, $V_H$CDR2, and $V_H$CDR3 sequences comprise SEQ ID NOs: 115-117, respectively, and the $V_L$CDR1, $V_L$CDR2, and $V_L$CDR3 sequences comprise SEQ ID NOs: 118-120, respectively;

the $V_H$CDR1, $V_H$CDR2, and $V_H$CDR3 sequences comprise SEQ ID NOs: 121-123, respectively, and the $V_L$CDR1, $V_L$CDR2, and $V_L$CDR3 sequences comprise SEQ ID NOs: 124-126, respectively;

the $V_H$CDR1, $V_H$CDR2, and $V_H$CDR3 sequences comprise SEQ ID NOs: 127-129, respectively, and the $V_L$CDR1, $V_L$CDR2, and $V_L$CDR3 sequences comprise SEQ ID NOs: 130-132, respectively;

the $V_H$CDR1, $V_H$CDR2, and $V_H$CDR3 sequences comprise SEQ ID NOs: 133-135, respectively, and the $V_L$CDR1, $V_L$CDR2, and $V_L$CDR3 sequences comprise SEQ ID NOs: 136-138, respectively;

the $V_H$CDR1, $V_H$CDR2, and $V_H$CDR3 sequences comprise SEQ ID NOs: 139-141, respectively, and the $V_L$CDR1, $V_L$CDR2, and $V_L$CDR3 sequences comprise SEQ ID NOs: 142-144, respectively;

the $V_H$CDR1, $V_H$CDR2, and $V_H$CDR3 sequences comprise SEQ ID NOs: 145-147, respectively, and the $V_L$CDR1, $V_L$CDR2, and $V_L$CDR3 sequences comprise SEQ ID NOs: 148-150, respectively;

the $V_H$CDR1, $V_H$CDR2, and $V_H$CDR3 sequences comprise SEQ ID NOs: 151-153, respectively, and the $V_L$CDR1, $V_L$CDR2, and $V_L$CDR3 sequences comprise SEQ ID NOs: 154-156, respectively;

the $V_H$CDR1, $V_H$CDR2, and $V_H$CDR3 sequences comprise SEQ ID NOs: 157-159, respectively, and the $V_L$CDR1, $V_L$CDR2, and $V_L$CDR3 sequences comprise SEQ ID NOs: 160-162, respectively;

the $V_H$CDR1, $V_H$CDR2, and $V_H$CDR3 sequences comprise SEQ ID NOs: 163-165, respectively, and the $V_L$CDR1, $V_L$CDR2, and $V_L$CDR3 sequences comprise SEQ ID NOs: 166-168, respectively;

the $V_H$CDR1, $V_H$CDR2, and $V_H$CDR3 sequences comprise SEQ ID NOs: 169-171, respectively, and the $V_L$CDR1, $V_L$CDR2, and $V_L$CDR3 sequences comprise SEQ ID NOs: 172-174, respectively;

the $V_H$CDR1, $V_H$CDR2, and $V_H$CDR3 sequences comprise SEQ ID NOs: 175-177, respectively, and the $V_L$CDR1, $V_L$CDR2, and $V_L$CDR3 sequences comprise SEQ ID NOs: 178-180, respectively;

the $V_H$CDR1, $V_H$CDR2, and $V_H$CDR3 sequences comprise SEQ ID NOs: 181-183, respectively, and the $V_L$CDR1, $V_L$CDR2, and $V_L$CDR3 sequences comprise SEQ ID NOs: 184-186, respectively; or the $V_H$CDR1, $V_H$CDR2, and $V_H$CDR3 sequences comprise SEQ ID NOs: 187-189, respectively, and the $V_L$CDR1, $V_L$CDR2, and $V_L$CDR3 sequences comprise SEQ ID NOs: 190-192, respectively.

Also included are minor variants the foregoing CDRs. Exemplary variants bind to IL-11Rα and have 1, 2, or 3 total alterations in any one or more of the individual CDRs, for example, any one or more the $V_H$CDR1, $V_H$CDR2, $V_H$CDR3, $V_L$CDR1, $V_L$CDR2, and/or $V_L$CDR3 sequences described herein. Exemplary "alterations" include amino acid substitutions, additions, and deletions.

Exemplary $V_H$ and $V_L$ sequences are provided in Table A2 below.

TABLE A2

Exemplary Polypeptide Sequences

| Description | Sequence | SEQ ID NO: |
|---|---|---|
| mAb1 | | |
| Heavy chain variable region ($V_H$) | EVQLLESGGGLVQPGGSLRLSCAASGFTFSWYSMTWVRQAPGKGLEWVS SIVPSGGHTQYADSVKGRFTISRDNSKNTLYLQMNSLRAEDTAVYYCAK GPDWGSFDLWGRGTLVTVSS | 193 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 194 |
| mAb2 | | |
| Heavy chain variable region ($V_H$) | EVQLLESGGGLVQPGGSLRLSCAASGFTFSWYSMTWVRQAPGKGLEWVS SIVPSGGHTQYADSVKGRFTISRDNSKNTLYLQMNSLRAEDTAVYYCAK GPDWGSFDLWGRGTLVTVSS | 195 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHEFQSPTF GPGTKVDIK | 196 |
| mAb3 | | |
| Heavy chain variable region ($V_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK GPDWGSFDLWGRGTLVTVSS | 197 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 198 |
| mAb4 | | |
| Heavy chain variable region ($V_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK GPDWGSFDLWGRGTLVTVSS | 199 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHEFQSPTF GPGTKVDIK | 200 |
| mAb5 | | |
| Heavy chain variable region ($V_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK GPGWGSFDLWGRGTLVTVSS | 201 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 202 |
| mAb6 | | |
| Heavy chain variable region ($V_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK GPGWGSFDLWGRGTLVTVSS | 203 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHEFQSPTF GPGTKVDIK | 204 |
| mAb7 | | |
| Heavy chain variable region ($V_H$) | EVQLLESGGGLVQPGGSLRLSCAASGFTFSNYAMSWVRQAPGKGLEWVS SIVPYGDLTQYADSVKGRFTISRDNSKNTLYLQMNSLRAEDTAVYYCAK GPGWGSFDLWGRGTLVTVSS | 205 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 206 |
| mAb8 | | |
| Heavy chain variable region ($V_H$) | EVQLLESGGGLVQPGGSLRLSCAASGFTFSSYAMSWVRQAPGKGLEWVS SIVPYGDLTQYADSVKGRFTISRDNSKNTLYLQMNSLRAEDTAVYYCAK GPGWGSFDLWGRGTLVTVSS | 207 |
| Light chain variable region ($V_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 208 |

TABLE A2-continued

Exemplary Polypeptide Sequences

| Description | Sequence | SEQ ID NO: |
|---|---|---|
| mAb9 | | |
| Heavy chain variable region (V$_H$) | EVQLLESGGGLVQPGGSLRLSCAASGFTFSWYSMTWVRQAPGKGLEWVS GIVPYGDLTQYADSVKGRFTISRDNSKNTLYLQMNSLRAEDTAVYYCAK GPGWGSFDLWGRGTLVTSS | 209 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 210 |
| mAb10 | | |
| Heavy chain variable region (V$_H$) | EVQLLESGGGLVQPGGSLRLSCAASGFTFSWYSMTWVRQAPGKGLEWVS SIVAYGDLTQYADSVKGRFTISRDNSKNTLYLQMNSLRAEDTAVYYCAK GPGWGSFDLWGRGTLVTSS | 211 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 212 |
| mAb11 | | |
| Heavy chain variable region (V$_H$) | EVQLLESGGGLVQPGGSLRLSCAASGFTFSWYSMTWVRQAPGKGLEWVS SIVDYGDLTQYADSVKGRFTISRDNSKNTLYLQMNSLRAEDTAVYYCAK GPGWGSFDLWGRGTLVTSS | 213 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 214 |
| mAb12 | | |
| Heavy chain variable region (V$_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK GPGWYSFDLWGRGTLVTSS | 215 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 216 |
| mAb13 | | |
| Heavy chain variable region (V$_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK PEDWGRFDLWGRGTLVTSS | 217 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 218 |
| mAb14 | | |
| Heavy chain variable region (V$_H$) | EVQLLESGGGLVQPGGSLRLSCAASGFTFSWYSMTWVRQAPGKGLEWVS SIVPYGDLTQYAESVKGRFTISRDNSKNTLYLQMNSLRAEDTAVYYCAK GPGWGSFDLWGRGTLVTSS | 219 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 220 |
| mAb15 | | |
| Heavy chain variable region (V$_H$) | EVQLLESGGGLVQPGGSLRLSCAASGFTFSWYSMTWVRQAPGKGLEWVS SIVPYGDLTQYADSVKGRFTISRDNSKNTLYLQMNSLRAEDTAVYYCAK GPGWGSFDLWGRGTLVTSS | 221 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHETQTPTF GPGTKVDIK | 222 |
| mAb16 | | |
| Heavy chain variable region (V$_H$) | EVQLLESGGGLVQPGGSLRLSCAASGFTFSAYSMTWVRQAPGKGLEWVS SIVPYGDLTQYADSVKGRFTISRDNSKNTLYLQMNSLRAEDTAVYYCAK GPGWGSFDLWGRGTLVTSS | 223 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 224 |

TABLE A2-continued

Exemplary Polypeptide Sequences

| Description | Sequence | SEQ ID NO: |
|---|---|---|
| mAb17 | | |
| Heavy chain variable region (V$_H$) | EVQLLESGGGLVQPGGSLRLSCAASGFTFSDYSMTWVRQAPGKGLEWVS SIVPYGDLTQYADSVKGRFTISRDNSKNTLYLQMNSLRAEDTAVYYCAK GPGWGSFDLWGRGTLVTSS | 225 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 226 |
| mAb18 | | |
| Heavy chain variable region (V$_H$) | EVQLLESGGGLVQPGGSLRLSCAASGFTFSEYSMTWVRQAPGKGLEWVS SIVPYGDLTQYADSVKGRFTISRDNSKNTLYLQMNSLRAEDTAVYYCAK GPGWGSFDLWGRGTLVTSS | 227 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 228 |
| mAb19 | | |
| Heavy chain variable region (V$_H$) | EVQLLESGGGLVQPGGSLRLSCAASGFTFSFYSMTWVRQAPGKGLEWVS SIVPYGDLTQYADSVKGRFTISRDNSKNTLYLQMNSLRAEDTAVYYCAK GPGWGSFDLWGRGTLVTSS | 229 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 230 |
| mAb20 | | |
| Heavy chain variable region (V$_H$) | EVQLLESGGGLVQPGGSLRLSCAASGFTFSGYSMTWVRQAPGKGLEWVS SIVPYGDLTQYADSVKGRFTISRDNSKNTLYLQMNSLRAEDTAVYYCAK GPGWGSFDLWGRGTLVTSS | 231 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 232 |
| mAb21 | | |
| Heavy chain variable region (V$_H$) | EVQLLESGGGLVQPGGSLRLSCAASGFTFSHYSMTWVRQAPGKGLEWVS SIVPYGDLTQYADSVKGRFTISRDNSKNTLYLQMNSLRAEDTAVYYCAK GPGWGSFDLWGRGTLVTSS | 233 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 234 |
| mAb22 | | |
| Heavy chain variable region (V$_H$) | EVQLLESGGGLVQPGGSLRLSCAASGFTFSIYSMTWVRQAPGKGLEWVS SIVPYGDLTQYADSVKGRFTISRDNSKNTLYLQMNSLRAEDTAVYYCAK GPGWGSFDLWGRGTLVTSS | 235 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 236 |
| mAb23 | | |
| Heavy chain variable region (V$_H$) | EVQLLESGGGLVQPGGSLRLSCAASGFTFSKYSMTWVRQAPGKGLEWVS SIVPYGDLTQYADSVKGRFTISRDNSKNTLYLQMNSLRAEDTAVYYCAK GPGWGSFDLWGRGTLVTSS | 237 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 238 |
| mAb24 | | |
| Heavy chain variable region (V$_H$) | EVQLLESGGGLVQPGGSLRLSCAASGFTFSLYSMTWVRQAPGKGLEWVS SIVPYGDLTQYADSVKGRFTISRDNSKNTLYLQMNSLRAEDTAVYYCAK GPGWGSFDLWGRGTLVTSS | 239 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 240 |

TABLE A2-continued

Exemplary Polypeptide Sequences

| Description | Sequence | SEQ ID NO: |
|---|---|---| mAb25

| Heavy chain variable region (V$_H$) | EVQLLESGGGLVQPGGSLRLSCAASGFTFSMYSMTWVRQAPGKGLEWVS SIVPYGDLTQYADSVKGRFTISRDNSKNTLYLQMNSLRAEDTAVYYCAK GPGWGSFDLWGRGTLVTVSS | 241 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTE GPGTKVDIK | 242 | mAb26

| Heavy chain variable region (V$_H$) | EVQLLESGGGLVQPGGSLRLSCAASGFTFSNYSMTWVRQAPGKGLEWVS SIVPYGDLTQYADSVKGRFTISRDNSKNTLYLQMNSLRAEDTAVYYCAK GPGWGSFDLWGRGTLVTVSS | 243 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 244 | mAb27

| Heavy chain variable region (V$_H$) | EVQLLESGGGLVQPGGSLRLSCAASGFTFSPYSMTWVRQAPGKGLEWVS SIVPYGDLTQYADSVKGRFTISRDNSKNTLYLQMNSLRAEDTAVYYCAK GPGWGSFDLWGRGTLVTVSS | 245 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 246 | mAb28

| Heavy chain variable region (V$_H$) | EVQLLESGGGLVQPGGSLRLSCAASGFTFSRYSMTWVRQAPGKGLEWVS SIVPYGDLTQYADSVKGRFTISRDNSKNTLYLQMNSLRAEDTAVYYCAK GPGWGSFDLWGRGTLVTVSS | 247 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 248 | mAb29

| Heavy chain variable region (V$_H$) | EVQLLESGGGLVQPGGSLRLSCAASGFTFSSYSMTWVRQAPGKGLEWVS SIVPYGDLTQYADSVKGRFTISRDNSKNTLYLQMNSLRAEDTAVYYCAK GPGWGSFDLWGRGTLVTVSS | 249 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 250 | mAb30

| Heavy chain variable region (V$_H$) | EVQLLESGGGLVQPGGSLRLSCAASGFTFSTYSMTWVRQAPGKGLEWVS SIVPYGDLTQYADSVKGRFTISRDNSKNTLYLQMNSLRAEDTAVYYCAK GPGWGSFDLWGRGTLVTVSS | 251 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 252 | mAb31

| Heavy chain variable region (V$_H$) | EVQLLESGGGLVQPGGSLRLSCAASGFTFSVYSMTWVRQAPGKGLEWVS SIVPYGDLTQYADSVKGRFTISRDNSKNTLYLQMNSLRAEDTAVYYCAK GPGWGSFDLWGRGTLVTVSS | 253 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 254 | mAb32

| Heavy chain variable region (V$_H$) | EVQLLESGGGLVQPGGSLRLSCAASGFTFSYYSMTWVRQAPGKGLEWVS SIVPYGDLTQYADSVKGRFTISRDNSKNTLYLQMNSLRAEDTAVYYCAK GPGWGSFDLWGRGTLVTVSS | 255 |
| Light chain variable region (V$_L$) | DIQMTQSPSSLSASVGDRVTITCQASQDINNYLNWYQQKPGKAPKLLIY DASNLQTGVPSRFSGSGSGTDFTFTISSLQPEDIATYYCQQHESQSPTF GPGTKVDIK | 256 |

Thus, in certain embodiments, an antibody, or antigen binding fragment thereof, binds to IL-11Rα and comprises a V$_H$ sequence and a corresponding V$_L$ sequence selected from Table A2. In certain embodiments, the V$_H$ comprises a sequence least 80, 85, 90, 95, 97, 98, 99, or 100% identical to a sequence selected from Table A2, including, for example, wherein the V$_H$ has 1, 2, 3, 4, 5, 6, 7, 8, 9, or 10 alterations in one or more framework regions. In some embodiments, the V$_L$ comprises a sequence at least 80, 85, 90, 95, 97, 98, 99, or 100% identical to a sequence selected from Table A2, including, for example, wherein the V$_L$ has 1, 2, 3, 4, 5, 6, 7, 8, 9, or 10 alterations in one or more framework regions.

In some embodiments, the V$_H$ and V$_L$ of an antibody or antigen binding fragment are as follows:

the V$_H$ comprises a sequence at least 80, 85, 90, 95, 97, 98, 99, or 100% identical to SEQ ID NO: 193, and the V$_L$ comprises a sequence at least 80, 85, 90, 95, 97, 98, 99, or 100% identical to SEQ ID NO: 194;

the V$_H$ comprises a sequence at least 80, 85, 90, 95, 97, 98, 99, or 100% identical to SEQ ID NO: 195, and the V$_L$ comprises a sequence at least 80, 85, 90, 95, 97, 98, 99, or 100% identical to SEQ ID NO: 196;

the V$_H$ comprises a sequence at least 80, 85, 90, 95, 97, 98, 99, or 100% identical to SEQ ID NO: 197, and the V$_L$ comprises a sequence at least 80, 85, 90, 95, 97, 98, 99, or 100% identical to SEQ ID NO: 198;

the V$_H$ comprises a sequence at least 80, 85, 90, 95, 97, 98, 99, or 100% identical to SEQ ID NO: 199, and the V$_L$ comprises a sequence at least 80, 85, 90, 95, 97, 98, 99, or 100% identical to SEQ ID NO: 200;

the V$_H$ comprises a sequence at least 80, 85, 90, 95, 97, 98, 99, or 100% identical to SEQ ID NO: 201, and the V$_L$ comprises a sequence at least 80, 85, 90, 95, 97, 98, 99, or 100% identical to SEQ ID NO: 202;

the V$_H$ comprises a sequence at least 80, 85, 90, 95, 97, 98, 99, or 100% identical to SEQ ID NO: 203, and the V$_L$ comprises a sequence at least 80, 85, 90, 95, 97, 98, 99, or 100% identical to SEQ ID NO: 204;

the V$_H$ comprises a sequence at least 80, 85, 90, 95, 97, 98, 99, or 100% identical to SEQ ID NO: 205, and the V$_L$ comprises a sequence at least 80, 85, 90, 95, 97, 98, 99, or 100% identical to SEQ ID NO: 206;

the V$_H$ comprises a sequence at least 80, 85, 90, 95, 97, 98, 99, or 100% identical to SEQ ID NO: 207, and the V$_L$ comprises a sequence at least 80, 85, 90, 95, 97, 98, 99, or 100% identical to SEQ ID NO: 208;

the V$_H$ comprises a sequence at least 80, 85, 90, 95, 97, 98, 99, or 100% identical to SEQ ID NO: 209, and the V$_L$ comprises a sequence at least 80, 85, 90, 95, 97, 98, 99, or 100% identical to SEQ ID NO: 210;

the V$_H$ comprises a sequence at least 80, 85, 90, 95, 97, 98, 99, or 100% identical to SEQ ID NO: 211, and the V$_L$ comprises a sequence at least 80, 85, 90, 95, 97, 98, 99, or 100% identical to SEQ ID NO: 212;

the V$_H$ comprises a sequence at least 80, 85, 90, 95, 97, 98, 99, or 100% identical to SEQ ID NO: 213, and the V$_L$ comprises a sequence at least 80, 85, 90, 95, 97, 98, 99, or 100% identical to SEQ ID NO: 214;

the V$_H$ comprises a sequence at least 80, 85, 90, 95, 97, 98, 99, or 100% identical to SEQ ID NO: 215, and the V$_L$ comprises a sequence at least 80, 85, 90, 95, 97, 98, 99, or 100% identical to SEQ ID NO: 216;

the V$_H$ comprises a sequence at least 80, 85, 90, 95, 97, 98, 99, or 100% identical to SEQ ID NO: 217, and the V$_L$ comprises a sequence at least 80, 85, 90, 95, 97, 98, 99, or 100% identical to SEQ ID NO: 218;

the V$_H$ comprises a sequence at least 80, 85, 90, 95, 97, 98, 99, or 100% identical to SEQ ID NO: 219, and the V$_L$ comprises a sequence at least 80, 85, 90, 95, 97, 98, 99, or 100% identical to SEQ ID NO: 220;

the V$_H$ comprises a sequence at least 80, 85, 90, 95, 97, 98, 99, or 100% identical to SEQ ID NO: 221, and the V$_L$ comprises a sequence at least 80, 85, 90, 95, 97, 98, 99, or 100% identical to SEQ ID NO: 222;

the V$_H$ comprises a sequence at least 80, 85, 90, 95, 97, 98, 99, or 100% identical to SEQ ID NO: 223, and the V$_L$ comprises a sequence at least 80, 85, 90, 95, 97, 98, 99, or 100% identical to SEQ ID NO: 224;

the V$_H$ comprises a sequence at least 80, 85, 90, 95, 97, 98, 99, or 100% identical to SEQ ID NO: 225, and the V$_L$ comprises a sequence at least 80, 85, 90, 95, 97, 98, 99, or 100% identical to SEQ ID NO: 226;

the V$_H$ comprises a sequence at least 80, 85, 90, 95, 97, 98, 99, or 100% identical to SEQ ID NO: 227, and the V$_L$ comprises a sequence at least 80, 85, 90, 95, 97, 98, 99, or 100% identical to SEQ ID NO: 228;

the V$_H$ comprises a sequence at least 80, 85, 90, 95, 97, 98, 99, or 100% identical to SEQ ID NO: 229, and the V$_L$ comprises a sequence at least 80, 85, 90, 95, 97, 98, 99, or 100% identical to SEQ ID NO: 230;

the V$_H$ comprises a sequence at least 80, 85, 90, 95, 97, 98, 99, or 100% identical to SEQ ID NO: 231, and the V$_L$ comprises a sequence at least 80, 85, 90, 95, 97, 98, 99, or 100% identical to SEQ ID NO: 232;

the V$_H$ comprises a sequence at least 80, 85, 90, 95, 97, 98, 99, or 100% identical to SEQ ID NO: 233, and the V$_L$ comprises a sequence at least 80, 85, 90, 95, 97, 98, 99, or 100% identical to SEQ ID NO: 234;

the V$_H$ comprises a sequence at least 80, 85, 90, 95, 97, 98, 99, or 100% identical to SEQ ID NO: 235, and the V$_L$ comprises a sequence at least 80, 85, 90, 95, 97, 98, 99, or 100% identical to SEQ ID NO: 236;

the V$_H$ comprises a sequence at least 80, 85, 90, 95, 97, 98, 99, or 100% identical to SEQ ID NO: 237, and the V$_L$ comprises a sequence at least 80, 85, 90, 95, 97, 98, 99, or 100% identical to SEQ ID NO: 238;

the V$_H$ comprises a sequence at least 80, 85, 90, 95, 97, 98, 99, or 100% identical to SEQ ID NO: 239, and the V$_L$ comprises a sequence at least 80, 85, 90, 95, 97, 98, 99, or 100% identical to SEQ ID NO: 240;

the V$_H$ comprises a sequence at least 80, 85, 90, 95, 97, 98, 99, or 100% identical to SEQ ID NO: 241, and the V$_L$ comprises a sequence at least 80, 85, 90, 95, 97, 98, 99, or 100% identical to SEQ ID NO: 242;

the V$_H$ comprises a sequence at least 80, 85, 90, 95, 97, 98, 99, or 100% identical to SEQ ID NO: 243, and the V$_L$ comprises a sequence at least 80, 85, 90, 95, 97, 98, 99, or 100% identical to SEQ ID NO: 244;

the V$_H$ comprises a sequence at least 80, 85, 90, 95, 97, 98, 99, or 100% identical to SEQ ID NO: 245, and the V$_L$ comprises a sequence at least 80, 85, 90, 95, 97, 98, 99, or 100% identical to SEQ ID NO: 246;

the V$_H$ comprises a sequence at least 80, 85, 90, 95, 97, 98, 99, or 100% identical to SEQ ID NO: 247, and the V$_L$ comprises a sequence at least 80, 85, 90, 95, 97, 98, 99, or 100% identical to SEQ ID NO: 248;

the V$_H$ comprises a sequence at least 80, 85, 90, 95, 97, 98, 99, or 100% identical to SEQ ID NO: 249, and the V$_L$ comprises a sequence at least 80, 85, 90, 95, 97, 98, 99, or 100% identical to SEQ ID NO: 250;

the V$_H$ comprises a sequence at least 80, 85, 90, 95, 97, 98, 99, or 100% identical to SEQ ID NO: 251, and the V$_L$ comprises a sequence at least 80, 85, 90, 95, 97, 98, 99, or 100% identical to SEQ ID NO: 252;

the V$_H$ comprises a sequence at least 80, 85, 90, 95, 97, 98, 99, or 100% identical to SEQ ID NO: 253, and the V_L comprises a sequence at least 80, 85, 90, 95, 97, 98, 99, or 100% identical to SEQ ID NO: 254; or the V_H comprises a sequence at least 80, 85, 90, 95, 97, 98, 99, or 100% identical to SEQ ID NO: 255, and the V_L comprises a sequence at least 80, 85, 90, 95, 97, 98, 99, or 100% identical to SEQ ID NO: 256.

Also included are variants thereof that bind to IL-Rα, for example, variants having 1, 2, 3, 4, 5, 6, 7, 8, 9, or 10 alterations in one or more framework regions of any one or more of the foregoing V_H and/or V_L sequences. Exemplary "alterations" include amino acid substitutions, additions, and deletions.

As noted above, an antibody or antigen binding fragment thereof, described herein, binds to IL-11Rα, for example, membrane-bound IL-11Rα. In certain embodiments, an antibody or an antigen binding fragment thereof binds to human IL-11Rα, or a region or fragment thereof. The amino acid sequence of human IL-11Rα is provided in Table B1 below.

TABLE B1

Exemplary IL-11Ra Sequences

| Name | Sequence | SEQ ID NO: |
|---|---|---|
| Human IL-11Rx membrane precursor | MSSSCSGLSRVLVAVATALVSASSPCPQAWGPPGVQYGQPGRSVKLCCPG VTAGDPVSWFRDGEPKLLQGPDSGLGHELVLAQADSTDEGTYICQTLDGA LGGTVTLQLGYPPARPVVSCQAADYENFSCTWSPSQISGLPTRYLTSYRK KTVLGADSQRRSPSTGPWPCPQDPLGAARCVVHGAEFWSQYRINVTEVNP LGASTRLLDVSLQSILRPDPPQGLRVESVPGYPRRLRASWTYPASWPCQP HFLLKFRLQYRPAQHPAWSTVEPAGLEEVITDAVAGLPHAVRVSARDFLD AGTWSTWSPEAWGTPSTGTIPKEIPAWGQLHTQPEVEPQVDSPAPPRPSL QPHPRLLDHRDSVEQVAVLASLGILSFLGLVAGALALGLWLRLRRGGKDG SPKPGFLASVIPVDRRPGAPNL | 257 |

Thus, in certain embodiments, an antibody or antigen binding fragment thereof binds to an IL-11Rα sequence in Table B1, for example, a human IL-11Rα sequence. In particular embodiments, an antibody or antigen binding fragment thereof binds to a fibronectin type-III domain in human IL-11Rα, composed, for example, of approximately residues 112-219 of SEQ ID NO: 257.

In some embodiments, an antibody or antigen binding fragment thereof binds to human IL-11Rα with a binding affinity of about 1 pM to about 10 pM to about 500 pM, or about, at least about, or less than about 1, 5, 10, 20, 30, 40, 50, 60, 70, 80, 90, 100, 110, 120, 130, 140, 150, 160, 170, 180, 190, 200, 300, 400, or 500 pM, or optionally with an affinity that ranges from about 1 pM to about 500 pM, about 1 pM to about 400 pM, about 1 pM to about 300 pM, about 1 pM to about 200 pM, about 1 pM to about 100 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 5 pM to about 500 pM, about 5 pM to about 400 pM, about 5 pM to about 300 pM, about 5 pM to about 200 pM, about 5 pM to about 100 pM, about 5 pM to about 50 pM, about 5 pM to about 40 pM, about 5 pM to about 30 pM, about 5 pM to about 20 pM, about 5 pM to about 10 pM, about 10 pM to about 500 pM, about 10 pM to about 400 pM, about 10 pM to about 300 pM, about 10 pM to about 200 pM, about 10 pM to about 100 pM, about 10 pM to about 50 pM, about 10 pM to about 40 pM, about 10 pM to about 30 pM, about 10 pM to about 20 pM, or about 20 pM to about 500 pM, about 20 pM to about 400 pM, about 20 pM to about 300 pM, about 20 pM to about 200 pM, about 20 pM to about 100 pM, about 20 pM to about 50 pM, about 20 pM to about 40 pM, about 20 pM to about 30 pM, or about 30 pM to about 500 pM, about 30 pM to about 400 pM, about 30 pM to about 300 pM, about 30 pM to about 200 pM, about 30 pM to about 100 pM, about 30 pM to about 50 pM, or about 30 pM to about 40 pM. In certain embodiments, an antibody or antigen binding fragment thereof, has increased binding affinity for human IL-11Rα relative to that of the TS7 and 8E2 antibodies (see, for example, U.S. Pat. Nos. 9,796,782; 9,340,618).

In some embodiments, an antibody, or antigen binding fragment thereof, is an IL-11Rα antagonist. In some instances, an antibody, or antigen binding fragment thereof, antagonizes the binding and/or signaling activity between IL-11Rα and its ligand, IL-11. In some embodiments, an antibody, or antigen binding fragment thereof, antagonizes or reduces the binding and/or signaling activity between IL-11Rα and IL-11 by about or at least about 10-1000% (e.g., about 20, 25, 30, 35, 40, 45, 50, 55, 60, 65, 70, 75, 80, 90, 100, 200, 300, 400, 500, 600, 700, 800, 900, 1000% or more), for example, in a cell-based assay. In some embodiments, an anti-IL-11Rα antibody or antigen binding fragment thereof reduces IL-11-mediated STAT3 phosphorylation. In an exemplary assay, cells expressing IL-11Rα and gp130 are cultured in the presence of IL-11 in the presence or absence of the IL-11Rα-binding protein. The level of STAT3 phosphorylation is then assessed by Western blotting or FACS using an antibody specific for phosphorylated STAT3. An exemplary assay making use of FACS is described in Dams-Kozlowska et al., BMC Biotechnol, 12: 8, 2012. In certain embodiments, an antibody or antigen binding fragment thereof, has increased potency as an IL-11 signaling antagonist relative to that of the TS7 and 8E2 antibodies (see, for example, U.S. Pat. Nos. 9,796,782; 9,340,618). In certain embodiments, an antibody or antigen binding fragment thereof has no detectable agonist activity with respect to IL-11 signaling.

In some embodiments, an antibody, or antigen binding fragment thereof, inhibits or otherwise reduces IL-11Rα dimerization or complex formation, for example, with gp130. In certain embodiments, an antibody, or antigen binding fragment thereof, inhibits or otherwise reduces IL-11Rα dimerization or complex formation by about or at least about 10-1000% (e.g., about 20, 25, 30, 35, 40, 45, 50, 55, 60, 65, 70, 75, 80, 90, 100, 200, 300, 400, 500, 600, 700, 800, 900, 1000% or more), for example, in a cell-based assay.

In some embodiments, an anti-IL-11Rα antibody or antigen binding fragment thereof reduces proliferation of cells (e.g., BaF3 cells, B9 cells, T10 cells) expressing IL-11Rα and gp130 (e.g., cells naturally-expressing or modified to express both proteins) which are cultured in the presence of IL-11. Methods for assessing cell proliferation are known in the art and include, for example, MTT reduction and/or thymidine incorporation. Assays with B9 cells or T10 cells are described (see Dams-Kozlowska et al., BMC Biotechnol, 12: 8, 2012; and Yokote et al., J AOAC, 83: 1053-1057, 2000). For T10 cells, proliferation can be measured by colorimetrically detecting reduction of the tetrazolium compound, 4-[3-(4-iodophenyl)-2-(4-nitrophenyl)-2H-5-tetrazolio]-1,3-benzene disulfonate (WST-1). An IL-11Rα-binding protein that reduces the level of proliferation compared to the level observed in the absence of the IL-11Rα-binding protein is considered to reduce or otherwise reduce IL-11R signaling.

In some embodiments, an anti-IL-11Rα antibody or antigen binding fragment thereof reduces IL-11-mediated proliferation of cancer cells (for example, gastric cancer cells, acute myelogenous leukemia (AML) cells). In an exemplary assay, cancer cells (e.g., AGN, MKN45 gastric cancer cells) are cultured in the presence of IL-11 in the presence or absence of the IL-11Rα-binding protein. For AML cells, the cells may also be cultured in the presence of G-CSF. Proliferation of the cells is then measured using standard techniques, e.g., as discussed herein and/or by assessing responses. The antibodies described herein may also be tested for in vitro and in vivo efficacy. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

In particular embodiments, the Fc region of an antibody, or antigen binding fragment thereof, comprises, consists, or consists essentially an IgA (including subclasses IgA1 and IgA2), IgD, IgE, IgG (including subclasses IgG1, IgG2, IgG3, and IgG4), or IgM Fc domain, optionally a human Fc domain, or a hybrid and/or variant thereof. In particular embodiments, the Fc region comprises, consists, or consists essentially of the Fc from human IgG1 or IgG4 (see, e.g., Allberse and Schuurman, Immunology. 105:9-19, 2002), or a fragment or variant thereof. Table F1 below provides exemplary sequences (CH1, hinge (underlined), CH2, and CH3 regions) from human IgG4. Examples of variant IgG4 sequences that can be employed include the S228P/S241P variant.

TABLE F1

Exemplary IgG4 Fc Sequences

| Name | Sequence | SEQ ID NO: |
|---|---|---|
| Wild-type IgG4 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPSCPAPEFLGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK | 258 |
| S228P(EU) S241P(Kabat) | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTC VVVDVSQEDPEVQFNWYVDGVEVHNAKTKPREEQFNSTYRVVSVLIV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK | 259 | formation of L-CFU in the case of AML cells. Exemplary assays adaptable to the present disclosure are included in Zhang et al., Int J Biol Sci., 8: 383-393, 2012 and Kimura et al., Leukemia, 13: 1018-1027, 1999.

Merely for illustrative purposes, the binding interactions between IL-11Rα an antibody, or antigen binding fragment thereof, described herein, or the binding/signaling between IL-11Rα and IL-11, can be detected and quantified using a variety of routine methods, including Biacore® assays (for example, with appropriately tagged soluble reagents, bound to a sensor chip), FACS analyses with cells expressing IL-11Rα on the cell surface (either native, or recombinant), immunoassays, fluorescence staining assays, ELISA assays, and microcalorimetry approaches such as ITC (Isothermal Titration Calorimetry). Similarly, the functional properties of anti-IL-11Rα antibodies may be assessed using a variety of methods known to the skilled person affinity/binding assays (for example, surface plasmon resonance, competitive inhibition assays); cytotoxicity assays, cell viability assays, cell proliferation or differentiation assays, cancer cell and/or tumor growth inhibition using in vitro or in vivo models. Other assays may test the ability of antibodies described herein to block normal IL-11Rα-mediated In certain embodiments, an antibody or antigen binding fragment thereof comprises variant or otherwise modified Fc region(s), including those having altered properties or biological activities relative to wild-type Fc region(s). Examples of modified Fc regions include those having mutated sequences, for instance, by substitution, insertion, deletion, or truncation of one or more amino acids relative to a wild-type sequence, hybrid Fc polypeptides composed of domains from different immunoglobulin classes/subclasses, Fc polypeptides having altered glycosylation/sialylation patterns, and Fc polypeptides that are modified or derivatized, for example, by biotinylation (see, e.g., US Application No. 2010/0209424), phosphorylation, sulfation, etc., or any combination of the foregoing. Such modifications can be employed to alter (e.g., increase, decrease) the binding properties of the Fc region to one or more particular FcRs (e.g., FcγRI, FcγRIIa, FcγRIIb, FcγRIIc, FcγRIIIa, FcγRIIIb, FcRn), its pharmacokinetic properties (e.g., stability or half-life, bioavailability, tissue distribution, volume of distribution, concentration, elimination rate constant, elimination rate, area under the curve (AUC), clearance, $C_{max}$, $t_{max}$, $C_{min}$, fluctuation), its immunogenicity, its complement fixation or activation, and/or the CDC/ADCC/

ADCP-related activities of the Fc region, among other properties described herein, relative to a corresponding wild-type Fc sequence of an antibody or antigen binding fragment thereof. Included are modified Fc regions of human and/or mouse origin.

In certain embodiments, an antibody or antigen binding fragment thereof comprises a hybrid Fc region, for example, an Fc region that comprises a combination of Fc domains (e.g., hinge, $CH_2$, $CH_3$, $CH_4$) from immunoglobulins of different species (e.g., human, mouse), different Ig classes, and/or different Ig subclasses. Also included are antibodies or antigen binding fragments thereof that comprise derivatized or otherwise modified Fc regions. In certain aspects, the Fc region is modified by phosphorylation, sulfation, acrylation, glycosylation, methylation, farnesylation, acetylation, amidation, and the like, for instance, relative to a wild-type or naturally-occurring Fc region. In certain embodiments, the Fc region comprises wild-type or native glycosylation patterns, or alternatively, it comprises increased glycosylation relative to a native form, decreased glycosylation relative to a native form, or it is entirely deglycosylated. As one example of a modified Fc glycoform, decreased glycosylation of an Fc region reduces binding to the C1q region of the first complement component C1, a decrease in ADCC-related activity, and/or a decrease in CDC-related activity. Certain embodiments thus employ a deglycosylated or aglycosylated Fc region. See, e.g., WO 2005/047337 for the production of exemplary aglycosylated Fc regions. Another example of an Fc region glycoform is generated by substituting the Q295 position with a cysteine residue (see, e.g., U.S. Application No. 2010/0080794), according to the Kabat et al. numbering system. Certain embodiments include Fc regions where about 80-100% of the glycoprotein in Fc region comprises a mature core carbohydrate structure that lacks fucose (see, e.g., U.S. Application No. 2010/0255013). Some embodiments include Fc regions that are optimized by substitution or deletion to reduce the level of fucosylation, for instance, to increase affinity for FcγRI, FcγRIa, or FcγRIIIa, and/or to improve phagocytosis by FcγRIIa-expressing cells (see U.S. Application Nos. 2010/0249382 and 2007/0148170).

As another example of a modified Fc glycoform, an Fc region of an antibody or antigen binding fragment thereof may comprise oligomannose-type N-glycans, and optionally have one or more of the following: increased ADCC effector activity, increased binding affinity for FcγRIIIA (and certain other FcRs), similar or increased binding specificity for the target of the IL-11Rα polypeptide, similar or higher binding affinity for the target of the IL-11Rα polypeptide, and/or similar or lower binding affinity for mannose receptor, relative to a corresponding Fc region that contains complex-type N-glycans (see, e.g., U.S. Application No. 2007/0092521 and U.S. Pat. No. 7,700,321). As another example, enhanced affinity of Fc regions for FcγRs has been achieved using engineered glycoforms generated by expression of antibodies in engineered or variant cell lines (see, e.g., Umana et al., Nat Biotechnol. 17:176-180, 1999; Davies et al., Biotechnol Bioeng. 74:288-294, 2001; Shields et al., J Biol Chem. 277:26733-26740, 2002; Shinkawa et al., 2003, J Biol Chem. 278:3466-3473, 2003; and U.S. Application No. 2007/0111281). Certain Fc region glycoforms comprise an increased proportion of N-glycoside bond type complex sugar chains, which do not have the 1-position of fucose bound to the 6-position of N-acetylglucosamine at the reducing end of the sugar chain (see, e.g., U.S. Application No. 2010/0092997). Particular embodiments may include IgG Fc region that is glycosylated with at least one galactose moiety connected to a respective terminal sialic acid moiety by an α-2,6 linkage, optionally where the Fc region has a higher anti-inflammatory activity relative to a corresponding, wild-type Fc region (see U.S. Application No. 2008/0206246). Certain of these and related altered glycosylation approaches have generated substantial enhancements of the capacity of Fc regions to selectively bind FcRs such as FcγRIII, to mediate ADCC, and to alter other properties of Fc regions, as described herein.

Certain variant, fragment, hybrid, or otherwise modified Fc regions of an antibody or antigen binding fragment thereof may have altered binding to one or more FcRs, and/or corresponding changes to effector function, relative to a corresponding, wild-type Fc sequence (e.g., same species, same Ig class, same Ig subclass). For instance, such Fc regions may have increased binding to one or more of Fcγ receptors, Fcα receptors, Fcε receptors, and/or the neonatal Fc receptor, relative to a corresponding, wild-type Fc sequence. In other embodiments, variant, fragment, hybrid, or modified Fc regions may have decreased binding to one or more of Fcγ receptors, Fcα receptors, Fcε receptors, and/or the neonatal Fc receptor, relative to a corresponding, wild-type Fc sequence. Specific FcRs are described elsewhere herein.

In some embodiments, an antibody comprises an Fc domain, comprising one or more mutations to increase binding to one or more of Fcγ receptors, Fcα receptors, Fcε receptors, and/or the neonatal Fc receptor, relative to a corresponding, wild-type Fc sequence. In some embodiments, an antibody comprises an IgG1 or IgG3 Fc domain, comprising one or more mutations to increase binding to one or more of Fcγ receptors, Fcα receptors, Fcε receptors, and/or the neonatal Fc receptor, relative to a corresponding, wild-type Fc sequence. In some embodiments, an antibody comprises an Fc domain, comprising one or more mutations to increase effector function. In some embodiments the at least one antibody comprises an Fc domain selected from a human IgG1 and IgG3, comprising one or more mutations to increase effector function.

In some embodiments, an antibody is blocking antibody that comprises an Fc domain with high effector activity. In some embodiments, the blocking antibody comprises an Fc domain selected from a human IgG1 and IgG3, comprising one or more mutations to increase effector function. In some embodiments, an antibody is a partial-blocking antibody that comprises an Fc domain with high effector activity. In some embodiments, the a partial-blocking antibody comprises an Fc domain selected from a human IgG1 and IgG3, comprising one or more mutations to increase effector function. In some embodiments, an antibody is a non-blocking antibody that comprises an Fc domain with high effector activity. In some embodiments, the non-blocking antibody comprises an Fc domain selected from a human IgG1 or IgG3, comprising one or more mutations to increase effector function.

In some embodiments, an antibody comprises an Fc domain, comprising one or more mutations to decrease binding to one or more of Fcγ receptors, Fcα receptors, Fcε receptors, and/or the neonatal Fc receptor, relative to a corresponding, wild-type Fc sequence. In some embodiments, an antibody comprises an IgG1 or IgG3 Fc domain, comprising one or more mutations to decrease binding to one or more of Fcγ receptors, Fcα receptors, Fcε receptors, and/or the neonatal Fc receptor, relative to a corresponding, wild-type Fc sequence. In some embodiments, an antibody comprises an Fc domain, comprising one or more mutations to decrease effector function. In some embodiments, an antibody comprises an Fc domain selected from a human IgG2 and IgG4, comprising one or more mutations to decrease effector function.

In some embodiments, an antibody is a blocking antibody comprising an Fc domain with low effector activity. In some embodiments, the blocking antibody comprises an Fc domain selected from a human IgG2 and IgG4, comprising one or more mutations to decrease effector function. In some embodiments, an antibody is a partial-blocking antibody comprising an Fc domain with low effector activity. In some embodiments, the partial-blocking antibody comprises an Fc domain selected from a human IgG2 and IgG4, comprising one or more mutations to decrease effector function. In some embodiments, an antibody is a non-blocking antibody comprising an Fc domain with low effector activity. In some embodiments, the non-blocking antibody comprises an Fc domain selected from a human IgG2 and IgG4, comprising one or more mutations to decrease effector function.

Specific examples of Fc variants having altered (e.g., increased, decreased) effector function/FcR binding can be found, for example, in U.S. Pat. Nos. 5,624,821 and 7,425,619; U.S. Application Nos. 2009/0017023, 2009/0010921, and 2010/0203046; and WO 2000/42072 and WO 2004/016750. Certain examples include human Fc regions having a one or more substitutions at position 298, 333, and/or 334, for example, S298A, E333A, and/or K334A (based on the numbering of the EU index of Kabat et al.), which have been shown to increase binding to the activating receptor FcγRIIIa and reduce binding to the inhibitory receptor FcγRIIb. These mutations can be combined to obtain double and triple mutation variants that have further improvements in binding to FcRs. Certain embodiments include a S298A/E333A/K334A triple mutant, which has increased binding to FcγRIIIa, decreased binding to FcγRIIb, and increased ADCC (see, e.g., Shields et al., J Biol Chem. 276:6591-6604, 2001; and Presta et al., Biochem Soc Trans. 30:487-490, 2002). See also engineered Fc glycoforms that have increased binding to FcRs, as disclosed in Umana et al., supra; and U.S. Pat. No. 7,662,925. Some embodiments include Fc regions that comprise one or more substitutions selected from 434S, 252Y/428L, 252Y/4345, and 428L/4345 (see U.S. Application Nos. 2009/0163699 and 20060173170), based on the EU index of Kabat et al.

Certain variant, fragment, hybrid, or modified Fc regions may have altered effector functions, relative to a corresponding, wild-type Fc sequence. For example, such Fc regions may have increased complement fixation or activation, increased C1q binding affinity, increased CDC-related activity, increased ADCC-related activity, and/or increased ADCP-related activity, relative to a corresponding, wild-type Fc sequence. In other embodiments, such Fc regions may have decreased complement fixation or activation, decreased C1q binding affinity, decreased CDC-related activity, decreased ADCC-related activity, and/or decreased ADCP-related activity, relative to a corresponding, wild-type Fc sequence. As merely one illustrative example, an Fc region may comprise a deletion or substitution in a complement-binding site, such as a C1q-binding site, and/or a deletion or substitution in an ADCC site. Examples of such deletions/substitutions are described, for example, in U.S. Pat. No. 7,030,226. Many Fc effector functions, such as ADCC, can be assayed according to routine techniques in the art. (see, e.g., Zuckerman et al., CRC Crit Rev Microbiol. 7:1-26, 1978). Useful effector cells for such assays includes, but are not limited to, natural killer (NK) cells, macrophages, and other peripheral blood mononuclear cells (PBMC). Alternatively, or additionally, certain Fc effector functions may be assessed in vivo, for example, by employing an animal model described in Clynes et al. PNAS. 95:652-656, 1998.

Certain variant hybrid, or modified Fc regions may have altered stability or half-life relative to a corresponding, wild-type Fc sequence. In certain embodiments, such Fc regions may have increased half-life relative to a corresponding, wild-type Fc sequence. In other embodiments, variant hybrid, or modified Fc regions may have decreased half-life relative to a corresponding, wild-type Fc sequence. Half-life can be measured in vitro (e.g., under physiological conditions) or in vivo, according to routine techniques in the art, such as radiolabeling, ELISA, or other methods. In vivo measurements of stability or half-life can be measured in one or more bodily fluids, including blood, serum, plasma, urine, or cerebrospinal fluid, or a given tissue, such as the liver, kidneys, muscle, central nervous system tissues, bone, etc. As one example, modifications to an Fc region that alter its ability to bind the FcRn can alter its half-life in vivo. Assays for measuring the in vivo pharmacokinetic properties (e.g., in vivo mean elimination half-life) and non-limiting examples of Fc modifications that alter its binding to the FcRn are described, for example, in U.S. Pat. Nos. 7,217,797 and 7,732,570; and U.S. Application Nos. US 2010/0143254 and 2010/0143254.

Additional non-limiting examples of modifications to alter stability or half-life include substitutions/deletions at one or more of amino acid residues selected from 251-256, 285-290, and 308-314 in the $CH_2$ domain, and 385-389 and 428-436 in the $CH_3$ domain, according to the numbering system of Kabat et al. See U.S. Application No. 2003/0190311. Specific examples include substitution with leucine at position 251, substitution with tyrosine, tryptophan or phenylalanine at position 252, substitution with threonine or serine at position 254, substitution with arginine at position 255, substitution with glutamine, arginine, serine, threonine, or glutamate at position 256, substitution with threonine at position 308, substitution with proline at position 309, substitution with serine at position 311, substitution with aspartate at position 312, substitution with leucine at position 314, substitution with arginine, aspartate or serine at position 385, substitution with threonine or proline at position 386, substitution with arginine or proline at position 387, substitution with proline, asparagine or serine at position 389, substitution with methionine or threonine at position 428, substitution with tyrosine or phenylalanine at position 434, substitution with histidine, arginine, lysine or serine at position 433, and/or substitution with histidine, tyrosine, arginine or threonine at position 436, including any combination thereof. Such modifications optionally increase affinity of the Fc region for the FcRn and thereby increase half-life, relative to a corresponding, wild-type Fc region.

Certain variant hybrid, or modified Fc regions may have altered solubility relative to a corresponding, wild-type Fc sequence. In certain embodiments, such Fc regions may have increased solubility relative to a corresponding, wild-type Fc sequence. In other embodiments, variant hybrid, or modified Fc regions may have decreased solubility relative to a corresponding, wild-type Fc sequence. Solubility can be measured, for example, in vitro (e.g., under physiological conditions) according to routine techniques in the art. Exemplary solubility measurements are described elsewhere herein.

Variant Fc regions can also have one or more mutated hinge regions, as described, for example, in U.S. Application No. 2003/0118592. For instance, one or more cysteines in a hinge region can be deleted or substituted with a different amino acid. The mutated hinge region can comprise no cysteine residues, or it can comprise 1, 2, or 3 fewer cysteine residues than a corresponding, wild-type hinge region. In some embodiments, an Fc region having a mutated hinge region of this type exhibits a reduced ability to dimerize, relative to a wild-type Ig hinge region.

In particular embodiments, an antibody or antigen binding fragment thereof has a biological half life at about pH 7.4, at about a physiological pH, at about 25° C. or room temperature, and/or at about 37° C. or human body temperature (e.g., in vivo, in serum, in a given tissue, in a given species such as rat, mouse, monkey, or human), of about or at least about 30 minutes, about 1 hour, about 2 hour, about 3 hours, about 4 hours, about 5 hours, about 6 hours, about 12 hours, about 18 hours, about 20 hours, about 24 hours, about 30 hours, about 36 hours, about 40 hours, about 48 hours, about 50 hours, about 60 hours, about 70 hours, about 72 hours, about 80 hours, about 84 hours, about 90 hours, about 96 hours, about 120 hours, or about 144 hours or more, or about 1 week, or about 2 weeks, or about 3 weeks, or about 4 weeks, or about 5 weeks, or about 6 weeks or more, or any intervening half-life, including all ranges in between.

In some embodiments, an antibody or antigen binding fragment thereof has a $T_m$ of about or at least about 60, 61, 62, 63, 64, 65, 66, 67, 68, 69, 70, 71, 72, 73, 74, or 75° C. In some embodiments, an antibody or antigen binding fragment thereof has a $T_m$ of about 65° C. or greater, for example, in PBS (phosphate buffered saline).

In some embodiments, an antibody or antigen binding fragment thereof conjugated to one or more cytotoxic or chemotherapeutic agents. General examples of cytotoxic or chemotherapeutic agents include, without limitation, alkylating agents, anti-metabolites, anthracyclines, anti-tumor antibiotics, platinums, type I topoisomerase inhibitors, type II topoisomerase inhibitors, vinca alkaloids, and taxanes. Specific examples of cytotoxic or chemotherapeutic agents include, without limitation, cyclophosphamide, cilengitide, lomustine (CCNU), melphalan, procarbazine, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitinib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof. Further examples of cytotoxic or chemotherapeutic agents include alkylating agents such as thiotepa, cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above.

In some embodiments, a herein-disclosed antibody is conjugated or operably linked to a radioisotope to form a radioconjugate and/or macrocyclic chelators useful for conjugating radiometal ions. A variety of radioactive isotopes are available for the production of radioconjugate antibodies. Examples include, but are not limited to $^{90}$Y, $^{123}$I, $^{125}$I, $^{131}$I, $^{186}$Re, $^{188}$Re, $^{211}$At, and $^{212}$Bi. In certain embodiments, the macrocyclic chelator is 1,4,7,10-tetraazacyclododecane-N,N',N",N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

Other modifications of the antibodies (and polypeptides) of the disclosure are also contemplated herein. For example, in some embodiments the antibody is linked to one of a variety of nonproteinaceous polymers, e.g., polyethylene glycol, polypropylene glycol, polyoxyalkylenes, or copolymers of polyethylene glycol and polypropylene glycol. In some embodiments, the antibody is entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies or antigen binding fragments thereof can be used in any of the compositions, methods, and/or kits described herein, and combined with one or more of the additional agents described herein.

Methods of Use and Pharmaceutical Compositions

Certain embodiments relate to methods of treating, ameliorating the symptoms of, and/or reducing the progression of, a disease or condition in a subject in need thereof, comprising administering to the subject an antibody or antigen binding fragment thereof that binds to interleukin-11 receptor subunit α (IL-11Rα), as described herein, or a pharmaceutical composition comprising the same. In some instances, the antibody or antigen binding fragment thereof antagonizes the binding/signaling activity between the IL-11Rα and its ligand, IL-11. In some embodiments, the disease or condition is an IL-11-associated or IL-11-mediated disease or condition. In some embodiments, the disease or condition is a cancer, an inflammatory disease, an autoimmune disease, a wasting disease, a bone disease, or a fibrotic disease.

In some embodiments, as noted above, the disease or condition is a cancer or tumor. For example, in some instances, the cancer expresses or overexpresses IL-11Rα and/or IL-11, and in some instances, the cancer displays IL-11Rα/IL-11-dependent growth, adhesion, migration, invasion, and/or chemoresistance. In some instances, the cancer is a primary cancer. In some instances, the cancer is a metastatic cancer.

Exemplary cancers include, without limitation, bone cancer, prostate cancer, melanoma (e.g., metastatic melanoma), pancreatic cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia, hairy cell leukemias, acute lymphoblastic leukemias), lymphoma (e.g., non-Hodgkin's lymphomas, Hodgkin's lymphoma), hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer. In specific embodiments, the cancer is a metastatic cancer, for example, which has metastasized to the bone.

In some embodiments, the methods and compositions described herein increase median survival time of a subject by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the methods and compositions described herein increase median survival time of a subject by 1 year, 2 years, 3 years, or longer. In some embodiments, the methods and compositions described herein increase progression-free survival by 2 weeks, 3 weeks, 4 weeks, 5 weeks, 6 weeks, 7 weeks, 8 weeks, 9 weeks, 10 weeks or longer. In certain embodiments, the methods and compositions described herein increase progression-free survival by 1 year, 2 years, 3 years, or longer.

In certain embodiments, the methods and compositions described herein are sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In some embodiments, the methods and compositions described herein reduce the growth rate (e.g., in vivo or in vitro, including cancer cells isolated from a biopsy or other sample and grown in vitro) of the cancer by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some instances, the methods and compositions described herein reduce cancer cell initiation, migration, adhesion, invasiveness, and/or metastasis by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some instances, the methods and compositions described herein reduce angiogenesis in the tumor environment by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In certain embodiments, the disease or condition is an inflammatory disease. Non-limiting examples of inflammatory diseases and conditions include airway or lung inflammation (e.g., inflammatory lung disease), asthma, rhinitis, chronic obstructive pulmonary disorder (COPD), dermatitis, psoriasis, hepatitis, gastric inflammation, irritable bowel syndrome (IBS), ulcerative colitis, Crohn's disease, colitis, diverticulitis, lupus erythematous, nephritis, Parkinson's disease, multiple sclerosis (MS), Alzheimer's disease, arthritis, rheumatoid arthritis, sepsis, infection-induced inflammation, cardiovascular diseases such as atherosclerosis and vasculitis, diabetes, and gout.

In certain embodiments, the disease or condition is an autoimmune disease. Non-limiting examples of autoimmune diseases and conditions include arthritis (including rheumatoid arthritis, reactive arthritis), systemic lupus erythematosus (SLE), psoriasis, inflammatory bowel disease (IBD), ulcerative colitis, Crohn's disease, encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, fibromyalgia, pemphigus vulgaris, Sjogren's syndrome, Kawasaki's Disease, hyperthyroidism/Graves' disease, hypothyroidism/Hashimoto's disease, endometriosis, scleroderma, pernicious anemia, Goodpasture syndrome, Guillain-Barré syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis, rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

In certain embodiments, the disease or condition is a wasting disease. Non-limiting examples of wasting diseases and conditions include cachexia, including cachexia associated with cancer or renal failure, and sarcopenia. In certain embodiments, the disease or condition is a bone disease. Non-limiting examples of bone diseases and conditions include osteoporosis (including post-menopausal osteoporosis), bone fracture, Paget's disease of bone, and bone resorption/damage associated with cancer or cancer therapy, including chemotherapy, hormone ablation, and hormone inhibition.

In some embodiments, the disease or condition is fibrosis, or a fibrotic disease. Examples include fibrosis of the lungs, cardiovascular system, liver, brain, joints (e.g., knee, hip, ankle, foot joints, shoulder, elbow, wrist, hand joints, spinal vertebrae), intestine, skin, kidney, liver, thyroid, bone marrow, retroperitoneum, eye (see, for example, Schafer et al., Nature. 552: 110-115, 2017; and Ng et al., Sci Transl Med. 2019 Sep. 25; 11(511)).

In some embodiments, the fibrosis of the lungs is selected from fibrothorax, pulmonary fibrosis (for example, cystic fibrosis, interstitial lung disease (ILD), autosomal recessive genetic disease such as Hermansky-Pudlak syndrome type 1, 2, 3, 4, 5, 6, 7, or 8), and radiation-induced lung injury. In some embodiments, the pulmonary fibrosis is related to ILD, for example, idiopathic or secondary ILD. Examples of idiopathic ILD include idiopathic pulmonary fibrosis (IPF), desquamative interstitial pneumonia (DIP), acute interstitial pneumonia (AIP) also known as Hamman-Rich syndrome, nonspecific interstitial pneumonia (NSIP), respiratory bronchiolitis-associated interstitial lung disease (RB-ILD), cryptogenic organizing pneumonia (COP), and lymphoid interstitial pneumonia (LIP). General examples of secondary ILD include ILD related to connective tissue and autoimmune diseases (for example, sarcoidosis, rheumatoid arthritis, systemic lupus erythematosus, systemic sclerosis, polymyositis, dermatomyositis, antisynthetase syndrome), inhaled substances (for example, silicosis, asbestosis, berylliosis, industrial printing chemicals, chronic hypersensitivity pneumonitis), drugs (drug-induced ILD, for example, antibiotics, chemotherapeutics, anti-arrhythmic agents), infections (for example, SARS CoV-2, atypical pneumonia, pneumocystis pneumonia, tuberculosis, *Chlamydia trachomatis*, respiratory syncytial virus), malignancies (lymphangitic carcinomatosis), and pediatric ILDs such as diffuse developmental disorders, growth abnormalities deficient alveolarization, infant conditions of undefined cause, and ILD related to alveolar surfactant region.

In particular embodiments, the fibrosis of the cardiovascular system is myocardial fibrosis (for example, interstitial fibrosis, replacement fibrosis).

In some embodiments, the antibodies described herein are selective for both mouse and human IL-11Rα, block IL-11 signaling through both the STAT3 and ERK pathways, and abrogate both cis- and trans-IL-11 signaling. Following TGFβ stimulation, certain anti-huIL-11Rα antibodies described herein have been shown to reduce collagen expression in primary IPF patient fibroblasts and decrease expression of procollagen I and TIMP by PCLS from healthy donors. Similar reductions in procollagen release have been observed in response to anti-huIL-11Rα in preliminary PCLS studies from IPF patients. In mouse bleomycin lung fibrosis studies, blockade of IL-11Rα signaling reduces lung fibrosis and decreases BAL inflammatory cells when administered prophylactically or therapeutically after the onset of lung fibrosis.

In certain embodiments, the methods and compositions described herein are sufficient to result in stable disease. In certain embodiments, the methods and compositions described herein are sufficient to result in clinically relevant reduction in symptoms of a particular disease indication known to the skilled clinician.

For in vivo use, certain embodiments include pharmaceutical compositions, comprising an antibody or antigen binding fragment thereof, as described herein, and a pharmaceutically acceptable carrier. To prepare a therapeutic or pharmaceutical composition, an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, intraocular, subcutaneous, direct instillation into the bladder, or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate therapeutic or pharmaceutical composition, can be carried out via any of the accepted modes of administration of agents for serving similar utilities. The therapeutic or pharmaceutical compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intraocular, intradermal, intramuscular, subcutaneous, installation into the bladder, or topical. Preferred modes of administration depend upon the nature of the condition to be treated or prevented. Particular embodiments include administration by IV infusion.

Carriers can include, for example, pharmaceutically or physiologically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine, histidine, and/or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related therapeutic or pharmaceutical compositions thus include, without limitation, oral, topical, transdermal, inhalation, parenteral, sublingual, buccal, ocular, rectal, vaginal, and intranasal. The term parenteral as used herein includes subcutaneous injections, intravenous, instillation into the bladder, intramuscular, intrasternal injection or infusion techniques. Therapeutic or pharmaceutical compositions according to certain embodiments of the present disclosure are formulated so as to allow the active ingredients contained therein to be bioavailable upon administration of the composition to a subject or patient. Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will typically contain a therapeutically effective amount of an agent described herein, for treatment of a disease or condition of interest.

A therapeutic or pharmaceutical composition can be in the form of a solid or liquid. In some embodiments, the carrier(s) are particulate, so that the compositions are, for example, in tablet or powder form. The carrier(s) can be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, gel, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The therapeutic or pharmaceutical composition may be in the form of a liquid, for example, an elixir, syrup, solution, gel, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid therapeutic or pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid therapeutic or pharmaceutical composition intended for either parenteral, intraocular, or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral therapeutic or pharmaceutical compositions contain between about 4% and about 75% of the agent of interest. In certain embodiments, therapeutic or pharmaceutical compositions and preparations are prepared so that a parenteral dosage unit contains between 0.01 to 10% by weight of the agent of interest prior to dilution.

The therapeutic or pharmaceutical compositions may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a therapeutic or pharmaceutical composition for topical administration. If intended for transdermal administration, the composition may include a transdermal patch or iontophoresis device.

The therapeutic or pharmaceutical compositions may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The therapeutic or pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The therapeutic or pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a therapeutic or pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The therapeutic or pharmaceutical compositions may be administered in a therapeutically effective amount, which will vary depending upon a variety of factors including the activity of the specific compound employed; the metabolic stability and length of action of the compound; the age, body weight, general health, sex, and diet of the subject; the mode and time of administration; the rate of excretion; the drug combination; the severity of the particular disorder or condition; and the subject undergoing therapy. In some instances, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g). In some embodiments, the therapeutically effective dose is administered on a weekly, bi-weekly, or monthly basis. In specific embodiments, the therapeutically effective dose is administered on a weekly, bi-weekly, or monthly basis, for example, at a dose of about 1-10 or 1-5 mg/kg, or about 1, 2, 3, 4, 5, 6, 7, 8, 9, or 10 mg/kg.

Also included are patient care kits, comprising (a) an antibody or antigen binding fragment thereof that binds to IL-11Rα, as described herein; and optionally (b) at least one additional therapeutic agent. In certain kits, (a) and (b) are in separate therapeutic compositions. In some kits, (a) and (b) are in the same therapeutic composition.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

In some embodiments, a patient care kit contains separate containers, dividers, or compartments for the composition(s) and informational material(s). For example, the composition(s) can be contained in a bottle, vial, or syringe, and the informational material(s) can be contained in association with the container. In some embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an antibody and optionally at least one additional therapeutic agent. For example, the kit includes a plurality of syringes, ampules, foil packets, or blister packs, each containing a single unit dose of an antibody and optionally at least one additional therapeutic agent. The containers of the kits can be air tight, waterproof (e.g., impermeable to changes in moisture or evaporation), and/or light-tight.

The patient care kit optionally includes a device suitable for administration of the composition, e.g., a syringe, inhalant, dropper (e.g., eye dropper), swab (e.g., a cotton swab or wooden swab), or any such delivery device. In some embodiments, the device is an implantable device that dispenses metered doses of the agent(s). Also included are methods of providing a kit, e.g., by combining the components described herein.

Expression and Purification Systems Certain embodiments include methods and related compositions for expressing and purifying an anti-IL-11Rα antibody or antigen binding fragment thereof described herein. Such recombinant anti-IL-11Rα antibodies can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6. As one general example, anti-IL-11Rα antibodies may be prepared by a procedure including one or more of the steps of: (a) preparing a construct that comprises a polynucleotide sequence which encodes an anti-IL-11Rα antibody heavy chain and/or light chains, and which is operably linked to a regulatory element; (b) introducing the construct into a host cell; (c) culturing the host cell to express the anti-IL-11Rα antibody; and (d) isolating the anti-IL-11Rα from the host cell.

Certain embodiments thus include polynucleotides that encode an anti-IL-11Rα antibody or antigen binding fragment thereof described herein, including vectors comprising said polynucleotides, and host cells comprising the polynucleotides and/or vectors. In order to express a desired polypeptide, a nucleotide sequence encoding an anti-IL-11Rα, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

Certain embodiments may employ *E. coli*-based expression systems (see, e.g., Structural Genomics Consortium et al., *Nature Methods*. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. Cell lysis and sample handling may also be improved using reagents sold under the trademarks BENZONASE® nuclease and BUG-BUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG. Particular embodiments employ hexahistidine tags (such as those sold under the trademark HIS·TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif*. 50:58-67, 2006). As a further example, certain embodiments may employ a cold-shock induced *E. coli* high-yield production system, because overexpression of proteins in *Escherichia coli* at low temperature improves their solubility and stability (see, e.g., Qing et al., Nature Biotechnology. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544 (1987). Also included are *Pichia pandoris* expression systems (see, e.g., Li et al., Nature Biotechnology. 24, 210-215, 2006; and Hamilton et al., Science, 301:1244, 2003). Certain embodiments include yeast systems that are engineered to selectively glycosylate proteins, including yeast that have humanized N-glycosylation pathways, among others (see, e.g., Hamilton et al., Science. 313:1441-1443, 2006; Wildt et al., Nature Reviews Microbiol. 3:119-28, 2005; and Gerngross et al., Nature-Biotechnology. 22:1409-1414, 2004; U.S. Pat. Nos. 7,629, 163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et al., EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., Proc. Natl. Acad. Sci. U.S.A. 91:3224-3227 (1994)). Also included are baculovirus expression systems, including those that utilize SF9, SF21, and *T. ni* cells (see, e.g., Murphy and Piwnica-Worms, Curr Protoc Protein Sci. Chapter 5:Unit5.4, 2001). Insect systems can provide post-translation modifications that are similar to mammalian systems.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NS0 and Sp2/0. For a review of certain mammalian host cell lines suitable for antibody production, see, e.g., Yazaki and Wu, Methods in Molecular Biology, Vol. 248 (B. K.C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is the cell-free expression of proteins. These and related embodiments typically utilize purified RNA polymerase, ribosomes, tRNA and ribonucleotides; these reagents may be produced by extraction from cells or from a cell-based expression system.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., Results Probl. Cell Differ. 20:125-162 (1994)).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Any number of selection systems may be used to recover transformed or transduced cell lines. These include, but are not limited to, the herpes simplex virus thymidine kinase (Wigler et al., Cell 11:223-232 (1977)) and adenine phosphoribosyltransferase (Lowy et al., Cell 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., PNAS USA. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. Sci. U.S.A. 85:8047-51 (1988)). The use of visible markers has gained popularity with such markers as green fluorescent protein (GFP) and other fluorescent proteins (e.g., RFP, YFP), anthocyanins, β-glucuronidase and its substrate GUS, and luciferase and its substrate luciferin, being widely used not only to identify transformants, but also to quantify the amount of transient or stable protein expression attributable to a specific vector system (see, e.g., Rhodes et al., Methods Mol. Biol. 55:121-131 (1995)).

Also included are high-throughput protein production systems, or micro-production systems. Certain aspects may utilize, for example, hexa-histidine fusion tags for protein expression and purification on metal chelate-modified slide surfaces or MagneHis Ni-Particles (see, e.g., Kwon et al., BMC Biotechnol. 9:72, 2009; and Lin et al., Methods Mol Biol. 498:129-41, 2009)). Also included are high-throughput cell-free protein expression systems (see, e.g., Sitaraman et al., Methods Mol Biol. 498:229-44, 2009). These and related embodiments can be used, for example, to generate microarrays of antibodies which can then be used for screening libraries to identify antibodies and antigen binding domains that interact with the IL-11Rα polypeptide(s) of interest.

A variety of protocols for detecting and measuring the expression of polynucleotide-encoded products, using binding agents or antibodies such as polyclonal or monoclonal antibodies specific for the product, are known in the art. Examples include enzyme-linked immunosorbent assay (ELISA), western immunoblots, radioimmunoassays (RIA), and fluorescence activated cell sorting (FACS). These and other assays are described, among other places, in Hampton et al., Serological Methods, a Laboratory Manual (1990) and Maddox et al., J. Exp. Med. 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grown on serum free medium (see, e.g., Rosser et al., Protein Expr. Purif. 40:237-43, 2005; and U.S. Pat. No. 6,210,922).

An antibody, or antigen binding fragment thereof, produced by a recombinant cell may be secreted or contained intracellularly depending on the sequence and/or the vector used. As will be understood by those of skill in the art, expression vectors containing polynucleotides may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification and/or detection of soluble proteins. Examples of such domains include cleavable and non-cleavable affinity purification and epitope tags such as avidin, FLAG tags, poly-histidine tags (e.g., 6xHis), cMyc tags, V5-tags, glutathione S-transferase (GST) tags, and others.

The protein produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Also included are analytical methods such as SDS-PAGE (e.g., Coomassie, silver stain), immunoblot, Bradford, and ELISA, which may be utilized during any step of the production or purification process, typically to measure the purity of the protein composition.

Also included are methods of concentrating anti-IL-11Rα antibodies and antigen binding fragments thereof, and composition comprising concentrated soluble proteins. In certain aspects, concentrated solutions of anti-IL-11Rα antibodies comprise proteins at a concentration of about 5 mg/mL; or about 8 mg/mL; or about 10 mg/mL; about 15 mg/mL; or about 20 mg/mL or more.

In some aspects, the compositions are substantially monodisperse, for example, where the anti-IL-11Rα antibody exists primarily (i.e., at least about 90%, or greater) in one apparent molecular weight form when assessed, for example, by size exclusion chromatography, dynamic light scattering, and/or analytical ultracentrifugation.

In some aspects, the compositions have a purity (on a protein basis) of at least about 90%, or in some aspects at least about 95% purity, or in some embodiments, at least about 98% purity. Purity can be determined via any routine analytical method as known in the art.

In some aspects, the compositions have a high molecular weight aggregate content of less than about 10%, less than about 5%, less than about 3%, less than about 1%. High molecular weight aggregate content can be determined by a variety of analytical techniques including for example, by size exclusion chromatography, dynamic light scattering, and/or analytical ultracentrifugation.

Examples of concentration approaches contemplated herein include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the anti-IL-11Rα antibodies, reagents, or related agents have a purity of at least about 90%, as measured according to routine techniques in the art. In certain embodiments, an anti-IL-11Rα composition has a purity of at least about 95%. In specific embodiments, such as therapeutic or pharmaceutical compositions, an anti-IL-11Rα antibody composition has a purity of at least about 97% or 98% or 99%. In some embodiments, such as when being used as reference or research reagents, anti-IL-11Rα antibodies can be of lesser purity, and may have a purity of at least about 50%, 60%, 70%, or 80%. Purity can be measured overall or in relation to selected components, such as other proteins, e.g., purity on a protein basis.

Purified antibodies can also be characterized according to their biological characteristics. Binding affinity and binding kinetics can be measured according to a variety of techniques known in the art, such as Biacore® and related technologies that utilize surface plasmon resonance (SPR), an optical phenomenon that enables detection of unlabeled interactants in real time. SPR-based biosensors can be used in determination of active concentration, screening and characterization in terms of both affinity and kinetics. The presence or levels of one or more canonical or non-canonical biological activities can be measured according to cell-based assays, including those that utilize a cellular binding partner of a selected anti-IL-11Rα antibody, which is functionally coupled to a readout or indicator, such as a fluorescent or luminescent indicator of biological activity, as described herein.

In certain embodiments, as noted above, a composition is substantially endotoxin free, including, for example, about or at least about 95% endotoxin free, about or at least about 99% endotoxin free, or about or at least about 99.99% endotoxin free. The presence of endotoxins can be detected according to routine techniques in the art, as described herein. In specific embodiments, a composition is made from a eukaryotic cell such as a mammalian or human cell in substantially serum free media. In certain embodiments, as noted herein, a composition has an endotoxin content of less than about 10 EU/mg of antibody, or less than about 5 EU/mg of antibody, less than about 3 EU/mg of antibody, or less than about 1 EU/mg of antibody.

In certain embodiments, a composition comprises less than about 10% wt/wt high molecular weight aggregates, or less than about 5% wt/wt high molecular weight aggregates, or less than about 2% wt/wt high molecular weight aggregates, or less than about or less than about 1% wt/wt high molecular weight aggregates.

Also included are protein-based analytical assays and methods, which can be used to assess, for example, protein purity, size, solubility, and degree of aggregation, among other characteristics. Protein purity can be assessed a number of ways. For instance, purity can be assessed based on primary structure, higher order structure, size, charge, hydrophobicity, and glycosylation. Examples of methods for assessing primary structure include N- and C-terminal sequencing and peptide-mapping (see, e.g., Allen et al., Biologicals. 24:255-275, 1996)). Examples of methods for assessing higher order structure include circular dichroism (see, e.g., Kelly et al., Biochim Biophys Acta. 1751:119-139, 2005), fluorescent spectroscopy (see, e.g., Meagher et al., J. Biol. Chem. 273:23283-89, 1998), FT-IR, amide hydrogen-deuterium exchange kinetics, differential scanning calorimetry, NMR spectroscopy, immunoreactivity with conformationally sensitive antibodies. Higher order structure can also be assessed as a function of a variety of parameters such as pH, temperature, or added salts. Examples of methods for assessing protein characteristics such as size include analytical ultracentrifugation and size exclusion HPLC (SEC-HPLC), and exemplary methods for measuring charge include ion-exchange chromatography and isoelectric focusing. Hydrophobicity can be assessed, for example, by reverse-phase HPLC and hydrophobic interaction chromatography HPLC. Glycosylation can affect pharmacokinetics (e.g., clearance), conformation or stability, receptor binding, and protein function, and can be assessed, for example, by mass spectrometry and nuclear magnetic resonance (NMR) spectroscopy.

As noted above, certain embodiments include the use of SEC-HPLC to assess protein characteristics such as purity, size (e.g., size homogeneity) or degree of aggregation, and/or to purify proteins, among other uses. SEC, also including gel-filtration chromatography (GFC) and gel-permeation chromatography (GPC), refers to a chromatographic method in which molecules in solution are separated in a porous material based on their size, or more specifically their hydrodynamic volume, diffusion coefficient, and/or surface properties. The process is generally used to separate biological molecules, and to determine molecular weights and molecular weight distributions of polymers. Typically, a biological or protein sample (such as a protein extract produced according to the protein expression methods provided herein and known in the art) is loaded into a selected size-exclusion column with a defined stationary phase (the porous material), preferably a phase that does not interact with the proteins in the sample. In certain aspects, the stationary phase is composed of inert particles packed into a dense three-dimensional matrix within a glass or steel column. The mobile phase can be pure water, an aqueous buffer, an organic solvent, or a mixture thereof. The stationary-phase particles typically have small pores and/or channels which only allow molecules below a certain size to enter. Large particles are therefore excluded from these pores and channels, and their limited interaction with the stationary phase leads them to elute as a "totally-excluded" peak at the beginning of the experiment. Smaller molecules, which can fit into the pores, are removed from the flowing mobile phase, and the time they spend immobilized in the stationary-phase pores depends, in part, on how far into the pores they penetrate. Their removal from the mobile phase flow causes them to take longer to elute from the column and results in a separation between the particles based on differences in their size. A given size exclusion column has a range of molecular weights that can be separated. Overall, molecules larger than the upper limit will not be trapped by the stationary phase, molecules smaller than the lower limit will completely enter the solid phase and elute as a single band, and molecules within the range will elute at different rates, defined by their properties such as hydrodynamic volume. For examples of these methods in practice with pharmaceutical proteins, see Bruner et al., Journal of Pharmaceutical and Biomedical Analysis. 15: 1929-1935, 1997.

Protein purity for clinical applications is also discussed, for example, by Anicetti et al. (Trends in Biotechnology. 7:342-349, 1989). More recent techniques for analyzing protein purity include, without limitation, the LabChip GXII, an automated platform for rapid analysis of proteins and nucleic acids, which provides high throughput analysis of titer, sizing, and purity analysis of proteins. In certain non-limiting embodiments, clinical grade proteins such as protein fragments and antibodies can be obtained by utilizing a combination of chromatographic materials in at least two orthogonal steps, among other methods (see, e.g., Therapeutic Proteins: Methods and Protocols. Vol. 308, Eds., Smales and James, Humana Press Inc., 2005). Typically, protein agents (e.g., antibodies and antigen binding fragments) are substantially endotoxin-free, as measured according to techniques known in the art and described herein.

Protein solubility assays are also included. Such assays can be utilized, for example, to determine optimal growth and purification conditions for recombinant production, to optimize the choice of buffer(s), and to optimize the choice of antibodies or antigen binding fragments thereof. Solubility or aggregation can be evaluated according to a variety of parameters, including temperature, pH, salts, and the presence or absence of other additives. Examples of solubility screening assays include, without limitation, microplate-based methods of measuring protein solubility using turbidity or other measure as an end point, high-throughput assays for analysis of the solubility of purified recombinant proteins (see, e.g., Stenvall et al., Biochim Biophys Acta. 1752:6-10, 2005), assays that use structural complementation of a genetic marker protein to monitor and measure protein folding and solubility in vivo (see, e.g., Wigley et al., Nature Biotechnology. 19:131-136, 2001), and electrochemical screening of recombinant protein solubility in *Escherichia coli* using scanning electrochemical microscopy (SECM) (see, e.g., Nagamine et al., Biotechnology and Bioengineering. 96:1008-1013, 2006), among others. Antibodies with increased solubility (or reduced aggregation) can be identified or selected for according to routine techniques in the art, including simple in vivo assays for protein solubility (see, e.g., Maxwell et al., Protein Sci. 8:1908-11, 1999).

Protein solubility and aggregation can also be measured by dynamic light scattering techniques. Aggregation is a general term that encompasses several types of interactions or characteristics, including soluble/insoluble, covalent/non-covalent, reversible/irreversible, and native/denatured interactions and characteristics. For protein therapeutics, the presence of aggregates is typically considered undesirable because of the concern that aggregates may cause an immunogenic reaction (e.g., small aggregates), or may cause adverse events on administration (e.g., particulates). Dynamic light scattering refers to a technique that can be used to determine the size distribution profile of small particles in suspension or polymers such as proteins in solution. This technique, also referred to as photon correlation spectroscopy (PCS) or quasi-elastic light scattering (QELS), uses scattered light to measure the rate of diffusion of the protein particles. Fluctuations of the scattering intensity can be observed due to the Brownian motion of the molecules and particles in solution. This motion data can be conventionally processed to derive a size distribution for the sample, wherein the size is given by the Stokes radius or hydrodynamic radius of the protein particle. The hydrodynamic size depends on both mass and shape (conformation). Dynamic scattering can detect the presence of very small amounts of aggregated protein (<0.01% by weight), even in samples that contain a large range of masses. It can also be used to compare the stability of different formulations, including, for example, applications that rely on real-time monitoring of changes at elevated temperatures. Accordingly, certain embodiments include the use of dynamic light scattering to analyze the solubility and/or presence of aggregates in a sample that contains an antibody of the present disclosure.

Although the foregoing embodiments have been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Anti-IL-11Rα Antibodies

Studies were performed to generate improved anti-IL-11Rα antibodies, relative, for example, to the antibodies described in U.S. Pat. Nos. 9,796,782; and 9,340,618—including the antibodies designated as 8E2 and TS7. For example, a potential N-linked glycosylation in $V_L$CDR3 of the TS7 antibody was eliminated to reduce heterogeneity and improve developability, and other sequence changes were made to improve binding affinity and potency. The CDR sequences of the antibodies are provided in Table A1 (supra). The antibodies were expressed in HEK293 cells and purified using protein A based chromatography using standard methodology. All antibodies were expressed in human IgG4 (S228P by EU numbering; S241P by Kabat numbering) format with kappa light chains.

Relative binding activity of the antibodies was tested by competitive ELISA using biotinylated mAbs 8E2 or TS7. Antibodies 8E2 and TS7 were biotinylated using sulfo-NHS Biotin (Thermo Fisher) per the manufacturer's instructions. IL-11R was coated onto ELISA plates (Nunc, MaxiSorp) at 2 μg/mL in PBS, and plates were blocked with 2% BSA in PBS. After washing the plate with water, antibodies to be tested were titrated across the plate in a final volume of 90 μL followed by addition of 10 μL of biotinylated 8E2 or biotinylated TS7, as indicated in Table E1 (0.1 μg/mL final concentration) to each well. Plates were incubated for 2 hours on a plate-shaker, followed by washing and addition of 100 μL/well of streptavidin-HRP (Jackson ImmunoResearch, 1/1000 dilution). After a further 1 hour incubation, plates were washed, developed with Ultra-TMB HRP substrate (Thermo Fisher), and stopped by the addition of 50 μL/well of 2 M sulfuric acid. Plates were read at 450 nm on an iD5 plate reader (Molecular Devices).

As shown in Table E1 below, many of the tested antibodies were shown to have increased binding to human IL-11Rα relative to that of the 8E2 antibody and the TS7 antibody.

TABLE E1

Competitive ELISA for binding strength relative to 8E2 and TS7

| Competitor | 8E2-bio IC$_{50}$ (µg/mL) | TS7-bio IC$_{50}$ (µg/mL) |
|---|---|---|
| 8E2 | 22 | |
| TS7 | 3.1 | 6.0 |
| mAb1 | >10 | |
| mAb2 | >30 | |
| mAb3 | 2.8 | |
| mAb4 | 5.5 | |
| mAb5 | 1.4 | 2.1 |
| mAb6 | 1.5 | |
| mAb7 | | 6.9 |
| mAb8 | | 6.2 |
| mAb9 | | 2.3 |
| mAb10 | | >15 |
| mAb11 | | >15 |
| mAb12 | | 3.6 |
| mAb13 | | 2.3 |
| mAb14 | | 2.0 |
| mAb15 | | 1.7 |

Kinetic binding analysis of mAbs was tested to determine antigen binding affinity using biolayer interferometry on an Octet RED96e instrument. mAbs were loaded onto protein G biosensors (FortéBio) in 10×kinetics buffer consisting of PBS, 0.1% BSA, 0.02% polysorbate 20 (TWEEN™) for 120 seconds to achieve a spectral shift value of 0.8 to 1.2 nm. Association was carried out in the presence of a 2-fold dilution series of hIL-11Rα and was allowed to proceed for 120 seconds; dissociation was measured for 300 to 1200 seconds. Dilution series started at 100 nM for weaker variants or 10 nM for the most potent mAbs.

As shown in Table E2 below, mAb5, mAb6, mAb7, mAb8, mAb9, mAb12, mAb13, mAb14, and mAb15 had very high binding affinity, beyond the ability of the instrument to determine an accurate off-rate (kd).

TABLE E2

Kinetic binding analysis of mAbs to IL-11R using biolayer interferometry

| Antibody | ka (1/Ms) | kd (1/s) | K$_D$ (M) |
|---|---|---|---|
| mAb5 | 6.37E+04 | <1.0E−07 | <1.0E−12 |
| mAb6 | 8.00E+05 | <1.0E−07 | <1.0E−12 |
| mab7 | 6.35E+04 | <1.0E−07 | <1.0E−12 |
| mab8 | 6.51E+04 | <1.0E−07 | <1.0E−12 |
| mab9 | 6.22E+04 | <1.0E−07 | <1.0E−12 |
| mab10 | 8.40E+05 | 4.16E−04 | 4.96E−10 |
| mab11 | 3.29E+04 | 1.81E−02 | 5.50E−07 |
| mab12 | 5.81E+04 | <1.0E−07 | <1.0E−12 |
| mab13 | 6.67E+04 | <1.0E−07 | <1.0E−12 |
| mab14 | 3.37E+04 | <1.0E−07 | <1.0E−12 |
| mab15 | 8.40E+04 | <1.0E−07 | <1.0E−12 |

Further testing of the lead mAbs was carried out using a cell-based reporter assay. IL-11 is reported to signal through the STAT3 and ERK pathways. Therefore, a STAT3 reporter cell line in which firefly luciferase gene expression is driven by STAT3 response elements located upstream of a minimal TATA promoter was selected to analyze mAb functional activity. In these cells, IL-11 can activate the endogenous STAT3 allowing it to bind to the STAT3 response elements, inducing transcription of the luciferase reporter gene and resulting in readily detectable luciferase expression. Antibodies to IL-11R which block IL-11 signaling should inhibit expression of IL-11 driven luciferase in these cells.

The STAT3 Reporter (Luciferase)—HEK293 cell line (BPS Bioscience, catalog #79800-P) was grown, passaged, and assayed as per manufacturer's protocols. Cells were added at 25,000 cells per well in a 96-well microtiter dish and incubated at 37° C. for 30-45 min. in 5% CO$_2$ humidified air. Anti-IL-11R mAbs were added as a 3-fold dilution series in duplicate columns or rows, and plates were returned to the incubator for an additional 1 h at 37° C. after which 40 ng/mL IL-11 was added to each well to initiate the signal transduction cascade and luciferase production. Plates were incubated for 18-24 hours at 37° C. and luciferase was detected using a One-Step Luciferase Assay System (BPS Bioscience, cat. no. 60690-1) as per manufacturer's instructions.

As shown in Table E3, TS7 is significantly more potent than 8E2, and mAbs, mAb9, and mAb13 are more potent at inhibiting IL-11 signaling than either of TS7 or 8E2. In agreement with the ELISA data, mAb7, mAb8, mAb10, and mAb11 were less potent than TS7, and mAb12, mAb14, and mAb15 were comparable in potency to TS7. The results for mAb6 were variable in this assay, but the ELISA and Octet data above suggest mAb6 is also a potent mAb.

TABLE E3

Cell-based reporter assay measuring relative potency for inhibiting IL-11 IC$_{50}$ (µg/mL)

| Antibody | Assay 1 | Assay 2 | Mean |
|---|---|---|---|
| 8E2 | >50 | 22.8 | >36.4 |
| TS7 | 0.15 | 0.42 | 0.28 |
| mAb5 | 0.16 | 0.18 | 0.17 |
| mAb6 | 11.0 | 0.39 | 5.70 |
| mab7 | 1.00 | | 1.00 |
| mab8 | 0.67 | 1.25 | 0.96 |
| mab9 | 0.11 | 0.10 | 0.10 |
| mab10 | 2.00 | | 2.00 |
| mab11 | >100 | | >100 |
| mab12 | 0.42 | 0.39 | 0.41 |
| mab13 | 0.05 | 0.19 | 0.12 |
| mab14 | 0.39 | 0.28 | 0.34 |
| mab15 | 0.38 | 0.33 | 0.36 |

A further series of antibodies were designed in which the residue at Kabat position 31 of the heavy chain was varied (mAbs 16-32). In this case an alternate biolayer interferometry assay was used to initially rank the antibodies compared to mAb5, the closest relative in sequence to mAbs 16-32. MAbs were loaded onto anti-human constant domain (AHC) biosensors (FortéBio) in 10×kinetics buffer consisting of PBS, 0.1% BSA, 0.02% polysorbate 20 (TWEEN™) for 120 s to achieve a spectral shift value of 0.8 to 1.2 nm. Association was carried out in the presence of 2-fold dilution series of hIL-11R and was allowed to proceed for 120 s. Dilution series started 10 nM. The dissociation in 10×kinetics buffer for 1200 s. Binding kinetic measurements were taken on an Octet RED96e instrument.

As shown in Table E4, initial qualitative assessment identified additional antibodies with high potency either similar to or better than mAb5. More detailed kinetic measurements were taken for mAb21, mAb23, mAb29, and mAb31 compared to mAb5, which confirmed further improved potency for these mAbs. Further testing of these mAbs by ELISA confirmed the improved potency of the selected mAbs.

TABLE E4

| mAb | qualitative assessment | $K_D$ (pM) | ka (1/Ms) | kd (1/s) |
|---|---|---|---|---|
| 5 | comparator | 50 pM | 4.90E+05 | 2.50E−05 |
| 16 | similar | ND | ND | ND |
| 17 | decreased | ND | ND | ND |
| 18 | decreased | ND | ND | ND |
| 19 | similar | ND | ND | ND |

TABLE E4-continued

| mAb | qualitative assessment | $K_D$ (pM) | ka (1/Ms) | kd (1/s) |
|---|---|---|---|---|
| 20 | similar | ND | ND | ND |
| 21 | improved/increased | <30 pM | 7.50E+05 | off-scale |
| 22 | similar | ND | ND | ND |
| 23 | improved/increased | <30 pM | 7.20E+05 | off-scale |
| 24 | similar | ND | ND | ND |
| 25 | similar | ND | ND | ND |
| 26 | decreased | ND | ND | ND |
| 27 | decreased | ND | ND | ND |
| 28 | similar | ND | ND | ND |
| 29 | improved/increased | 30 pM | 6.10E+05 | 1.80E−05 |
| 30 | decreased | ND | ND | ND |
| 31 | improved/increased | <30 pM | 6.90E+05 | off-scale |
| 32 | similar | ND | ND | ND |

All publications, patent applications, and issued patents cited in this specification are herein incorporated by reference as if each individual publication, patent application, or issued patent were specifically and individually indicated to be incorporated by reference.

Example 2

Activity of Anti-IL-11Rα, Antibodies in a Fibrotic Human Precision-Cut Lung Slice Model Studies were performed to evaluate the effect of the mAb5 antibody on biomarkers reflecting ECM remodeling in a fibrotic human precision-cut lung slice (PCLS) model. The anti-fibrotic effect was investigated at three different concentrations in human ex vivo lung tissue slices prepared from pulmonary fibrosis patients.

Materials and Methods

Tissue slices were prepared from the subpleural and central region of the fibrotic lung from two human end-stage donors with pulmonary fibrosis (IPF and secondary fibrosis) (see, for example, Hess et al., Toxicol In Vitro. 32:347-61, 2016). For both donors, lung tissue samples from two different regional areas (subpleural and central) were used to generate tissue cores used for PCLS. Adjacent cores were used to achieve serial PCLS for the analysis of one treatment as compared to medium treated PCLS from the same cores. This enables the comparison of densely packed fibrotic areas with fibrotic foci with less affected areas. To ensure the fibrotic status, clinical/demographic information for each patient is provided.

Experimental treatments included are listed in Table E5. Each treatment was tested with three replicates for each lung region and for each donor.

TABLE E5

| Treatment | Timepoint | Samples |
|---|---|---|
| mAb5 IL11RA Ab 0.3 µg/mL | 48 hours | Supernatant and Tissue |
| mAb5 IL11RA Ab 3.0 µg/mL | 48 hours | Supernatant and Tissue |
| mAb5 IL11RA Ab 30 µg/mL | 48 hours | Supernatant and Tissue |
| Isotype control 30 µg/mL | 48 hours | Supernatant and Tissue |
| Nintedanib 1 µM | 48 hours | Supernatant and Tissue |
| Medium control (PCLS w/o treatment) | 48 hours | Supernatant and Tissue |
| DMEM/F12 (Medium background w/o PCLS) | 48 hours | Supernatant and Tissue |

Preparation and incubation of precision-cut lung slices. Lung lobes were canuled and filled with 37° C. warm 2% low-melting agarose/medium solution. Filled lobes were cooled on ice to polymerise agarose. Tissue cores with a diameter of 8 mm were prepared and cut into approximately 300 µm thick slices using a microtome (Krumdieck tissue slicer, Alabama Research and Development, Muniford, AL, USA or Vibratome OTS-5000, Science Services GmbH, Munich) in Earle's Balanced Salts Solution (EBSS). Tissue slices were incubated in Dulbecco's modified Eagle's medium/nutrient mixture F-12 Ham (DMEM) with L-glutamine and 15 mM HEPES without phenol red. Tissue slices were transferred into petri dishes and washed with DMEM for 2 hours. Medium was changed four times every 30 minutes in order to remove cell debris.

Two PCLS per well were left over night in 500 µL DMEM in 24-well plates for a final washing step. Next day, PCLS were treated with experimental treatments or controls (see Table E5) in 250 µl DMEM/F-12 culture medium for 48 hours under normal cell culture conditions (37° C., 5% $CO_2$). Medium contained 100 units/mL penicillin and 100 µg/mL streptomycin and was not supplemented with fetal calf serum.

After incubation for 48 hours, supernatants were collected, proteinase inhibitor cocktail (0.2%) was added and samples were frozen to −80° C. Additionally, the two PCLS from each well were transferred to a 2 mL safe-lock tube, snap-frozen in liquid nitrogen immediately, and stored at −80° C. Samples from the three replicates for each condition were not pooled.

The viability and responsiveness of the tissue to immune stimulators was confirmed in a quality control sample where PCLS was incubated with the mitogen 100 ng/mL lipopolysaccharide (LPS). Following 48 hours incubation, assessment of viability by lactate dehydrogenase (LDH) activity and pro-inflammatory response by IL-1$ was performed.

Tissue viability. The viability of the lung tissue was assessed to ensure sufficient quality of the PCLS. For quality control samples, LDH activity was determined with a commercial enzymatic assay in supernatants after incubation. An increase of the amount of dead or plasma membrane-damaged cells in PCLS will result in an increase of LDH enzyme activity in the culture supernatant. Octylphenol ethoxylate (TRITON™ X-100) (1% in PBS) treated PCLS were investigated as reference control. 50 µL samples were incubated with 50 μL LDH reagent for 20 minutes at room temperature. Absorbance was measured at 490 nm and 630 nm as reference wavelength using a microplate reader. All tests were performed as single measurements per well. Due to the dense tissue material of fibrotic PCLS, absorbance values measured for the octylphenol ethoxylate (TRITON™ X-100) control were at maximum. Therefore, 1:10 dilutions of these controls were tested in parallel to achieve appropriate values within the range of the detection spectra for calculation of the relative LDH release of the samples.

Tissue responsiveness. The general responsiveness of the lung tissue to treatment was assessed to ensure optimal condition of the PCLS. For quality control samples, PCLS were lysed with octylphenol ethoxylate (TRITON™ X-100) (1% in PBS) for one hour, whereafter intrinsic IL-1$ levels were assessed using ELISA from R&D according to the manufacturer's instructions. The photometric measurement was performed at 450 nm and a reference wavelength of 570 nm using a microplate reader. The IL-1β concentration was normalized to total protein concentration of PCLS determined by BCA assay.

Tissue appearance. Macroscopic appearance of the tissue as well as location of cores used to generate PCLS were recorded by photography. Tissue cores adjacent to the ones used for PCLS preparation were fixed in 10% formalin and subsequently embedded in paraffin. Paraffin-embedded tissue sections were further processed into slices for staining with hematoxylin and eosin (H&E) to assess fibrotic remodeling.

Extracellular matrix remodeling evaluation. Biomarkers that reflect ECM remodeling were assessed in supernatant by Nordic Bioscience using the following competitive ELISA: PRO-C6 (C-terminal of type VI collagen C5 domain released as type VI collagen is incorporated into the matrix; measured on mesoscale platform [hsPRO-C6]): Reflects type VI collagen formation. Type VI collagen is a beaded filament collagen mainly found in the interface between the interstitial matrix and the basement membrane.

Statistics. Biomarker data are presented as scatter plots with indication of median and interquartile range (IQR). Data are presented as raw biomarker values for each region and donor. Pooled data are presented as percentage of the "no treatment" control, calculated for individual regions and donors. Statistical significant differences were evaluated on pooled data by Kruskal-Wallis with Dunn's multiple comparisons test, comparing to the "no treatment" control. Adjusted p-values are shown as: *p<0.05, p<0.01, *p<0.001, ****p<0.0001.

Results

Fibrotic Status. Human PCLS were generated from lung tissue from two donors with pulmonary fibrosis. The pathological report provided after the completion of the study stated that the fibrotic tissue represents a clear UIP pattern and would be compatible with IPF (see Table E6).

TABLE E6

| Donor 1 | Donor 2 |
|---|---|
| 62 years old male<br>Bilateral lung explant with:<br>advanced interstitial fibrosis with architectural disturbance, bronchiolisation, myogenic metaplasia and multifocal fibroblastic foci with emphasis on the pulmonary sublobes<br>mild chronic and focal (lower lobe left) catarrhal bronchitis and bronchiolitis<br>still low-grade pulmonary artery sclerosis (see commentary).<br>Comment:<br>The present findings fulfil the morphological criteria of a UIP pattern (definite UIP according to ATS/ERS) and are-especially with clear accentuation of the pulmonary basement-suitable for an idiopathic pulmonary fibrosis (IPF). No evidence of malignancy. | 56 years old male<br>Bilateral lung explant with advanced interstitial fibrosis with numerous fibroblastic foci, architectural disorder of the lung parenchyma, bronchial metaplasia and myogenic metaplasia corresponding to a UIP pattern,<br>chronic and florid catarrhal bronchitis/iolitis with signs of secretion retention and multifocal transition to florid bronchopneumonia,<br>mild pulmonary artery sclerosis, dust granulomas in the hilar lymph nodes.<br>Comment:<br>The findings are well compatible with idiopathic pulmonary fibrosis (IPF) in a far advanced stage. No evidence of malignancy. |

Figure 1A:
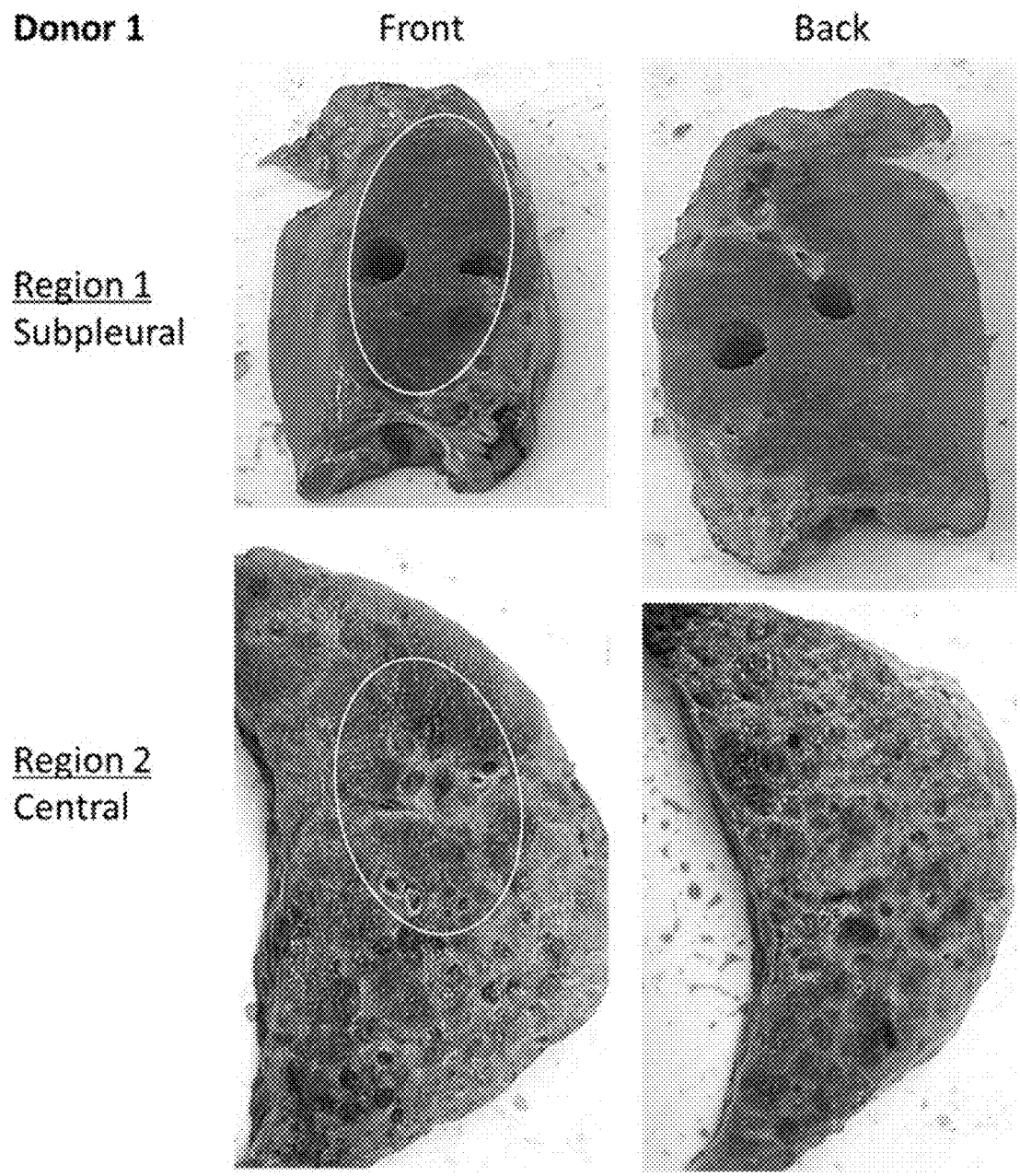
FIGS. 1A-1B shows the gross appearance of lung tissue from Donor 1 (1A) and Donor 2 (1B).
Figure 1B:
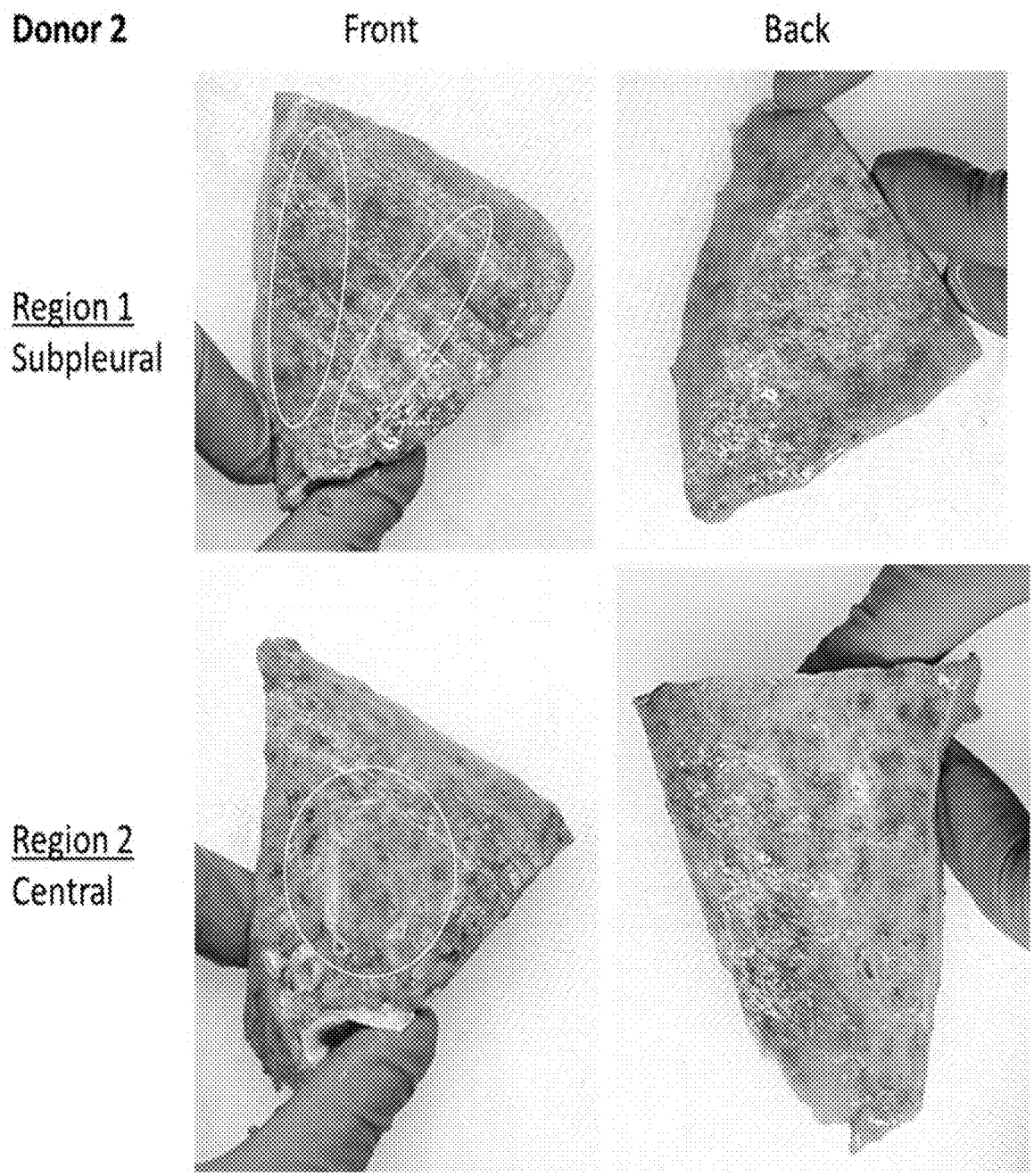
Figure 2A:
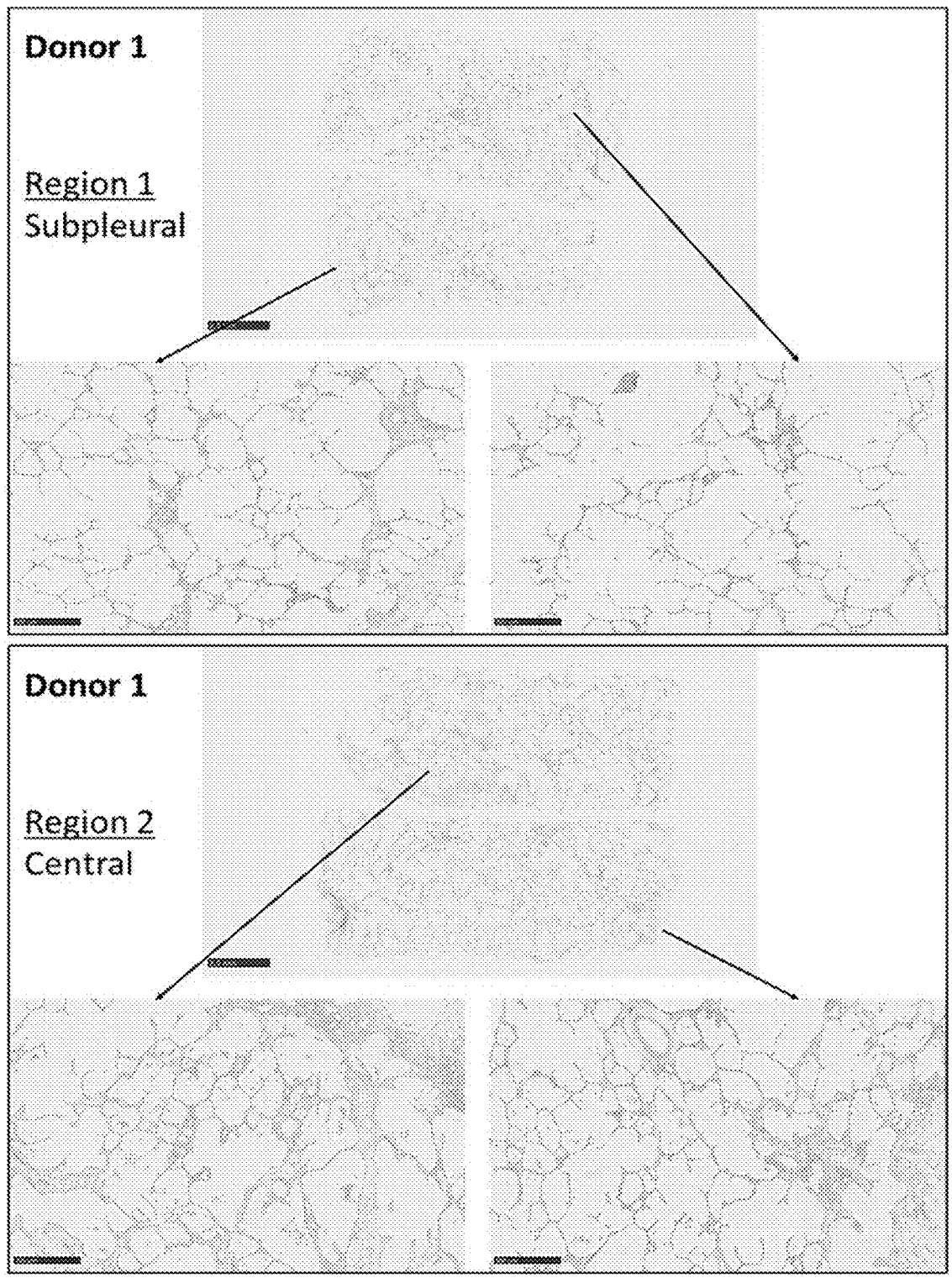
FIGS. 2A-2B show the hematoxylin and eosin staining of the fibrotic lung tissue from donor 1 (2A, top subpleural; bottom central) and Donor 2 (2B, top subpleural; bottom central). Staining was done on tissue adjacent to the PCLS tissue cores. Representative overview pictures are shown.
Figure 2B:
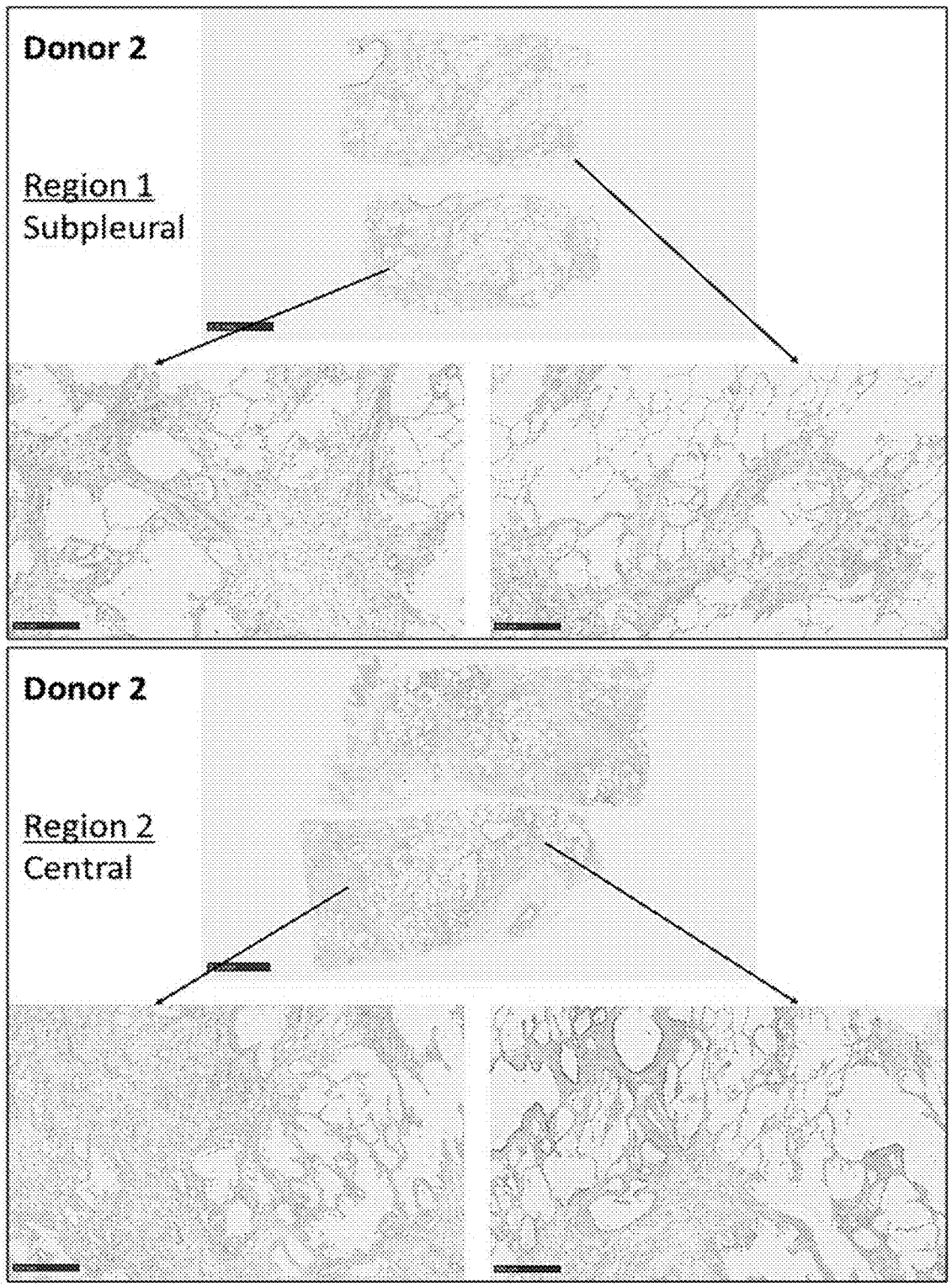

Tissue Appearance. The PCLS were prepared from different regions of the fibrotic lung. FIGS. 1A-1B shows images of the lungs of each donor and the regions used, where drawn circles marks the areas of tissue that were used to generate PCLS. Adjacent tissue cores from the same lung region as that used for PCLS were subsequently prepared for H&E staining to assess fibrotic remodeling of the tissue (see FIGS. 2A-2B). Donor 2 appears to have more extensive tissue changes than donor 1 which is in accordance with the statement in the pathological report that donor 2 tissue is compatible with IPF in a far advanced stage.

Figure 3A:
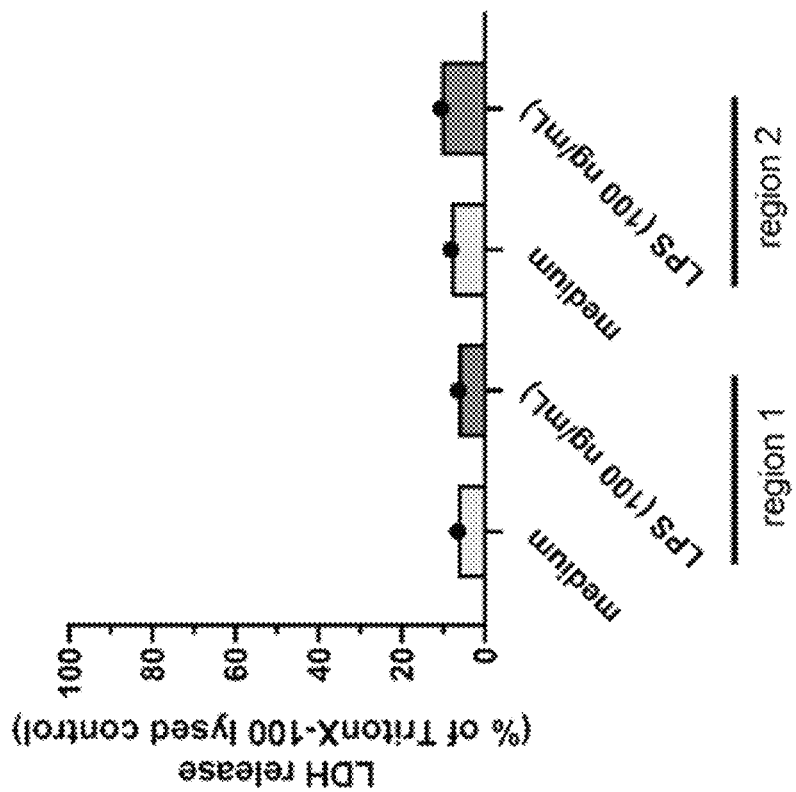
FIGS. 3A-3B show the tissue viability of untreated (medium) and LPS treated Precision-Cut Lung Slices (PCLS)
Figure 3B:
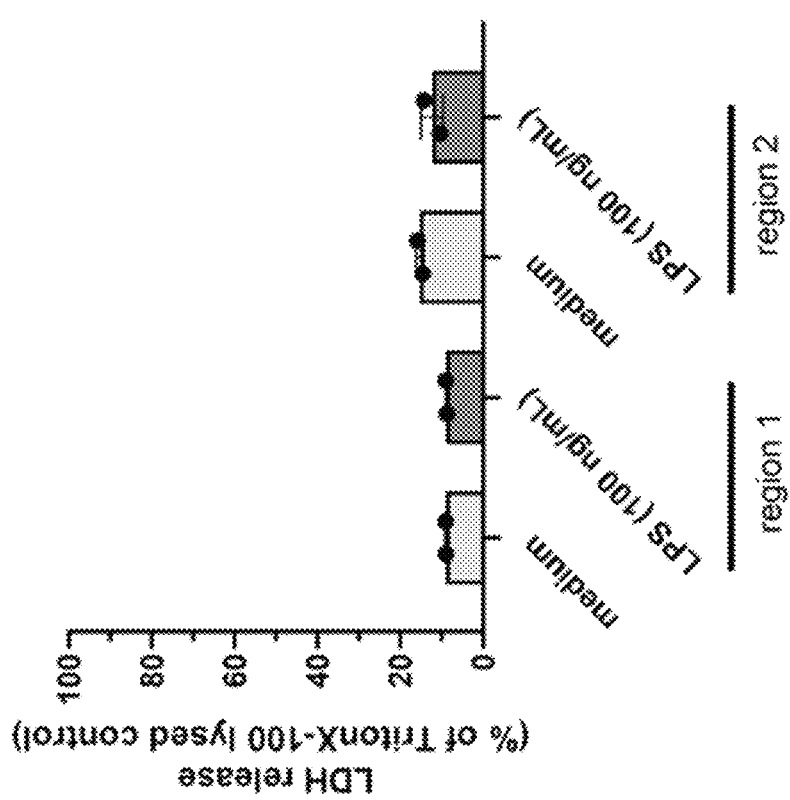

Tissue Viability. Tissue viability of quality control samples (LPS) was measured by LDH release after 48 hours incubation. LDH release <20% of the octylphenol ethoxylate (TRITON™ X) lysed control was observed for all samples, indicating that the tissue was viable over the experimental period of 48 hours (see FIGS. 3A-3B).

Tissue Responsiveness. Tissue responsiveness of quality control sample (LPS) was analysed by IL-1β expression. Analysis showed that human fibrotic lung tissue from both donors responded to the pro-inflammatory stimuli LPS, identified by the upregulated expression of IL-1β after 48 hours (see FIGS. 4A-4B).

Extracellular Matrix Remodeling. Type VI collagen formation was evaluated by PRO-C6. Medium background levels of PRO-C6 were low and at the level of lower limit of detection for the assay. Donor 1 showed lower levels of PRO-C6 as compared to donor 2, with levels quite close to the medium background.

As shown in FIG. 5, the pooled PRO-C6 data for all donors and regions showed that median levels of PRO-C6 for nintedanib and all concentrations of mAb5 (anti-IL11R) were decreased as compared to the no treatment (media) control. mAb5 reduced PRO-C6 in a dose-dependent manner. The isotype control did not show a change in median PRO-C6 levels as compared to the no treatment (media) control, and even tended to increase slightly.

Based on the effects of nintedanib, the lung slices were responsive to anti-fibrotic treatment as ECM remodeling could be reduced. Overall, tendencies for effects on ECM remodeling were observed with the mAb5 anti-IL-11Rα antibody. Especially interesting were the dose-related reductions of type VI collagen formation (PRO-C6) by the mAb5 antibody. In several cases, the mAb5 antibody showed better effects on ECM remodeling relative to the approved therapy nintedanib, strengthening the conclusion that this antibody has anti-fibrotic effects.

The invention claimed is:

1. A method of treating an IL-11-associated or IL-11-mediated fibrotic disease or condition in a subject in need thereof, comprising administering to the subject an antibody, or antigen binding fragment thereof, which binds to interleukin-11 receptor subunit α (IL-11Rα), wherein the antibody, or antigen binding fragment thereof, comprises a heavy chain variable region ($V_H$) and a light chain variable region ($V_L$), wherein the $V_H$ comprises complementary determining region $V_H$CDR1, $V_H$CDR2, and $V_H$CDR3 sequences and the $V_L$ comprises complementary determining region $V_L$CDR1, $V_L$CDR2, and $V_L$CDR3 sequences, and wherein:

a. the $V_H$CDR1, $V_H$CDR2, and $V_H$CDR3 sequences comprise SEQ ID NOs: 25-27, respectively, and the V$_L$CDR1, V$_L$CDR2, and V$_L$CDR3 sequences comprise SEQ ID NOs: 28-30, respectively;
b. the V$_H$CDR1, V$_H$CDR2, and V$_H$CDR3 sequences comprise SEQ ID NOs: 91-93, respectively, and the V$_L$CDR1, V$_L$CDR2, and V$_L$CDR3 sequences comprise SEQ ID NOs: 94-96, respectively;
c. the V$_H$CDR1, V$_H$CDR2, and V$_H$CDR3 sequences comprise SEQ ID NOs: 97-99, respectively, and the V$_L$CDR1, V$_L$CDR2, and V$_L$CDR3 sequences comprise SEQ ID NOs: 100-102, respectively;
d. the V$_H$CDR1, V$_H$CDR2, and V$_H$CDR3 sequences comprise SEQ ID NOs: 103-105, respectively, and the V$_L$CDR1, V$_L$CDR2, and V$_L$CDR3 sequences comprise SEQ ID NOs: 106-108, respectively;
e. the V$_H$CDR1, V$_H$CDR2, and V$_H$CDR3 sequences comprise SEQ ID NOs: 109-111, respectively, and the V$_L$CDR1, V$_L$CDR2, and V$_L$CDR3 sequences comprise SEQ ID NOs: 112-114, respectively;
f. the V$_H$CDR1, V$_H$CDR2, and V$_H$CDR3 sequences comprise SEQ ID NOs: 115-117, respectively, and the V$_L$CDR1, V$_L$CDR2, and V$_L$CDR3 sequences comprise SEQ ID NOs: 118-120, respectively;
g. the V$_H$CDR1, V$_H$CDR2, and V$_H$CDR3 sequences comprise SEQ ID NOs: 121-123, respectively, and the V$_L$CDR1, V$_L$CDR2, and V$_L$CDR3 sequences comprise SEQ ID NOs: 124-126, respectively;
h. the V$_H$CDR1, V$_H$CDR2, and V$_H$CDR3 sequences comprise SEQ ID NOs: 127-129, respectively, and the V$_L$CDR1, V$_L$CDR2, and V$_L$CDR3 sequences comprise SEQ ID NOs: 130-132, respectively;
i. the V$_H$CDR1, V$_H$CDR2, and V$_H$CDR3 sequences comprise SEQ ID NOs: 133-135, respectively, and the V$_L$CDR1, V$_L$CDR2, and V$_L$CDR3 sequences comprise SEQ ID NOs: 136-138, respectively;
j. the V$_H$CDR1, V$_H$CDR2, and V$_H$CDR3 sequences comprise SEQ ID NOs: 139-141, respectively, and the V$_L$CDR1, V$_L$CDR2, and V$_L$CDR3 sequences comprise SEQ ID NOs: 142-144, respectively;
k. the V$_H$CDR1, V$_H$CDR2, and V$_H$CDR3 sequences comprise SEQ ID NOs: 145-147, respectively, and the V$_L$CDR1, V$_L$CDR2, and V$_L$CDR3 sequences comprise SEQ ID NOs: 148-150, respectively;
l. the V$_H$CDR1, V$_H$CDR2, and V$_H$CDR3 sequences comprise SEQ ID NOs: 151-153, respectively, and the V$_L$CDR1, V$_L$CDR2, and V$_L$CDR3 sequences comprise SEQ ID NOs: 154-156, respectively;
m. the V$_H$CDR1, V$_H$CDR2, and V$_H$CDR3 sequences comprise SEQ ID NOs: 157-159, respectively, and the V$_L$CDR1, V$_L$CDR2, and V$_L$CDR3 sequences comprise SEQ ID NOs: 160-162, respectively;
n. the V$_H$CDR1, V$_H$CDR2, and V$_H$CDR3 sequences comprise SEQ ID NOs: 163-165, respectively, and the V$_L$CDR1, V$_L$CDR2, and V$_L$CDR3 sequences comprise SEQ ID NOs: 166-168, respectively;
o. the V$_H$CDR1, V$_H$CDR2, and V$_H$CDR3 sequences comprise SEQ ID NOs: 169-171, respectively, and the V$_L$CDR1, V$_L$CDR2, and V$_L$CDR3 sequences comprise SEQ ID NOs: 172-174, respectively;
p. the V$_H$CDR1, V$_H$CDR2, and V$_H$CDR3 sequences comprise SEQ ID NOs: 175-177, respectively, and the V$_L$CDR1, V$_L$CDR2, and V$_L$CDR3 sequences comprise SEQ ID NOs: 178-180, respectively;
q. the V$_H$CDR1, V$_H$CDR2, and V$_H$CDR3 sequences comprise SEQ ID NOs: 181-183, respectively, and the V$_L$CDR1, V$_L$CDR2, and V$_L$CDR3 sequences comprise SEQ ID NOs: 184-186, respectively; or
r. the V$_H$CDR1, V$_H$CDR2, and V$_H$CDR3 sequences comprise SEQ ID NOs: 187-189, respectively, and the V$_L$CDR1, V$_L$CDR2, and V$_L$CDR3 sequences comprise SEQ ID NOs: 190-192, respectively.

2. The method of claim 1, wherein the antibody, or antigen binding fragment thereof, binds to a fibronectin domain III of human IL-11Rα, or approximately residues 112-219 of SEQ ID NO: 257.

3. The method of claim 1, wherein:
a. the VH comprises a sequence of SEQ ID NO: 201, or a sequence comprising at least 80% sequence identity thereto; and the VL comprises a sequence of SEQ ID NO: 202, or a sequence comprising at least 80% sequence identity thereto;
b. the VH comprises a sequence of SEQ ID NO: 223, or a sequence comprising at least 80% sequence identity thereto; and the VL comprises a sequence of SEQ ID NO: 224, or a sequence comprising at least 80% sequence identity thereto;
c. the VH comprises a sequence of SEQ ID NO: 225, or a sequence comprising at least 80% sequence identity thereto; and the VL comprises a sequence of SEQ ID NO: 226, or a sequence comprising at least 80% sequence identity thereto;
d. the VH comprises a sequence of SEQ ID NO: 227, or a sequence comprising at least 80% sequence identity thereto; and the VL comprises a sequence of SEQ ID NO: 228, or a sequence comprising at least 80% sequence identity thereto;
e. the VH comprises a sequence of SEQ ID NO: 229, or a sequence comprising at least 80% sequence identity thereto; and the VL comprises a sequence of SEQ ID NO: 230, or a sequence comprising at least 80% sequence identity thereto;
f. the VH comprises a sequence of SEQ ID NO: 231, or a sequence comprising at least 80% sequence identity thereto; and the VL comprises a sequence of SEQ ID NO: 232, or a sequence comprising at least 80% sequence identity thereto;
g. the VH comprises a sequence of SEQ ID NO: 233, or a sequence comprising at least 80% sequence identity thereto; and the VL comprises a sequence of SEQ ID NO: 234, or a sequence comprising at least 80% sequence identity thereto;
h. the VH comprises a sequence of SEQ ID NO: 235, or a sequence comprising at least 80% sequence identity thereto; and the VL comprises a sequence of SEQ ID NO: 236, or a sequence comprising at least 80% sequence identity thereto;
i. the VH comprises a sequence of SEQ ID NO: 237, or a sequence comprising at least 80% sequence identity thereto; and the VL comprises a sequence of SEQ ID NO: 238, or a sequence comprising at least 80% sequence identity thereto;
j. the VH comprises a sequence of SEQ ID NO: 239, or a sequence comprising at least 80% sequence identity thereto; and the VL comprises a sequence of SEQ ID NO: 240, or a sequence comprising at least 80% sequence identity thereto;
k. the VH comprises a sequence of SEQ ID NO: 241, or a sequence comprising at least 80% sequence identity thereto; and the VL comprises a sequence of SEQ ID NO: 242, or a sequence comprising at least 80% sequence identity thereto;
l. the VH comprises a sequence of SEQ ID NO: 243, or a sequence comprising at least 80% sequence identity thereto; and the VL comprises a sequence of SEQ ID NO: 244, or a sequence comprising at least 80% sequence identity thereto;

m. the VH comprises a sequence of SEQ ID NO: 245, or a sequence comprising at least 80% sequence identity thereto; and the VL comprises a sequence of SEQ ID NO: 246, or a sequence comprising at least 80% sequence identity thereto;

n. the VH comprises a sequence of SEQ ID NO: 247, or a sequence comprising at least 80% sequence identity thereto; and the VL comprises a sequence of SEQ ID NO: 248, or a sequence comprising at least 80% sequence identity thereto;

o. the VH comprises a sequence of SEQ ID NO: 249, or a sequence comprising at least 80% sequence identity thereto; and the VL comprises a sequence of SEQ ID NO: 250, or a sequence comprising at least 80% sequence identity thereto;

p. the VH comprises a sequence of SEQ ID NO: 251, or a sequence comprising at least 80% sequence identity thereto; and the VL comprises a sequence of SEQ ID NO: 252, or a sequence comprising at least 80% sequence identity thereto;

q. the VH comprises a sequence of SEQ ID NO: 253, or a sequence comprising at least 80% sequence identity thereto; and the VL comprises a sequence of SEQ ID NO: 254, or a sequence comprising at least 80% sequence identity thereto; or r. the VH comprises a sequence of SEQ ID NO: 255, or a sequence comprising at least 80% sequence identity thereto; and the VL comprises a sequence of SEQ ID NO: 256, or a sequence comprising at least 80% sequence identity thereto.

4. The method claim 1, wherein the antibody, or antigen binding fragment thereof, comprises an IgA (including subclasses IgA1 and IgA2), IgD, IgE, IgG (including subclasses IgG1, IgG2, IgG3, and IgG4), or IgM Fc domain, optionally a human Fc domain, a hybrid and/or variant thereof.

5. The method claim 1, wherein the antibody, or antigen binding fragment thereof, comprises a human IgG1 or IgG4 Fc domain, or a hybrid, variant or modified Fc domain thereof, optionally wherein the human IgG4 Fc domain comprises SEQ ID NO: 258 or 259.

6. The method of claim 1, wherein the antibody, or antigen binding fragment thereof, is a monoclonal antibody.

7. The method of claim 1, wherein the antibody, or antigen binding fragment thereof, is a humanized antibody, optionally wherein the antibody, or antigen binding fragment thereof, is a humanized monoclonal antibody that comprises a human IgG4 Fc domain with an S228P mutation (EU numbering).

8. The method of claim 1, wherein the antibody, or antigen binding fragment thereof, is selected from an Fv fragment, a single chain Fv (scFv) polypeptide, an adnectin, an anticalin, an aptamer, an avimer, a camelid antibody, a designed ankyrin repeat protein (DARPin), a minibody, a nanobody, and a unibody.

9. The method of claim 5, wherein the antibody comprising the modified Fc domain exhibits an increased half-life relative to a corresponding wild-type Fc sequence.

10. The method of claim 9, wherein the modified Fc domain comprises one or more of substitutions M252Y, S254T, and T256E or a residue corresponding thereto, relative to the wild-type Fc sequence, according to EU numbering.

11. The method of claim 5, wherein the antibody comprising the modified Fc domain exhibits low effector function in humans.

12. The method of claim 11, wherein the antibody comprising the modified Fc domain exhibits one or more of the following: decreased complement fixation or activation, decreased C1q binding affinity, decreased CDC-related activity, decreased FcR binding affinity, decreased ADCC-related activity, and decreased ADCP-related activity, relative to a corresponding wild-type Fc sequence.

13. The method of claim 11, wherein the modified Fc domain comprises one or more of substitutions L234A, L235A, and P329S or a residue corresponding thereto, relative to the wild-type Fc sequence, according to EU numbering.

14. The method of claim 5, wherein the antibody comprising the modified Fc domain exhibits an increased half-life relative to a corresponding wild-type Fc sequence and low effector function in humans.

15. The method of claim 14, wherein the modified Fc domain exhibits one or more of the following: decreased complement fixation or activation, decreased C1q binding affinity, decreased CDC-related activity, decreased FcR binding affinity, decreased ADCC-related activity, and decreased ADCP-related activity, relative to a corresponding wild-type Fc sequence.

16. The method of claim 15, wherein the modified Fc domain comprises one or more of substitutions M252Y, S254T, T256E, L234A, L235A, and P329S or a residue corresponding thereto, relative to the wild-type Fc sequence, according to EU numbering.

* * * * *

```
                           SEQUENCE LISTING

Sequence total quantity: 259
SEQ ID NO: 1            moltype = AA   length = 5
FEATURE                 Location/Qualifiers
source                  1..5
                        mol_type = protein
                        organism = synthetic construct
REGION                  1..5
                        note = mAb1 VH CDR1
SEQUENCE: 1
WYSMT                                                                   5

SEQ ID NO: 2            moltype = AA   length = 17
FEATURE                 Location/Qualifiers
source                  1..17
                        mol_type = protein
                        organism = synthetic construct
REGION                  1..17
                        note = mAb1 VH CDR2
SEQUENCE: 2
SIVPSGGHTQ YADSVKG                                                      17

SEQ ID NO: 3            moltype = AA   length = 9
FEATURE                 Location/Qualifiers
source                  1..9
                        mol_type = protein
                        organism = synthetic construct
REGION                  1..9
                        note = mAb1 VH CDR3
SEQUENCE: 3
GPDWGSFDL                                                               9

SEQ ID NO: 4            moltype = AA   length = 11
FEATURE                 Location/Qualifiers
source                  1..11
                        mol_type = protein
                        organism = synthetic construct
REGION                  1..11
                        note = mAb1 VL CDR1
SEQUENCE: 4
QASQDINNYL N                                                            11

SEQ ID NO: 5            moltype = AA   length = 7
FEATURE                 Location/Qualifiers
source                  1..7
                        mol_type = protein
                        organism = synthetic construct
REGION                  1..7
                        note = mAb1 VL CDR2
SEQUENCE: 5
DASNLQT                                                                 7

SEQ ID NO: 6            moltype = AA   length = 9
FEATURE                 Location/Qualifiers
source                  1..9
                        mol_type = protein
                        organism = synthetic construct
REGION                  1..9
                        note = mAb1 VL CDR3
SEQUENCE: 6
QQHESQSPT                                                               9

SEQ ID NO: 7            moltype = AA   length = 5
FEATURE                 Location/Qualifiers
source                  1..5
                        mol_type = protein
                        organism = synthetic construct
REGION                  1..5
                        note = mAb2 VH CDR1
SEQUENCE: 7
WYSMT                                                                   5
```

```
SEQ ID NO: 8          moltype = AA  length = 17
FEATURE               Location/Qualifiers
source                1..17
                      mol_type = protein
                      organism = synthetic construct
REGION                1..17
                      note = mAb2 VH CDR2
SEQUENCE: 8
SIVPSGGHTQ YADSVKG                                                      17

SEQ ID NO: 9          moltype = AA  length = 9
FEATURE               Location/Qualifiers
source                1..9
                      mol_type = protein
                      organism = synthetic construct
REGION                1..9
                      note = mAb2 VH CDR3
SEQUENCE: 9
GPDWGSFDL                                                                9

SEQ ID NO: 10         moltype = AA  length = 11
FEATURE               Location/Qualifiers
source                1..11
                      mol_type = protein
                      organism = synthetic construct
REGION                1..11
                      note = mAb2 VL CDR1
SEQUENCE: 10
QASQDINNYL N                                                            11

SEQ ID NO: 11         moltype = AA  length = 7
FEATURE               Location/Qualifiers
source                1..7
                      mol_type = protein
                      organism = synthetic construct
REGION                1..7
                      note = mAb2 VL CDR2
SEQUENCE: 11
DASNLQT                                                                  7

SEQ ID NO: 12         moltype = AA  length = 9
FEATURE               Location/Qualifiers
source                1..9
                      mol_type = protein
                      organism = synthetic construct
REGION                1..9
                      note = mAb2 VL CDR3
SEQUENCE: 12
QQHEFQSPT                                                                9

SEQ ID NO: 13         moltype = AA  length = 5
FEATURE               Location/Qualifiers
source                1..5
                      mol_type = protein
                      organism = synthetic construct
REGION                1..5
                      note = mAb3 VH CDR1
SEQUENCE: 13
WYSMT                                                                    5

SEQ ID NO: 14         moltype = AA  length = 17
FEATURE               Location/Qualifiers
source                1..17
                      mol_type = protein
                      organism = synthetic construct
REGION                1..17
                      note = mAb3 VH CDR2
SEQUENCE: 14
SIVPYGDLTQ YADSVKG                                                      17

SEQ ID NO: 15         moltype = AA  length = 9
FEATURE               Location/Qualifiers
source                1..9
                      mol_type = protein
                      organism = synthetic construct
REGION                1..9
                      note = mAb3 VH CDR3
SEQUENCE: 15
GPDWGSFDL                                                                9
```

```
SEQ ID NO: 16          moltype = AA   length = 11
FEATURE                Location/Qualifiers
source                 1..11
                       mol_type = protein
                       organism = synthetic construct
REGION                 1..11
                       note = mAb3 VL CDR1
SEQUENCE: 16
QASQDINNYL N                                                          11

SEQ ID NO: 17          moltype = AA   length = 7
FEATURE                Location/Qualifiers
source                 1..7
                       mol_type = protein
                       organism = synthetic construct
REGION                 1..7
                       note = mAb3 VL CDR2
SEQUENCE: 17
DASNLQT                                                                7

SEQ ID NO: 18          moltype = AA   length = 9
FEATURE                Location/Qualifiers
source                 1..9
                       mol_type = protein
                       organism = synthetic construct
REGION                 1..9
                       note = mAb3 VL CDR3
SEQUENCE: 18
QQHESQSPT                                                              9

SEQ ID NO: 19          moltype = AA   length = 5
FEATURE                Location/Qualifiers
source                 1..5
                       mol_type = protein
                       organism = synthetic construct
REGION                 1..5
                       note = mAb4 VH CDR1
SEQUENCE: 19
WYSMT                                                                  5

SEQ ID NO: 20          moltype = AA   length = 17
FEATURE                Location/Qualifiers
source                 1..17
                       mol_type = protein
                       organism = synthetic construct
REGION                 1..17
                       note = mAb4 VH CDR2
SEQUENCE: 20
SIVPYGDLTQ YADSVKG                                                    17

SEQ ID NO: 21          moltype = AA   length = 9
FEATURE                Location/Qualifiers
source                 1..9
                       mol_type = protein
                       organism = synthetic construct
REGION                 1..9
                       note = mAb4 VH CDR3
SEQUENCE: 21
GPDWGSFDL                                                              9

SEQ ID NO: 22          moltype = AA   length = 11
FEATURE                Location/Qualifiers
source                 1..11
                       mol_type = protein
                       organism = synthetic construct
REGION                 1..11
                       note = mAb4 VL CDR1
SEQUENCE: 22
QASQDINNYL N                                                          11

SEQ ID NO: 23          moltype = AA   length = 7
FEATURE                Location/Qualifiers
source                 1..7
                       mol_type = protein
                       organism = synthetic construct
REGION                 1..7
                       note = mAb4 VL CDR2
SEQUENCE: 23
```

```
DASNLQT                                                                                  7

SEQ ID NO: 24           moltype = AA   length = 9
FEATURE                 Location/Qualifiers
source                  1..9
                        mol_type = protein
                        organism = synthetic construct
REGION                  1..9
                        note = mAb4 VL CDR3
SEQUENCE: 24
QQHEFQSPT                                                                                9

SEQ ID NO: 25           moltype = AA   length = 5
FEATURE                 Location/Qualifiers
source                  1..5
                        mol_type = protein
                        organism = synthetic construct
REGION                  1..5
                        note = mAb5 VH CDR1
SEQUENCE: 25
WYSMT                                                                                    5

SEQ ID NO: 26           moltype = AA   length = 17
FEATURE                 Location/Qualifiers
source                  1..17
                        mol_type = protein
                        organism = synthetic construct
REGION                  1..17
                        note = mAb5 VH CDR2
SEQUENCE: 26
SIVPYGDLTQ YADSVKG                                                                      17

SEQ ID NO: 27           moltype = AA   length = 9
FEATURE                 Location/Qualifiers
source                  1..9
                        mol_type = protein
                        organism = synthetic construct
REGION                  1..9
                        note = mAb5 VH CDR3
SEQUENCE: 27
GPGWGSFDL                                                                                9

SEQ ID NO: 28           moltype = AA   length = 11
FEATURE                 Location/Qualifiers
source                  1..11
                        mol_type = protein
                        organism = synthetic construct
REGION                  1..11
                        note = mAb5 VL CDR1
SEQUENCE: 28
QASQDINNYL N                                                                            11

SEQ ID NO: 29           moltype = AA   length = 7
FEATURE                 Location/Qualifiers
source                  1..7
                        mol_type = protein
                        organism = synthetic construct
REGION                  1..7
                        note = mAb5 VL CDR2
SEQUENCE: 29
DASNLQT                                                                                  7

SEQ ID NO: 30           moltype = AA   length = 9
FEATURE                 Location/Qualifiers
source                  1..9
                        mol_type = protein
                        organism = synthetic construct
REGION                  1..9
                        note = mAb5 VL CDR3
SEQUENCE: 30
QQHESQSPT                                                                                9

SEQ ID NO: 31           moltype = AA   length = 5
FEATURE                 Location/Qualifiers
source                  1..5
                        mol_type = protein
                        organism = synthetic construct
REGION                  1..5
                        note = mAb6 VH CDR1
```

```
SEQUENCE: 31
WYSMT                                                                            5

SEQ ID NO: 32         moltype = AA   length = 17
FEATURE               Location/Qualifiers
source                1..17
                      mol_type = protein
                      organism = synthetic construct
REGION                1..17
                      note = mAb6 VH CDR2
SEQUENCE: 32
SIVPYGDLTQ YADSVKG                                                               17

SEQ ID NO: 33         moltype = AA   length = 9
FEATURE               Location/Qualifiers
source                1..9
                      mol_type = protein
                      organism = synthetic construct
REGION                1..9
                      note = mAb6 VH CDR3
SEQUENCE: 33
GPGWGSFDL                                                                        9

SEQ ID NO: 34         moltype = AA   length = 11
FEATURE               Location/Qualifiers
source                1..11
                      mol_type = protein
                      organism = synthetic construct
REGION                1..11
                      note = mAb6 VL CDR1
SEQUENCE: 34
QASQDINNYL N                                                                     11

SEQ ID NO: 35         moltype = AA   length = 7
FEATURE               Location/Qualifiers
source                1..7
                      mol_type = protein
                      organism = synthetic construct
REGION                1..7
                      note = mAb6 VL CDR2
SEQUENCE: 35
DASNLQT                                                                          7

SEQ ID NO: 36         moltype = AA   length = 9
FEATURE               Location/Qualifiers
source                1..9
                      mol_type = protein
                      organism = synthetic construct
REGION                1..9
                      note = mAb6 VL CDR3
SEQUENCE: 36
QQHEFQSPT                                                                        9

SEQ ID NO: 37         moltype = AA   length = 5
FEATURE               Location/Qualifiers
source                1..5
                      mol_type = protein
                      organism = synthetic construct
REGION                1..5
                      note = mAb7 VH CDR1
SEQUENCE: 37
NYAMS                                                                            5

SEQ ID NO: 38         moltype = AA   length = 17
FEATURE               Location/Qualifiers
source                1..17
                      mol_type = protein
                      organism = synthetic construct
REGION                1..17
                      note = mAb7 VH CDR2
SEQUENCE: 38
SIVPYGDLTQ YADSVKG                                                               17

SEQ ID NO: 39         moltype = AA   length = 9
FEATURE               Location/Qualifiers
source                1..9
                      mol_type = protein
                      organism = synthetic construct
REGION                1..9
```

```
                            note = mAb7 VH CDR3
SEQUENCE: 39
GPGWGSFDL                                                                        9

SEQ ID NO: 40           moltype = AA   length = 11
FEATURE                 Location/Qualifiers
source                  1..11
                        mol_type = protein
                        organism = synthetic construct
REGION                  1..11
                        note = mAb7 VL CDR1
SEQUENCE: 40
QASQDINNYL N                                                                    11

SEQ ID NO: 41           moltype = AA   length = 7
FEATURE                 Location/Qualifiers
source                  1..7
                        mol_type = protein
                        organism = synthetic construct
REGION                  1..7
                        note = mAb7 VL CDR2
SEQUENCE: 41
DASNLQT                                                                          7

SEQ ID NO: 42           moltype = AA   length = 9
FEATURE                 Location/Qualifiers
source                  1..9
                        mol_type = protein
                        organism = synthetic construct
REGION                  1..9
                        note = mAb7 VL CDR3
SEQUENCE: 42
QQHESQSPT                                                                        9

SEQ ID NO: 43           moltype = AA   length = 5
FEATURE                 Location/Qualifiers
source                  1..5
                        mol_type = protein
                        organism = synthetic construct
REGION                  1..5
                        note = mAb8 VH CDR1
SEQUENCE: 43
SYAMS                                                                            5

SEQ ID NO: 44           moltype = AA   length = 17
FEATURE                 Location/Qualifiers
source                  1..17
                        mol_type = protein
                        organism = synthetic construct
REGION                  1..17
                        note = mAb8 VH CDR2
SEQUENCE: 44
SIVPYGDLTQ YADSVKG                                                              17

SEQ ID NO: 45           moltype = AA   length = 9
FEATURE                 Location/Qualifiers
source                  1..9
                        mol_type = protein
                        organism = synthetic construct
REGION                  1..9
                        note = mAb8 VH CDR3
SEQUENCE: 45
GPGWGSFDL                                                                        9

SEQ ID NO: 46           moltype = AA   length = 11
FEATURE                 Location/Qualifiers
source                  1..11
                        mol_type = protein
                        organism = synthetic construct
REGION                  1..11
                        note = mAb8 VL CDR1
SEQUENCE: 46
QASQDINNYL N                                                                    11

SEQ ID NO: 47           moltype = AA   length = 7
FEATURE                 Location/Qualifiers
source                  1..7
                        mol_type = protein
                        organism = synthetic construct
```

```
REGION                   1..7
                         note = mAb8 VL CDR2
SEQUENCE: 47
DASNLQT                                                              7

SEQ ID NO: 48            moltype = AA  length = 9
FEATURE                  Location/Qualifiers
source                   1..9
                         mol_type = protein
                         organism = synthetic construct
REGION                   1..9
                         note = mAb8 VL CDR3
SEQUENCE: 48
QQHESQSPT                                                            9

SEQ ID NO: 49            moltype = AA  length = 5
FEATURE                  Location/Qualifiers
source                   1..5
                         mol_type = protein
                         organism = synthetic construct
REGION                   1..5
                         note = mAb9 VH CDR1
SEQUENCE: 49
WYSMT                                                                5

SEQ ID NO: 50            moltype = AA  length = 17
FEATURE                  Location/Qualifiers
source                   1..17
                         mol_type = protein
                         organism = synthetic construct
REGION                   1..17
                         note = mAb9 VH CDR2
SEQUENCE: 50
GIVPYGDLTQ YADSVKG                                                  17

SEQ ID NO: 51            moltype = AA  length = 9
FEATURE                  Location/Qualifiers
source                   1..9
                         mol_type = protein
                         organism = synthetic construct
REGION                   1..9
                         note = mAb9 VH CDR3
SEQUENCE: 51
GPGWGSFDL                                                            9

SEQ ID NO: 52            moltype = AA  length = 11
FEATURE                  Location/Qualifiers
source                   1..11
                         mol_type = protein
                         organism = synthetic construct
REGION                   1..11
                         note = mAb9 VL CDR1
SEQUENCE: 52
QASQDINNYL N                                                        11

SEQ ID NO: 53            moltype = AA  length = 7
FEATURE                  Location/Qualifiers
source                   1..7
                         mol_type = protein
                         organism = synthetic construct
REGION                   1..7
                         note = mAb9 VL CDR2
SEQUENCE: 53
DASNLQT                                                              7

SEQ ID NO: 54            moltype = AA  length = 9
FEATURE                  Location/Qualifiers
source                   1..9
                         mol_type = protein
                         organism = synthetic construct
REGION                   1..9
                         note = mAb9 VL CDR3
SEQUENCE: 54
QQHESQSPT                                                            9

SEQ ID NO: 55            moltype = AA  length = 5
FEATURE                  Location/Qualifiers
source                   1..5
                         mol_type = protein
```

```
                         organism = synthetic construct
REGION                   1..5
                         note = mAb10 VH CDR1
SEQUENCE: 55
WYSMT                                                                   5

SEQ ID NO: 56            moltype = AA   length = 17
FEATURE                  Location/Qualifiers
source                   1..17
                         mol_type = protein
                         organism = synthetic construct
REGION                   1..17
                         note = mAb10 VH CDR2
SEQUENCE: 56
SIVAYGDLTQ YADSVKG                                                     17

SEQ ID NO: 57            moltype = AA   length = 9
FEATURE                  Location/Qualifiers
source                   1..9
                         mol_type = protein
                         organism = synthetic construct
REGION                   1..9
                         note = mAb10 VH CDR3
SEQUENCE: 57
GPGWGSFDL                                                               9

SEQ ID NO: 58            moltype = AA   length = 11
FEATURE                  Location/Qualifiers
source                   1..11
                         mol_type = protein
                         organism = synthetic construct
REGION                   1..11
                         note = mAb10 VL CDR1
SEQUENCE: 58
QASQDINNYL N                                                           11

SEQ ID NO: 59            moltype = AA   length = 7
FEATURE                  Location/Qualifiers
source                   1..7
                         mol_type = protein
                         organism = synthetic construct
REGION                   1..7
                         note = mAb10 VL CDR2
SEQUENCE: 59
DASNLQT                                                                 7

SEQ ID NO: 60            moltype = AA   length = 9
FEATURE                  Location/Qualifiers
source                   1..9
                         mol_type = protein
                         organism = synthetic construct
REGION                   1..9
                         note = mAb10 VL CDR3
SEQUENCE: 60
QQHESQSPT                                                               9

SEQ ID NO: 61            moltype = AA   length = 5
FEATURE                  Location/Qualifiers
source                   1..5
                         mol_type = protein
                         organism = synthetic construct
REGION                   1..5
                         note = mAb11 VH CDR1
SEQUENCE: 61
WYSMT                                                                   5

SEQ ID NO: 62            moltype = AA   length = 17
FEATURE                  Location/Qualifiers
source                   1..17
                         mol_type = protein
                         organism = synthetic construct
REGION                   1..17
                         note = mAb11 VH CDR2
SEQUENCE: 62
SIVDYGDLTQ YADSVKG                                                     17

SEQ ID NO: 63            moltype = AA   length = 9
FEATURE                  Location/Qualifiers
source                   1..9
```

```
                        mol_type = protein
                        organism = synthetic construct
REGION                  1..9
                        note = mAb11 VH CDR3
SEQUENCE: 63
GPGWGSFDL                                                                         9

SEQ ID NO: 64           moltype = AA  length = 11
FEATURE                 Location/Qualifiers
source                  1..11
                        mol_type = protein
                        organism = synthetic construct
REGION                  1..11
                        note = mAb11 VL CDR1
SEQUENCE: 64
QASQDINNYL N                                                                     11

SEQ ID NO: 65           moltype = AA  length = 7
FEATURE                 Location/Qualifiers
source                  1..7
                        mol_type = protein
                        organism = synthetic construct
REGION                  1..7
                        note = mAb11 VL CDR2
SEQUENCE: 65
DASNLQT                                                                           7

SEQ ID NO: 66           moltype = AA  length = 9
FEATURE                 Location/Qualifiers
source                  1..9
                        mol_type = protein
                        organism = synthetic construct
REGION                  1..9
                        note = mAb11 VL CDR3
SEQUENCE: 66
QQHESQSPT                                                                         9

SEQ ID NO: 67           moltype = AA  length = 5
FEATURE                 Location/Qualifiers
source                  1..5
                        mol_type = protein
                        organism = synthetic construct
REGION                  1..5
                        note = mAb12 VH CDR1
SEQUENCE: 67
WYSMT                                                                             5

SEQ ID NO: 68           moltype = AA  length = 17
FEATURE                 Location/Qualifiers
source                  1..17
                        mol_type = protein
                        organism = synthetic construct
REGION                  1..17
                        note = mAb12 VH CDR2
SEQUENCE: 68
SIVPYGDLTQ YADSVKG                                                               17

SEQ ID NO: 69           moltype = AA  length = 9
FEATURE                 Location/Qualifiers
source                  1..9
                        mol_type = protein
                        organism = synthetic construct
REGION                  1..9
                        note = mAb12 VH CDR3
SEQUENCE: 69
GPGWYSFDL                                                                         9

SEQ ID NO: 70           moltype = AA  length = 11
FEATURE                 Location/Qualifiers
source                  1..11
                        mol_type = protein
                        organism = synthetic construct
REGION                  1..11
                        note = mAb12 VL CDR1
SEQUENCE: 70
QASQDINNYL N                                                                     11

SEQ ID NO: 71           moltype = AA  length = 7
FEATURE                 Location/Qualifiers
```

```
source                  1..7
                        mol_type = protein
                        organism = synthetic construct
REGION                  1..7
                        note = mAb12 VL CDR2
SEQUENCE: 71
DASNLQT                                                                      7

SEQ ID NO: 72           moltype = AA   length = 9
FEATURE                 Location/Qualifiers
source                  1..9
                        mol_type = protein
                        organism = synthetic construct
REGION                  1..9
                        note = mAb12 VL CDR3
SEQUENCE: 72
QQHESQSPT                                                                    9

SEQ ID NO: 73           moltype = AA   length = 5
FEATURE                 Location/Qualifiers
source                  1..5
                        mol_type = protein
                        organism = synthetic construct
REGION                  1..5
                        note = mAb13 VH CDR1
SEQUENCE: 73
WYSMT                                                                        5

SEQ ID NO: 74           moltype = AA   length = 17
FEATURE                 Location/Qualifiers
source                  1..17
                        mol_type = protein
                        organism = synthetic construct
REGION                  1..17
                        note = mAb13 VH CDR2
SEQUENCE: 74
SIVPYGDLTQ YADSVKG                                                          17

SEQ ID NO: 75           moltype = AA   length = 9
FEATURE                 Location/Qualifiers
source                  1..9
                        mol_type = protein
                        organism = synthetic construct
REGION                  1..9
                        note = mAb13 VH CDR3
SEQUENCE: 75
PEDWGRFDL                                                                    9

SEQ ID NO: 76           moltype = AA   length = 11
FEATURE                 Location/Qualifiers
source                  1..11
                        mol_type = protein
                        organism = synthetic construct
REGION                  1..11
                        note = mAb13 VL CDR1
SEQUENCE: 76
QASQDINNYL N                                                                11

SEQ ID NO: 77           moltype = AA   length = 7
FEATURE                 Location/Qualifiers
source                  1..7
                        mol_type = protein
                        organism = synthetic construct
REGION                  1..7
                        note = mAb13 VL CDR2
SEQUENCE: 77
DASNLQT                                                                      7

SEQ ID NO: 78           moltype = AA   length = 9
FEATURE                 Location/Qualifiers
source                  1..9
                        mol_type = protein
                        organism = synthetic construct
REGION                  1..9
                        note = mAb13 VL CDR3
SEQUENCE: 78
QQHESQSPT                                                                    9

SEQ ID NO: 79           moltype = AA   length = 5
```

```
FEATURE              Location/Qualifiers
source               1..5
                     mol_type = protein
                     organism = synthetic construct
REGION               1..5
                     note = mAb14 VH CDR1
SEQUENCE: 79
WYSMT                                                                    5

SEQ ID NO: 80        moltype = AA  length = 17
FEATURE              Location/Qualifiers
source               1..17
                     mol_type = protein
                     organism = synthetic construct
REGION               1..17
                     note = mAb14 VH CDR2
SEQUENCE: 80
SIVPYGDLTQ YAESVKG                                                      17

SEQ ID NO: 81        moltype = AA  length = 9
FEATURE              Location/Qualifiers
source               1..9
                     mol_type = protein
                     organism = synthetic construct
REGION               1..9
                     note = mAb14 VH CDR3
SEQUENCE: 81
GPGWGSFDL                                                                9

SEQ ID NO: 82        moltype = AA  length = 11
FEATURE              Location/Qualifiers
source               1..11
                     mol_type = protein
                     organism = synthetic construct
REGION               1..11
                     note = mAb14 VL CDR1
SEQUENCE: 82
QASQDINNYL N                                                            11

SEQ ID NO: 83        moltype = AA  length = 7
FEATURE              Location/Qualifiers
source               1..7
                     mol_type = protein
                     organism = synthetic construct
REGION               1..7
                     note = mAb14 VL CDR2
SEQUENCE: 83
DASNLQT                                                                  7

SEQ ID NO: 84        moltype = AA  length = 9
FEATURE              Location/Qualifiers
source               1..9
                     mol_type = protein
                     organism = synthetic construct
REGION               1..9
                     note = mAb14 VL CDR3
SEQUENCE: 84
QQHESQSPT                                                                9

SEQ ID NO: 85        moltype = AA  length = 5
FEATURE              Location/Qualifiers
source               1..5
                     mol_type = protein
                     organism = synthetic construct
REGION               1..5
                     note = mAb15 VH CDR1
SEQUENCE: 85
WYSMT                                                                    5

SEQ ID NO: 86        moltype = AA  length = 17
FEATURE              Location/Qualifiers
source               1..17
                     mol_type = protein
                     organism = synthetic construct
REGION               1..17
                     note = mAb15 VH CDR2
SEQUENCE: 86
SIVPYGDLTQ YADSVKG                                                      17
```

```
SEQ ID NO: 87         moltype = AA   length = 9
FEATURE               Location/Qualifiers
source                1..9
                      mol_type = protein
                      organism = synthetic construct
REGION                1..9
                      note = mAb15 VH CDR3
SEQUENCE: 87
GPGWGSFDL                                                             9

SEQ ID NO: 88         moltype = AA   length = 11
FEATURE               Location/Qualifiers
source                1..11
                      mol_type = protein
                      organism = synthetic construct
REGION                1..11
                      note = mAb15 VL CDR1
SEQUENCE: 88
QASQDINNYL N                                                         11

SEQ ID NO: 89         moltype = AA   length = 7
FEATURE               Location/Qualifiers
source                1..7
                      mol_type = protein
                      organism = synthetic construct
REGION                1..7
                      note = mAb15 VL CDR2
SEQUENCE: 89
DASNLQT                                                               7

SEQ ID NO: 90         moltype = AA   length = 9
FEATURE               Location/Qualifiers
source                1..9
                      mol_type = protein
                      organism = synthetic construct
REGION                1..9
                      note = mAb15 VL CDR3
SEQUENCE: 90
QQHETQTPT                                                             9

SEQ ID NO: 91         moltype = AA   length = 5
FEATURE               Location/Qualifiers
source                1..5
                      mol_type = protein
                      organism = synthetic construct
REGION                1..5
                      note = mAb16 VH CDR1
SEQUENCE: 91
AYSMT                                                                 5

SEQ ID NO: 92         moltype = AA   length = 17
FEATURE               Location/Qualifiers
source                1..17
                      mol_type = protein
                      organism = synthetic construct
REGION                1..17
                      note = mAb16 VH CDR2
SEQUENCE: 92
SIVPYGDLTQ YADSVKG                                                   17

SEQ ID NO: 93         moltype = AA   length = 9
FEATURE               Location/Qualifiers
source                1..9
                      mol_type = protein
                      organism = synthetic construct
REGION                1..9
                      note = mAb16 VH CDR3
SEQUENCE: 93
GPGWGSFDL                                                             9

SEQ ID NO: 94         moltype = AA   length = 11
FEATURE               Location/Qualifiers
source                1..11
                      mol_type = protein
                      organism = synthetic construct
REGION                1..11
                      note = mAb16 VL CDR1
SEQUENCE: 94
QASQDINNYL N                                                         11
```

```
SEQ ID NO: 95              moltype = AA   length = 7
FEATURE                    Location/Qualifiers
source                     1..7
                           mol_type = protein
                           organism = synthetic construct
REGION                     1..7
                           note = mAb16 VL CDR2
SEQUENCE: 95
DASNLQT                                                                     7

SEQ ID NO: 96              moltype = AA   length = 9
FEATURE                    Location/Qualifiers
source                     1..9
                           mol_type = protein
                           organism = synthetic construct
REGION                     1..9
                           note = mAb16 VL CDR3
SEQUENCE: 96
QQHESQSPT                                                                   9

SEQ ID NO: 97              moltype = AA   length = 5
FEATURE                    Location/Qualifiers
source                     1..5
                           mol_type = protein
                           organism = synthetic construct
REGION                     1..5
                           note = mAb17 VH CDR1
SEQUENCE: 97
DYSMT                                                                       5

SEQ ID NO: 98              moltype = AA   length = 17
FEATURE                    Location/Qualifiers
source                     1..17
                           mol_type = protein
                           organism = synthetic construct
REGION                     1..17
                           note = mAb17 VH CDR2
SEQUENCE: 98
SIVPYGDLTQ YADSVKG                                                         17

SEQ ID NO: 99              moltype = AA   length = 9
FEATURE                    Location/Qualifiers
source                     1..9
                           mol_type = protein
                           organism = synthetic construct
REGION                     1..9
                           note = mAb17 VH CDR3
SEQUENCE: 99
GPGWGSFDL                                                                   9

SEQ ID NO: 100             moltype = AA   length = 11
FEATURE                    Location/Qualifiers
source                     1..11
                           mol_type = protein
                           organism = synthetic construct
REGION                     1..11
                           note = mAb17 VL CDR1
SEQUENCE: 100
QASQDINNYL N                                                               11

SEQ ID NO: 101             moltype = AA   length = 7
FEATURE                    Location/Qualifiers
source                     1..7
                           mol_type = protein
                           organism = synthetic construct
REGION                     1..7
                           note = mAb17 VL CDR2
SEQUENCE: 101
DASNLQT                                                                     7

SEQ ID NO: 102             moltype = AA   length = 9
FEATURE                    Location/Qualifiers
source                     1..9
                           mol_type = protein
                           organism = synthetic construct
REGION                     1..9
                           note = mAb17 VL CDR3
SEQUENCE: 102
```

```
QQHESQSPT                                                                        9

SEQ ID NO: 103        moltype = AA   length = 5
FEATURE               Location/Qualifiers
source                1..5
                      mol_type = protein
                      organism = synthetic construct
REGION                1..5
                      note = mAb18 VH CDR1
SEQUENCE: 103
EYSMT                                                                            5

SEQ ID NO: 104        moltype = AA   length = 17
FEATURE               Location/Qualifiers
source                1..17
                      mol_type = protein
                      organism = synthetic construct
REGION                1..17
                      note = mAb18 VH CDR2
SEQUENCE: 104
SIVPYGDLTQ YADSVKG                                                              17

SEQ ID NO: 105        moltype = AA   length = 9
FEATURE               Location/Qualifiers
source                1..9
                      mol_type = protein
                      organism = synthetic construct
REGION                1..9
                      note = mAb18 VH CDR3
SEQUENCE: 105
GPGWGSFDL                                                                        9

SEQ ID NO: 106        moltype = AA   length = 11
FEATURE               Location/Qualifiers
source                1..11
                      mol_type = protein
                      organism = synthetic construct
REGION                1..11
                      note = mAb18 VL CDR1
SEQUENCE: 106
QASQDINNYL N                                                                    11

SEQ ID NO: 107        moltype = AA   length = 7
FEATURE               Location/Qualifiers
source                1..7
                      mol_type = protein
                      organism = synthetic construct
REGION                1..7
                      note = mAb18 VL CDR2
SEQUENCE: 107
DASNLQT                                                                          7

SEQ ID NO: 108        moltype = AA   length = 9
FEATURE               Location/Qualifiers
source                1..9
                      mol_type = protein
                      organism = synthetic construct
REGION                1..9
                      note = mAb18 VL CDR3
SEQUENCE: 108
QQHESQSPT                                                                        9

SEQ ID NO: 109        moltype = AA   length = 5
FEATURE               Location/Qualifiers
source                1..5
                      mol_type = protein
                      organism = synthetic construct
REGION                1..5
                      note = mAb19 VH CDR1
SEQUENCE: 109
FYSMT                                                                            5

SEQ ID NO: 110        moltype = AA   length = 17
FEATURE               Location/Qualifiers
source                1..17
                      mol_type = protein
                      organism = synthetic construct
REGION                1..17
                      note = mAb19 VH CDR2
```

```
SEQUENCE: 110
SIVPYGDLTQ YADSVKG                                                      17

SEQ ID NO: 111           moltype = AA  length = 9
FEATURE                  Location/Qualifiers
source                   1..9
                         mol_type = protein
                         organism = synthetic construct
REGION                   1..9
                         note = mAb19 VH CDR3
SEQUENCE: 111
GPGWGSFDL                                                                9

SEQ ID NO: 112           moltype = AA  length = 11
FEATURE                  Location/Qualifiers
source                   1..11
                         mol_type = protein
                         organism = synthetic construct
REGION                   1..11
                         note = mAb19 VL CDR1
SEQUENCE: 112
QASQDINNYL N                                                            11

SEQ ID NO: 113           moltype = AA  length = 7
FEATURE                  Location/Qualifiers
source                   1..7
                         mol_type = protein
                         organism = synthetic construct
REGION                   1..7
                         note = mAb19 VL CDR2
SEQUENCE: 113
DASNLQT                                                                  7

SEQ ID NO: 114           moltype = AA  length = 9
FEATURE                  Location/Qualifiers
source                   1..9
                         mol_type = protein
                         organism = synthetic construct
REGION                   1..9
                         note = mAb19 VL CDR3
SEQUENCE: 114
QQHESQSPT                                                                9

SEQ ID NO: 115           moltype = AA  length = 5
FEATURE                  Location/Qualifiers
source                   1..5
                         mol_type = protein
                         organism = synthetic construct
REGION                   1..5
                         note = mAb20 VH CDR1
SEQUENCE: 115
GYSMT                                                                    5

SEQ ID NO: 116           moltype = AA  length = 17
FEATURE                  Location/Qualifiers
source                   1..17
                         mol_type = protein
                         organism = synthetic construct
REGION                   1..17
                         note = mAb20 VH CDR2
SEQUENCE: 116
SIVPYGDLTQ YADSVKG                                                      17

SEQ ID NO: 117           moltype = AA  length = 9
FEATURE                  Location/Qualifiers
source                   1..9
                         mol_type = protein
                         organism = synthetic construct
REGION                   1..9
                         note = mAb20 VH CDR3
SEQUENCE: 117
GPGWGSFDL                                                                9

SEQ ID NO: 118           moltype = AA  length = 11
FEATURE                  Location/Qualifiers
source                   1..11
                         mol_type = protein
                         organism = synthetic construct
REGION                   1..11
```

```
                         note = mAb20 VL CDR1
SEQUENCE: 118
QASQDINNYL N                                                    11

SEQ ID NO: 119         moltype = AA  length = 7
FEATURE                Location/Qualifiers
source                 1..7
                       mol_type = protein
                       organism = synthetic construct
REGION                 1..7
                       note = mAb20 VL CDR2
SEQUENCE: 119
DASNLQT                                                          7

SEQ ID NO: 120         moltype = AA  length = 9
FEATURE                Location/Qualifiers
source                 1..9
                       mol_type = protein
                       organism = synthetic construct
REGION                 1..9
                       note = mAb20 VL CDR3
SEQUENCE: 120
QQHESQSPT                                                        9

SEQ ID NO: 121         moltype = AA  length = 5
FEATURE                Location/Qualifiers
source                 1..5
                       mol_type = protein
                       organism = synthetic construct
REGION                 1..5
                       note = mAb21 VH CDR1
SEQUENCE: 121
HYSMT                                                            5

SEQ ID NO: 122         moltype = AA  length = 17
FEATURE                Location/Qualifiers
source                 1..17
                       mol_type = protein
                       organism = synthetic construct
REGION                 1..17
                       note = mAb21 VH CDR2
SEQUENCE: 122
SIVPYGDLTQ YADSVKG                                              17

SEQ ID NO: 123         moltype = AA  length = 9
FEATURE                Location/Qualifiers
source                 1..9
                       mol_type = protein
                       organism = synthetic construct
REGION                 1..9
                       note = mAb21 VH CDR3
SEQUENCE: 123
GPGWGSFDL                                                        9

SEQ ID NO: 124         moltype = AA  length = 11
FEATURE                Location/Qualifiers
source                 1..11
                       mol_type = protein
                       organism = synthetic construct
REGION                 1..11
                       note = mAb21 VL CDR1
SEQUENCE: 124
QASQDINNYL N                                                    11

SEQ ID NO: 125         moltype = AA  length = 7
FEATURE                Location/Qualifiers
source                 1..7
                       mol_type = protein
                       organism = synthetic construct
REGION                 1..7
                       note = mAb21 VL CDR2
SEQUENCE: 125
DASNLQT                                                          7

SEQ ID NO: 126         moltype = AA  length = 9
FEATURE                Location/Qualifiers
source                 1..9
                       mol_type = protein
                       organism = synthetic construct
```

```
REGION                        1..9
                              note = mAb21 VL CDR3
SEQUENCE: 126
QQHESQSPT                                                                        9

SEQ ID NO: 127                moltype = AA  length = 5
FEATURE                       Location/Qualifiers
source                        1..5
                              mol_type = protein
                              organism = synthetic construct
REGION                        1..5
                              note = mAb22 VH CDR1
SEQUENCE: 127
IYSMT                                                                            5

SEQ ID NO: 128                moltype = AA  length = 17
FEATURE                       Location/Qualifiers
source                        1..17
                              mol_type = protein
                              organism = synthetic construct
REGION                        1..17
                              note = mAb22 VH CDR2
SEQUENCE: 128
SIVPYGDLTQ YADSVKG                                                              17

SEQ ID NO: 129                moltype = AA  length = 9
FEATURE                       Location/Qualifiers
source                        1..9
                              mol_type = protein
                              organism = synthetic construct
REGION                        1..9
                              note = mAb22 VH CDR3
SEQUENCE: 129
GPGWGSFDL                                                                        9

SEQ ID NO: 130                moltype = AA  length = 11
FEATURE                       Location/Qualifiers
source                        1..11
                              mol_type = protein
                              organism = synthetic construct
REGION                        1..11
                              note = mAb22 VL CDR1
SEQUENCE: 130
QASQDINNYL N                                                                    11

SEQ ID NO: 131                moltype = AA  length = 7
FEATURE                       Location/Qualifiers
source                        1..7
                              mol_type = protein
                              organism = synthetic construct
REGION                        1..7
                              note = mAb22 VL CDR2
SEQUENCE: 131
DASNLQT                                                                          7

SEQ ID NO: 132                moltype = AA  length = 9
FEATURE                       Location/Qualifiers
source                        1..9
                              mol_type = protein
                              organism = synthetic construct
REGION                        1..9
                              note = mAb22 VL CDR3
SEQUENCE: 132
QQHESQSPT                                                                        9

SEQ ID NO: 133                moltype = AA  length = 5
FEATURE                       Location/Qualifiers
source                        1..5
                              mol_type = protein
                              organism = synthetic construct
REGION                        1..5
                              note = mAb23 VH CDR1
SEQUENCE: 133
KYSMT                                                                            5

SEQ ID NO: 134                moltype = AA  length = 17
FEATURE                       Location/Qualifiers
source                        1..17
                              mol_type = protein
```

```
                           organism = synthetic construct
REGION                     1..17
                           note = mAb23 VH CDR2
SEQUENCE: 134
SIVPYGDLTQ YADSVKG                                                        17

SEQ ID NO: 135             moltype = AA  length = 9
FEATURE                    Location/Qualifiers
source                     1..9
                           mol_type = protein
                           organism = synthetic construct
REGION                     1..9
                           note = mAb23 VH CDR3
SEQUENCE: 135
GPGWGSFDL                                                                  9

SEQ ID NO: 136             moltype = AA  length = 11
FEATURE                    Location/Qualifiers
source                     1..11
                           mol_type = protein
                           organism = synthetic construct
REGION                     1..11
                           note = mAb23 VL CDR1
SEQUENCE: 136
QASQDINNYL N                                                              11

SEQ ID NO: 137             moltype = AA  length = 7
FEATURE                    Location/Qualifiers
source                     1..7
                           mol_type = protein
                           organism = synthetic construct
REGION                     1..7
                           note = mAb23 VL CDR2
SEQUENCE: 137
DASNLQT                                                                    7

SEQ ID NO: 138             moltype = AA  length = 9
FEATURE                    Location/Qualifiers
source                     1..9
                           mol_type = protein
                           organism = synthetic construct
REGION                     1..9
                           note = mAb23 VL CDR3
SEQUENCE: 138
QQHESQSPT                                                                  9

SEQ ID NO: 139             moltype = AA  length = 5
FEATURE                    Location/Qualifiers
source                     1..5
                           mol_type = protein
                           organism = synthetic construct
REGION                     1..5
                           note = mAb24 VH CDR1
SEQUENCE: 139
LYSMT                                                                      5

SEQ ID NO: 140             moltype = AA  length = 17
FEATURE                    Location/Qualifiers
source                     1..17
                           mol_type = protein
                           organism = synthetic construct
REGION                     1..17
                           note = mAb24 VH CDR2
SEQUENCE: 140
SIVPYGDLTQ YADSVKG                                                        17

SEQ ID NO: 141             moltype = AA  length = 9
FEATURE                    Location/Qualifiers
source                     1..9
                           mol_type = protein
                           organism = synthetic construct
REGION                     1..9
                           note = mAb24 VH CDR3
SEQUENCE: 141
GPGWGSFDL                                                                  9

SEQ ID NO: 142             moltype = AA  length = 11
FEATURE                    Location/Qualifiers
source                     1..11
```

```
                            mol_type = protein
                            organism = synthetic construct
REGION                      1..11
                            note = mAb24 VL CDR1
SEQUENCE: 142
QASQDINNYL N                                                              11

SEQ ID NO: 143              moltype = AA  length = 7
FEATURE                     Location/Qualifiers
source                      1..7
                            mol_type = protein
                            organism = synthetic construct
REGION                      1..7
                            note = mAb24 VL CDR2
SEQUENCE: 143
DASNLQT                                                                    7

SEQ ID NO: 144              moltype = AA  length = 9
FEATURE                     Location/Qualifiers
source                      1..9
                            mol_type = protein
                            organism = synthetic construct
REGION                      1..9
                            note = mAb24 VL CDR3
SEQUENCE: 144
QQHESQSPT                                                                  9

SEQ ID NO: 145              moltype = AA  length = 5
FEATURE                     Location/Qualifiers
source                      1..5
                            mol_type = protein
                            organism = synthetic construct
REGION                      1..5
                            note = mAb25 VH CDR1
SEQUENCE: 145
MYSMT                                                                      5

SEQ ID NO: 146              moltype = AA  length = 17
FEATURE                     Location/Qualifiers
source                      1..17
                            mol_type = protein
                            organism = synthetic construct
REGION                      1..17
                            note = mAb25 VH CDR2
SEQUENCE: 146
SIVPYGDLTQ YADSVKG                                                        17

SEQ ID NO: 147              moltype = AA  length = 9
FEATURE                     Location/Qualifiers
source                      1..9
                            mol_type = protein
                            organism = synthetic construct
REGION                      1..9
                            note = mAb25 VH CDR3
SEQUENCE: 147
GPGWGSFDL                                                                  9

SEQ ID NO: 148              moltype = AA  length = 11
FEATURE                     Location/Qualifiers
source                      1..11
                            mol_type = protein
                            organism = synthetic construct
REGION                      1..11
                            note = mAb25 VL CDR1
SEQUENCE: 148
QASQDINNYL N                                                              11

SEQ ID NO: 149              moltype = AA  length = 7
FEATURE                     Location/Qualifiers
source                      1..7
                            mol_type = protein
                            organism = synthetic construct
REGION                      1..7
                            note = mAb25 VL CDR2
SEQUENCE: 149
DASNLQT                                                                    7

SEQ ID NO: 150              moltype = AA  length = 9
FEATURE                     Location/Qualifiers
```

| | | |
|---|---|---|
| | -continued | |
| source | 1..9 | |
| | mol_type = protein | |
| | organism = synthetic construct | |
| REGION | 1..9 | |
| | note = mAb25 VL CDR3 | |
| SEQUENCE: 150 | | |
| QQHESQSPT | | 9 |
| | | |
| SEQ ID NO: 151 | moltype = AA length = 5 | |
| FEATURE | Location/Qualifiers | |
| source | 1..5 | |
| | mol_type = protein | |
| | organism = synthetic construct | |
| REGION | 1..5 | |
| | note = mAb26 VH CDR1 | |
| SEQUENCE: 151 | | |
| NYSMT | | 5 |
| | | |
| SEQ ID NO: 152 | moltype = AA length = 17 | |
| FEATURE | Location/Qualifiers | |
| source | 1..17 | |
| | mol_type = protein | |
| | organism = synthetic construct | |
| REGION | 1..17 | |
| | note = mAb26 VH CDR2 | |
| SEQUENCE: 152 | | |
| SIVPYGDLTQ YADSVKG | | 17 |
| | | |
| SEQ ID NO: 153 | moltype = AA length = 9 | |
| FEATURE | Location/Qualifiers | |
| source | 1..9 | |
| | mol_type = protein | |
| | organism = synthetic construct | |
| REGION | 1..9 | |
| | note = mAb26 VH CDR3 | |
| SEQUENCE: 153 | | |
| GPGWGSFDL | | 9 |
| | | |
| SEQ ID NO: 154 | moltype = AA length = 11 | |
| FEATURE | Location/Qualifiers | |
| source | 1..11 | |
| | mol_type = protein | |
| | organism = synthetic construct | |
| REGION | 1..11 | |
| | note = mAb26 VL CDR1 | |
| SEQUENCE: 154 | | |
| QASQDINNYL N | | 11 |
| | | |
| SEQ ID NO: 155 | moltype = AA length = 7 | |
| FEATURE | Location/Qualifiers | |
| source | 1..7 | |
| | mol_type = protein | |
| | organism = synthetic construct | |
| REGION | 1..7 | |
| | note = mAb26 VL CDR2 | |
| SEQUENCE: 155 | | |
| DASNLQT | | 7 |
| | | |
| SEQ ID NO: 156 | moltype = AA length = 9 | |
| FEATURE | Location/Qualifiers | |
| source | 1..9 | |
| | mol_type = protein | |
| | organism = synthetic construct | |
| REGION | 1..9 | |
| | note = mAb26 VL CDR3 | |
| SEQUENCE: 156 | | |
| QQHESQSPT | | 9 |
| | | |
| SEQ ID NO: 157 | moltype = AA length = 5 | |
| FEATURE | Location/Qualifiers | |
| source | 1..5 | |
| | mol_type = protein | |
| | organism = synthetic construct | |
| REGION | 1..5 | |
| | note = mAb27 VH CDR1 | |
| SEQUENCE: 157 | | |
| PYSMT | | 5 |
| | | |
| SEQ ID NO: 158 | moltype = AA length = 17 | |

-continued

```
FEATURE                 Location/Qualifiers
source                  1..17
                        mol_type = protein
                        organism = synthetic construct
REGION                  1..17
                        note = mAb27 VH CDR2
SEQUENCE: 158
SIVPYGDLTQ YADSVKG                                                          17

SEQ ID NO: 159          moltype = AA  length = 9
FEATURE                 Location/Qualifiers
source                  1..9
                        mol_type = protein
                        organism = synthetic construct
REGION                  1..9
                        note = mAb27 VH CDR3
SEQUENCE: 159
GPGWGSFDL                                                                    9

SEQ ID NO: 160          moltype = AA  length = 11
FEATURE                 Location/Qualifiers
source                  1..11
                        mol_type = protein
                        organism = synthetic construct
REGION                  1..11
                        note = mAb27 VL CDR1
SEQUENCE: 160
QASQDINNYL N                                                                11

SEQ ID NO: 161          moltype = AA  length = 7
FEATURE                 Location/Qualifiers
source                  1..7
                        mol_type = protein
                        organism = synthetic construct
REGION                  1..7
                        note = mAb27 VL CDR2
SEQUENCE: 161
DASNLQT                                                                      7

SEQ ID NO: 162          moltype = AA  length = 9
FEATURE                 Location/Qualifiers
source                  1..9
                        mol_type = protein
                        organism = synthetic construct
REGION                  1..9
                        note = mAb27 VL CDR3
SEQUENCE: 162
QQHESQSPT                                                                    9

SEQ ID NO: 163          moltype = AA  length = 5
FEATURE                 Location/Qualifiers
source                  1..5
                        mol_type = protein
                        organism = synthetic construct
REGION                  1..5
                        note = mAb28 VH CDR1
SEQUENCE: 163
RYSMT                                                                        5

SEQ ID NO: 164          moltype = AA  length = 17
FEATURE                 Location/Qualifiers
source                  1..17
                        mol_type = protein
                        organism = synthetic construct
REGION                  1..17
                        note = mAb28 VH CDR2
SEQUENCE: 164
SIVPYGDLTQ YADSVKG                                                          17

SEQ ID NO: 165          moltype = AA  length = 9
FEATURE                 Location/Qualifiers
source                  1..9
                        mol_type = protein
                        organism = synthetic construct
REGION                  1..9
                        note = mAb28 VH CDR3
SEQUENCE: 165
GPGWGSFDL                                                                    9
```

```
SEQ ID NO: 166          moltype = AA   length = 11
FEATURE                 Location/Qualifiers
source                  1..11
                        mol_type = protein
                        organism = synthetic construct
REGION                  1..11
                        note = mAb28 VL CDR1
SEQUENCE: 166
QASQDINNYL N                                                              11

SEQ ID NO: 167          moltype = AA   length = 7
FEATURE                 Location/Qualifiers
source                  1..7
                        mol_type = protein
                        organism = synthetic construct
REGION                  1..7
                        note = mAb28 VL CDR2
SEQUENCE: 167
DASNLQT                                                                    7

SEQ ID NO: 168          moltype = AA   length = 9
FEATURE                 Location/Qualifiers
source                  1..9
                        mol_type = protein
                        organism = synthetic construct
REGION                  1..9
                        note = mAb28 VL CDR3
SEQUENCE: 168
QQHESQSPT                                                                  9

SEQ ID NO: 169          moltype = AA   length = 5
FEATURE                 Location/Qualifiers
source                  1..5
                        mol_type = protein
                        organism = synthetic construct
REGION                  1..5
                        note = mAb29 VH CDR1
SEQUENCE: 169
SYSMT                                                                      5

SEQ ID NO: 170          moltype = AA   length = 17
FEATURE                 Location/Qualifiers
source                  1..17
                        mol_type = protein
                        organism = synthetic construct
REGION                  1..17
                        note = mAb29 VH CDR2
SEQUENCE: 170
SIVPYGDLTQ YADSVKG                                                        17

SEQ ID NO: 171          moltype = AA   length = 9
FEATURE                 Location/Qualifiers
source                  1..9
                        mol_type = protein
                        organism = synthetic construct
REGION                  1..9
                        note = mAb29 VH CDR3
SEQUENCE: 171
GPGWGSFDL                                                                  9

SEQ ID NO: 172          moltype = AA   length = 11
FEATURE                 Location/Qualifiers
source                  1..11
                        mol_type = protein
                        organism = synthetic construct
REGION                  1..11
                        note = mAb29 VL CDR1
SEQUENCE: 172
QASQDINNYL N                                                              11

SEQ ID NO: 173          moltype = AA   length = 7
FEATURE                 Location/Qualifiers
source                  1..7
                        mol_type = protein
                        organism = synthetic construct
REGION                  1..7
                        note = mAb29 VL CDR2
SEQUENCE: 173
DASNLQT                                                                    7
```

```
SEQ ID NO: 174         moltype = AA  length = 9
FEATURE                Location/Qualifiers
source                 1..9
                       mol_type = protein
                       organism = synthetic construct
REGION                 1..9
                       note = mAb29 VL CDR3
SEQUENCE: 174
QQHESQSPT                                                              9

SEQ ID NO: 175         moltype = AA  length = 5
FEATURE                Location/Qualifiers
source                 1..5
                       mol_type = protein
                       organism = synthetic construct
REGION                 1..5
                       note = mAb30 VH CDR1
SEQUENCE: 175
TYSMT                                                                  5

SEQ ID NO: 176         moltype = AA  length = 17
FEATURE                Location/Qualifiers
source                 1..17
                       mol_type = protein
                       organism = synthetic construct
REGION                 1..17
                       note = mAb30 VH CDR2
SEQUENCE: 176
SIVPYGDLTQ YADSVKG                                                     17

SEQ ID NO: 177         moltype = AA  length = 9
FEATURE                Location/Qualifiers
source                 1..9
                       mol_type = protein
                       organism = synthetic construct
REGION                 1..9
                       note = mAb30 VH CDR3
SEQUENCE: 177
GPGWGSFDL                                                              9

SEQ ID NO: 178         moltype = AA  length = 11
FEATURE                Location/Qualifiers
source                 1..11
                       mol_type = protein
                       organism = synthetic construct
REGION                 1..11
                       note = mAb30 VL CDR1
SEQUENCE: 178
QASQDINNYL N                                                           11

SEQ ID NO: 179         moltype = AA  length = 7
FEATURE                Location/Qualifiers
source                 1..7
                       mol_type = protein
                       organism = synthetic construct
REGION                 1..7
                       note = mAb30 VL CDR2
SEQUENCE: 179
DASNLQT                                                                7

SEQ ID NO: 180         moltype = AA  length = 9
FEATURE                Location/Qualifiers
source                 1..9
                       mol_type = protein
                       organism = synthetic construct
REGION                 1..9
                       note = mAb30 VL CDR3
SEQUENCE: 180
QQHESQSPT                                                              9

SEQ ID NO: 181         moltype = AA  length = 5
FEATURE                Location/Qualifiers
source                 1..5
                       mol_type = protein
                       organism = synthetic construct
REGION                 1..5
                       note = mAb31 VH CDR1
SEQUENCE: 181
```

```
VYSMT                                                              5

SEQ ID NO: 182       moltype = AA   length = 17
FEATURE              Location/Qualifiers
source               1..17
                     mol_type = protein
                     organism = synthetic construct
REGION               1..17
                     note = mAb31 VH CDR2
SEQUENCE: 182
SIVPYGDLTQ YADSVKG                                                17

SEQ ID NO: 183       moltype = AA   length = 9
FEATURE              Location/Qualifiers
source               1..9
                     mol_type = protein
                     organism = synthetic construct
REGION               1..9
                     note = mAb31 VH CDR3
SEQUENCE: 183
GPGWGSFDL                                                          9

SEQ ID NO: 184       moltype = AA   length = 11
FEATURE              Location/Qualifiers
source               1..11
                     mol_type = protein
                     organism = synthetic construct
REGION               1..11
                     note = mAb31 VL CDR1
SEQUENCE: 184
QASQDINNYL N                                                      11

SEQ ID NO: 185       moltype = AA   length = 7
FEATURE              Location/Qualifiers
source               1..7
                     mol_type = protein
                     organism = synthetic construct
REGION               1..7
                     note = mAb31 VL CDR2
SEQUENCE: 185
DASNLQT                                                            7

SEQ ID NO: 186       moltype = AA   length = 9
FEATURE              Location/Qualifiers
source               1..9
                     mol_type = protein
                     organism = synthetic construct
REGION               1..9
                     note = mAb31 VL CDR3
SEQUENCE: 186
QQHESQSPT                                                          9

SEQ ID NO: 187       moltype = AA   length = 5
FEATURE              Location/Qualifiers
source               1..5
                     mol_type = protein
                     organism = synthetic construct
REGION               1..5
                     note = mAb32 VH CDR1
SEQUENCE: 187
YYSMT                                                              5

SEQ ID NO: 188       moltype = AA   length = 17
FEATURE              Location/Qualifiers
source               1..17
                     mol_type = protein
                     organism = synthetic construct
REGION               1..17
                     note = mAb32 VH CDR2
SEQUENCE: 188
SIVPYGDLTQ YADSVKG                                                17

SEQ ID NO: 189       moltype = AA   length = 9
FEATURE              Location/Qualifiers
source               1..9
                     mol_type = protein
                     organism = synthetic construct
REGION               1..9
                     note = mAb32 VH CDR3
```

-continued

```
SEQUENCE: 189
GPGWGSFDL                                                                                    9

SEQ ID NO: 190          moltype = AA  length = 10
FEATURE                 Location/Qualifiers
source                  1..10
                        mol_type = protein
                        organism = synthetic construct
REGION                  1..10
                        note = mAb32 VL CDR1
SEQUENCE: 190
QASQDINNYL                                                                                  10

SEQ ID NO: 191          moltype = AA  length = 7
FEATURE                 Location/Qualifiers
source                  1..7
                        mol_type = protein
                        organism = synthetic construct
REGION                  1..7
                        note = mAb32 VL CDR2
SEQUENCE: 191
DASNLQT                                                                                      7

SEQ ID NO: 192          moltype = AA  length = 9
FEATURE                 Location/Qualifiers
source                  1..9
                        mol_type = protein
                        organism = synthetic construct
REGION                  1..9
                        note = mAb32 VL CDR3
SEQUENCE: 192
QQHESQSPT                                                                                    9

SEQ ID NO: 193          moltype = AA  length = 118
FEATURE                 Location/Qualifiers
source                  1..118
                        mol_type = protein
                        organism = synthetic construct
REGION                  1..118
                        note = mAb1 VH Chain
SEQUENCE: 193
EVQLLESGGG LVQPGGSLRL SCAASGFTFS WYSMTWVRQA PGKGLEWVSS IVPSGGHTQY             60
ADSVKGRFTI SRDNSKNTLY LQMNSLRAED TAVYYCAKGP DWGSFDLWGR GTLVTVSS             118

SEQ ID NO: 194          moltype = AA  length = 107
FEATURE                 Location/Qualifiers
source                  1..107
                        mol_type = protein
                        organism = synthetic construct
REGION                  1..107
                        note = mAb1 VL Chain
SEQUENCE: 194
DIQMTQSPSS LSASVGDRVT ITCQASQDIN NYLNWYQQKP GKAPKLLIYD ASNLQTGVPS             60
RFSGSGSGTD FTFTISSLQP EDIATYYCQQ HESQSPTFGP GTKVDIK                         107

SEQ ID NO: 195          moltype = AA  length = 118
FEATURE                 Location/Qualifiers
source                  1..118
                        mol_type = protein
                        organism = synthetic construct
REGION                  1..118
                        note = mAb2 VH Chain
SEQUENCE: 195
EVQLLESGGG LVQPGGSLRL SCAASGFTFS WYSMTWVRQA PGKGLEWVSS IVPSGGHTQY             60
ADSVKGRFTI SRDNSKNTLY LQMNSLRAED TAVYYCAKGP DWGSFDLWGR GTLVTVSS             118

SEQ ID NO: 196          moltype = AA  length = 107
FEATURE                 Location/Qualifiers
source                  1..107
                        mol_type = protein
                        organism = synthetic construct
REGION                  1..107
                        note = mAb2 VL Chain
SEQUENCE: 196
DIQMTQSPSS LSASVGDRVT ITCQASQDIN NYLNWYQQKP GKAPKLLIYD ASNLQTGVPS             60
RFSGSGSGTD FTFTISSLQP EDIATYYCQQ HEFQSPTFGP GTKVDIK                         107

SEQ ID NO: 197          moltype = AA  length = 118
FEATURE                 Location/Qualifiers
```

```
source                  1..118
                        mol_type = protein
                        organism = synthetic construct
REGION                  1..118
                        note = mAb3 VH Chain
SEQUENCE: 197
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKGP DWGSFDLWGR GTLVTVSS    118

SEQ ID NO: 198          moltype = AA  length = 107
FEATURE                 Location/Qualifiers
source                  1..107
                        mol_type = protein
                        organism = synthetic construct
REGION                  1..107
                        note = mAb3 VL Chain
SEQUENCE: 198
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 199          moltype = AA  length = 118
FEATURE                 Location/Qualifiers
source                  1..118
                        mol_type = protein
                        organism = synthetic construct
REGION                  1..118
                        note = mAb4 VH Chain
SEQUENCE: 199
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKGP DWGSFDLWGR GTLVTVSS    118

SEQ ID NO: 200          moltype = AA  length = 107
FEATURE                 Location/Qualifiers
source                  1..107
                        mol_type = protein
                        organism = synthetic construct
REGION                  1..107
                        note = mAb4 VL Chain
SEQUENCE: 200
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HEFQSPTFGP GTKVDIK                107

SEQ ID NO: 201          moltype = AA  length = 118
FEATURE                 Location/Qualifiers
source                  1..118
                        mol_type = protein
                        organism = synthetic construct
REGION                  1..118
                        note = mAb5 VH Chain
SEQUENCE: 201
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 202          moltype = AA  length = 107
FEATURE                 Location/Qualifiers
source                  1..107
                        mol_type = protein
                        organism = synthetic construct
REGION                  1..107
                        note = mAb5 VL Chain
SEQUENCE: 202
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 203          moltype = AA  length = 118
FEATURE                 Location/Qualifiers
source                  1..118
                        mol_type = protein
                        organism = synthetic construct
REGION                  1..118
                        note = mAb6 VH Chain
SEQUENCE: 203
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 204          moltype = AA  length = 107
FEATURE                 Location/Qualifiers
source                  1..107
                        mol_type = protein
```

```
                              organism = synthetic construct
REGION                        1..107
                              note = mAb6 VL Chain
SEQUENCE: 204
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HEFQSPTFGP GTKVDIK                 107

SEQ ID NO: 205                moltype = AA  length = 118
FEATURE                       Location/Qualifiers
source                        1..118
                              mol_type = protein
                              organism = synthetic construct
REGION                        1..118
                              note = mAb7 VH Chain
SEQUENCE: 205
EVQLLESGGG LVQPGGSLRL SCAASGFTFS NYAMSWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 206                moltype = AA  length = 107
FEATURE                       Location/Qualifiers
source                        1..107
                              mol_type = protein
                              organism = synthetic construct
REGION                        1..107
                              note = mAb7 VL Chain
SEQUENCE: 206
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 207                moltype = AA  length = 118
FEATURE                       Location/Qualifiers
source                        1..118
                              mol_type = protein
                              organism = synthetic construct
REGION                        1..118
                              note = mAb8 VH Chain
SEQUENCE: 207
EVQLLESGGG LVQPGGSLRL SCAASGFTFS SYAMSWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 208                moltype = AA  length = 107
FEATURE                       Location/Qualifiers
source                        1..107
                              mol_type = protein
                              organism = synthetic construct
REGION                        1..107
                              note = mAb8 VL Chain
SEQUENCE: 208
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 209                moltype = AA  length = 118
FEATURE                       Location/Qualifiers
source                        1..118
                              mol_type = protein
                              organism = synthetic construct
REGION                        1..118
                              note = mAb9 VH Chain
SEQUENCE: 209
EVQLLESGGG LVQPGGSLRL SCAASGFTFS WYSMTWVRQA PGKGLEWVSG IVPYGDLTQY    60
ADSVKGRFTI SRDNSKNTLY LQMNSLRAED TAVYYCAKGP GWGSFDLWGR GTLVTVSS    118

SEQ ID NO: 210                moltype = AA  length = 107
FEATURE                       Location/Qualifiers
source                        1..107
                              mol_type = protein
                              organism = synthetic construct
REGION                        1..107
                              note = mAb9 VL Chain
SEQUENCE: 210
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 211                moltype = AA  length = 118
FEATURE                       Location/Qualifiers
source                        1..118
                              mol_type = protein
                              organism = synthetic construct
REGION                        1..118
```

```
                          note = mAb10 VH Chain
SEQUENCE: 211
EVQLLESGGG LVQPGGSLRL SCAASGFTFS WYSMTWVRQA PGKGLEWVSS IVAYGDLTQY    60
ADSVKGRFTI SRDNSKNTLY LQMNSLRAED TAVYYCAKGP GWGSFDLWGR GTLVTVSS    118

SEQ ID NO: 212            moltype = AA  length = 107
FEATURE                   Location/Qualifiers
source                    1..107
                          mol_type = protein
                          organism = synthetic construct
REGION                    1..107
                          note = mAb10 VL Chain
SEQUENCE: 212
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 213            moltype = AA  length = 118
FEATURE                   Location/Qualifiers
source                    1..118
                          mol_type = protein
                          organism = synthetic construct
REGION                    1..118
                          note = mAb11 VH Chain
SEQUENCE: 213
EVQLLESGGG LVQPGGSLRL SCAASGFTFS WYSMTWVRQA PGKGLEWVSS IVDYGDLTQY    60
ADSVKGRFTI SRDNSKNTLY LQMNSLRAED TAVYYCAKGP GWGSFDLWGR GTLVTVSS    118

SEQ ID NO: 214            moltype = AA  length = 107
FEATURE                   Location/Qualifiers
source                    1..107
                          mol_type = protein
                          organism = synthetic construct
REGION                    1..107
                          note = mAb11 VL Chain
SEQUENCE: 214
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 215            moltype = AA  length = 118
FEATURE                   Location/Qualifiers
source                    1..118
                          mol_type = protein
                          organism = synthetic construct
REGION                    1..118
                          note = mAb12 VH Chain
SEQUENCE: 215
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKGP GWYSFDLWGR GTLVTVSS    118

SEQ ID NO: 216            moltype = AA  length = 107
FEATURE                   Location/Qualifiers
source                    1..107
                          mol_type = protein
                          organism = synthetic construct
REGION                    1..107
                          note = mAb12 VL Chain
SEQUENCE: 216
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 217            moltype = AA  length = 118
FEATURE                   Location/Qualifiers
source                    1..118
                          mol_type = protein
                          organism = synthetic construct
REGION                    1..118
                          note = mAb13 VH Chain
SEQUENCE: 217
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKPE DWGRFDLWGR GTLVTVSS    118

SEQ ID NO: 218            moltype = AA  length = 107
FEATURE                   Location/Qualifiers
source                    1..107
                          mol_type = protein
                          organism = synthetic construct
REGION                    1..107
                          note = mAb13 VL Chain
SEQUENCE: 218
```

```
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 219          moltype = AA   length = 118
FEATURE                 Location/Qualifiers
source                  1..118
                        mol_type = protein
                        organism = synthetic construct
REGION                  1..118
                        note = mAb14 VH Chain
SEQUENCE: 219
EVQLLESGGG LVQPGGSLRL SCAASGFTFS WYSMTWVRQA PGKGLEWVSS IVPYGDLTQY    60
AESVKGRFTI SRDNSKNTLY LQMNSLRAED TAVYYCAKGP GWGSFDLWGR GTLVTVSS     118

SEQ ID NO: 220          moltype = AA   length = 107
FEATURE                 Location/Qualifiers
source                  1..107
                        mol_type = protein
                        organism = synthetic construct
REGION                  1..107
                        note = mAb14 VL Chain
SEQUENCE: 220
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 221          moltype = AA   length = 118
FEATURE                 Location/Qualifiers
source                  1..118
                        mol_type = protein
                        organism = synthetic construct
REGION                  1..118
                        note = mAb15 VH Chain
SEQUENCE: 221
EVQLLESGGG LVQPGGSLRL SCAASGFTFS WYSMTWVRQA PGKGLEWVSS IVPYGDLTQY    60
ADSVKGRFTI SRDNSKNTLY LQMNSLRAED TAVYYCAKGP GWGSFDLWGR GTLVTVSS     118

SEQ ID NO: 222          moltype = AA   length = 107
FEATURE                 Location/Qualifiers
source                  1..107
                        mol_type = protein
                        organism = synthetic construct
REGION                  1..107
                        note = mAb15 VL Chain
SEQUENCE: 222
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HETQTPTFGP GTKVDIK                 107

SEQ ID NO: 223          moltype = AA   length = 118
FEATURE                 Location/Qualifiers
source                  1..118
                        mol_type = protein
                        organism = synthetic construct
REGION                  1..118
                        note = mAb16 VH Chain
SEQUENCE: 223
EVQLLESGGG LVQPGGSLRL SCAASGFTFS AYSMTWVRQA PGKGLEWVSS IVPYGDLTQY    60
ADSVKGRFTI SRDNSKNTLY LQMNSLRAED TAVYYCAKGP GWGSFDLWGR GTLVTVSS     118

SEQ ID NO: 224          moltype = AA   length = 107
FEATURE                 Location/Qualifiers
source                  1..107
                        mol_type = protein
                        organism = synthetic construct
REGION                  1..107
                        note = mAb16 VL Chain
SEQUENCE: 224
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 225          moltype = AA   length = 118
FEATURE                 Location/Qualifiers
source                  1..118
                        mol_type = protein
                        organism = synthetic construct
REGION                  1..118
                        note = mAb17 VH Chain
SEQUENCE: 225
EVQLLESGGG LVQPGGSLRL SCAASGFTFS DYSMTWVRQA PGKGLEWVSS IVPYGDLTQY    60
ADSVKGRFTI SRDNSKNTLY LQMNSLRAED TAVYYCAKGP GWGSFDLWGR GTLVTVSS     118
```

```
SEQ ID NO: 226          moltype = AA  length = 107
FEATURE                 Location/Qualifiers
source                  1..107
                        mol_type = protein
                        organism = synthetic construct
REGION                  1..107
                        note = mAb17 VL Chain
SEQUENCE: 226
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 227          moltype = AA  length = 118
FEATURE                 Location/Qualifiers
source                  1..118
                        mol_type = protein
                        organism = synthetic construct
REGION                  1..118
                        note = mAb18 VH Chain
SEQUENCE: 227
EVQLLESGGG LVQPGGSLRL SCAASGFTFS EYSMTWVRQA PGKGLEWVSS IVPYGDLTQY    60
ADSVKGRFTI SRDNSKNTLY LQMNSLRAED TAVYYCAKGP GWGSFDLWGR GTLVTVSS     118

SEQ ID NO: 228          moltype = AA  length = 107
FEATURE                 Location/Qualifiers
source                  1..107
                        mol_type = protein
                        organism = synthetic construct
REGION                  1..107
                        note = mAb18 VL Chain
SEQUENCE: 228
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 229          moltype = AA  length = 118
FEATURE                 Location/Qualifiers
source                  1..118
                        mol_type = protein
                        organism = synthetic construct
REGION                  1..118
                        note = mAb19 VH Chain
SEQUENCE: 229
EVQLLESGGG LVQPGGSLRL SCAASGFTFS FYSMTWVRQA PGKGLEWVSS IVPYGDLTQY    60
ADSVKGRFTI SRDNSKNTLY LQMNSLRAED TAVYYCAKGP GWGSFDLWGR GTLVTVSS     118

SEQ ID NO: 230          moltype = AA  length = 107
FEATURE                 Location/Qualifiers
source                  1..107
                        mol_type = protein
                        organism = synthetic construct
REGION                  1..107
                        note = mAb19 VL Chain
SEQUENCE: 230
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 231          moltype = AA  length = 118
FEATURE                 Location/Qualifiers
source                  1..118
                        mol_type = protein
                        organism = synthetic construct
REGION                  1..118
                        note = mAb20 VH Chain
SEQUENCE: 231
EVQLLESGGG LVQPGGSLRL SCAASGFTFS GYSMTWVRQA PGKGLEWVSS IVPYGDLTQY    60
ADSVKGRFTI SRDNSKNTLY LQMNSLRAED TAVYYCAKGP GWGSFDLWGR GTLVTVSS     118

SEQ ID NO: 232          moltype = AA  length = 107
FEATURE                 Location/Qualifiers
source                  1..107
                        mol_type = protein
                        organism = synthetic construct
REGION                  1..107
                        note = mAb20 VL Chain
SEQUENCE: 232
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 233          moltype = AA  length = 118
```

```
FEATURE                 Location/Qualifiers
source                  1..118
                        mol_type = protein
                        organism = synthetic construct
REGION                  1..118
                        note = mAb21 VH Chain
SEQUENCE: 233
EVQLLESGGG LVQPGGSLRL SCAASGFTFS HYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 234          moltype = AA  length = 107
FEATURE                 Location/Qualifiers
source                  1..107
                        mol_type = protein
                        organism = synthetic construct
REGION                  1..107
                        note = mAb21 VL Chain
SEQUENCE: 234
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 235          moltype = AA  length = 118
FEATURE                 Location/Qualifiers
source                  1..118
                        mol_type = protein
                        organism = synthetic construct
REGION                  1..118
                        note = mAb22 VH Chain
SEQUENCE: 235
EVQLLESGGG LVQPGGSLRL SCAASGFTFS IYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 236          moltype = AA  length = 107
FEATURE                 Location/Qualifiers
source                  1..107
                        mol_type = protein
                        organism = synthetic construct
REGION                  1..107
                        note = mAb22 VL Chain
SEQUENCE: 236
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 237          moltype = AA  length = 118
FEATURE                 Location/Qualifiers
source                  1..118
                        mol_type = protein
                        organism = synthetic construct
REGION                  1..118
                        note = mAb23 VH Chain
SEQUENCE: 237
EVQLLESGGG LVQPGGSLRL SCAASGFTFS KYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 238          moltype = AA  length = 107
FEATURE                 Location/Qualifiers
source                  1..107
                        mol_type = protein
                        organism = synthetic construct
REGION                  1..107
                        note = mAb23 VL Chain
SEQUENCE: 238
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 239          moltype = AA  length = 118
FEATURE                 Location/Qualifiers
source                  1..118
                        mol_type = protein
                        organism = synthetic construct
REGION                  1..118
                        note = mAb24 VH Chain
SEQUENCE: 239
EVQLLESGGG LVQPGGSLRL SCAASGFTFS LYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 240          moltype = AA  length = 107
FEATURE                 Location/Qualifiers
source                  1..107
```

```
                        mol_type = protein
                        organism = synthetic construct
REGION                  1..107
                        note = mAb24 VL Chain
SEQUENCE: 240
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 241          moltype = AA  length = 118
FEATURE                 Location/Qualifiers
source                  1..118
                        mol_type = protein
                        organism = synthetic construct
REGION                  1..118
                        note = mAb25 VH Chain
SEQUENCE: 241
EVQLLESGGG LVQPGGSLRL SCAASGFTFS MYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 242          moltype = AA  length = 107
FEATURE                 Location/Qualifiers
source                  1..107
                        mol_type = protein
                        organism = synthetic construct
REGION                  1..107
                        note = mAb25 VL Chain
SEQUENCE: 242
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 243          moltype = AA  length = 118
FEATURE                 Location/Qualifiers
source                  1..118
                        mol_type = protein
                        organism = synthetic construct
REGION                  1..118
                        note = mAb23 VH Chain
SEQUENCE: 243
EVQLLESGGG LVQPGGSLRL SCAASGFTFS NYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 244          moltype = AA  length = 107
FEATURE                 Location/Qualifiers
source                  1..107
                        mol_type = protein
                        organism = synthetic construct
REGION                  1..107
                        note = mAb26 VL Chaim
SEQUENCE: 244
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 245          moltype = AA  length = 118
FEATURE                 Location/Qualifiers
source                  1..118
                        mol_type = protein
                        organism = synthetic construct
REGION                  1..118
                        note = mAb27 VH Chain
SEQUENCE: 245
EVQLLESGGG LVQPGGSLRL SCAASGFTFS PYSMTWVRQA PGKGLEWVSS IVPYGDLTQY    60
ADSVKGRFTI SRDNSKNTLY LQMNSLRAED TAVYYCAKGP GWGSFDLWGR GTLVTVSS    118

SEQ ID NO: 246          moltype = AA  length = 107
FEATURE                 Location/Qualifiers
source                  1..107
                        mol_type = protein
                        organism = synthetic construct
REGION                  1..107
                        note = mAb27 VL Chain
SEQUENCE: 246
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                 107

SEQ ID NO: 247          moltype = AA  length = 118
FEATURE                 Location/Qualifiers
source                  1..118
                        mol_type = protein
                        organism = synthetic construct
```

```
REGION                        1..118
                              note = mAb28 VH Chain
SEQUENCE: 247
EVQLLESGGG LVQPGGSLRL SCAASGFTFS RYSMTWVRQA PGKGLEWVSS IVPYGDLTQY   60
ADSVKGRFTI SRDNSKNTLY LQMNSLRAED TAVYYCAKGP GWGSFDLWGR GTLVTVSS    118

SEQ ID NO: 248                moltype = AA  length = 107
FEATURE                       Location/Qualifiers
source                        1..107
                              mol_type = protein
                              organism = synthetic construct
REGION                        1..107
                              note = mAb28 VL Chain
SEQUENCE: 248
DIQMTQSPSS LSASVGDRVT ITCQASQDIN NYLNWYQQKP GKAPKLLIYD ASNLQTGVPS   60
RFSGSGSGTD FTFTISSLQP EDIATYYCQQ HESQSPTFGP GTKVDIK                107

SEQ ID NO: 249                moltype = AA  length = 118
FEATURE                       Location/Qualifiers
source                        1..118
                              mol_type = protein
                              organism = synthetic construct
REGION                        1..118
                              note = mAb29 VH Chain
SEQUENCE: 249
EVQLLESGGG LVQPGGSLRL SCAASGFTFS SYSMTWVRQA PGKGLEWVSS IVPYGDLTQY   60
ADSVKGRFTI SRDNSKNTLY LQMNSLRAED TAVYYCAKGP GWGSFDLWGR GTLVTVSS    118

SEQ ID NO: 250                moltype = AA  length = 107
FEATURE                       Location/Qualifiers
source                        1..107
                              mol_type = protein
                              organism = synthetic construct
REGION                        1..107
                              note = mAb29 VL Chain
SEQUENCE: 250
DIQMTQSPSS LSASVGDRVT ITCQASQDIN NYLNWYQQKP GKAPKLLIYD ASNLQTGVPS   60
RFSGSGSGTD FTFTISSLQP EDIATYYCQQ HESQSPTFGP GTKVDIK                107

SEQ ID NO: 251                moltype = AA  length = 118
FEATURE                       Location/Qualifiers
source                        1..118
                              mol_type = protein
                              organism = synthetic construct
REGION                        1..118
                              note = mAb30 VH Chain
SEQUENCE: 251
EVQLLESGGG LVQPGGSLRL SCAASGFTFS TYSMTWVRQA PGKGLEWVSS IVPYGDLTQY   60
ADSVKGRFTI SRDNSKNTLY LQMNSLRAED TAVYYCAKGP GWGSFDLWGR GTLVTVSS    118

SEQ ID NO: 252                moltype = AA  length = 107
FEATURE                       Location/Qualifiers
source                        1..107
                              mol_type = protein
                              organism = synthetic construct
REGION                        1..107
                              note = mAb30 VL Chain
SEQUENCE: 252
DIQMTQSPSS LSASVGDRVT ITCQASQDIN NYLNWYQQKP GKAPKLLIYD ASNLQTGVPS   60
RFSGSGSGTD FTFTISSLQP EDIATYYCQQ HESQSPTFGP GTKVDIK                107

SEQ ID NO: 253                moltype = AA  length = 118
FEATURE                       Location/Qualifiers
source                        1..118
                              mol_type = protein
                              organism = synthetic construct
REGION                        1..118
                              note = mAb31 VH Chain
SEQUENCE: 253
EVQLLESGGG LVQPGGSLRL SCAASGFTFS VYSMTWVRQA PGKGLEWVSS IVPYGDLTQY   60
ADSVKGRFTI SRDNSKNTLY LQMNSLRAED TAVYYCAKGP GWGSFDLWGR GTLVTVSS    118

SEQ ID NO: 254                moltype = AA  length = 107
FEATURE                       Location/Qualifiers
source                        1..107
                              mol_type = protein
                              organism = synthetic construct
REGION                        1..107
                              note = mAb31 VL Chain
```

```
SEQUENCE: 254
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 255              moltype = AA  length = 118
FEATURE                     Location/Qualifiers
source                      1..118
                            mol_type = protein
                            organism = synthetic construct
REGION                      1..118
                            note = mAb32 VH Chain
SEQUENCE: 255
EVQLLESGGG LVQPGGSLRL SCAASGFTFS YYSMTWVRQA PGKGLEWVSS IVPYGDLTQY    60
ADSVKGRFTI SRDNSKNTLY LQMNSLRAED TAVYYCAKGG GWGSFDLWGR GTLVTVSS    118

SEQ ID NO: 256              moltype = AA  length = 107
FEATURE                     Location/Qualifiers
source                      1..107
                            mol_type = protein
                            organism = synthetic construct
REGION                      1..107
                            note = mAb32 VL Chain
SEQUENCE: 256
DIQMTQSPSS LSASVGDRVT ITCQASQDIN NYLNWYQQKP GKAPKLLIYD ASNLQTGVPS    60
RFSGSGSGTD FTFTISSLQP EDIATYYCQQ HESQSPTFGP GTKVDIK                107

SEQ ID NO: 257              moltype = AA  length = 422
FEATURE                     Location/Qualifiers
source                      1..422
                            mol_type = protein
                            organism = Homo sapiens
SEQUENCE: 257
MSSSCSGLSR VLVAVATALV SASSPCPQAW GPPGVQYGQP GRSVKLCCPG VTAGDPVSWF    60
RDGEPKLLQG PDSGLGHELV LAQADSTDEG TYICQTLDGA LGGTVTLQLG YPPARPVVSC   120
QAADYENFSC TWSPSQISGL PTRYLTSYRK KTVLGADSQR RSPSTGPWPC PQDPLGAARC   180
VVHGAEFWSQ YRINVTEVNP LGASTRLLDV SLQSILRPDP PQGLRVESVP GYPRRLRASW   240
TYPASWPCQP HFLLKFRLQY RPAQHPAWST VEPAGLEEVI TDAVAGLPHA VRVSARDFLD   300
AGTWSTWSPE AWGTPSTGTI PKEIPAWGQL HTQPEVEPQV DSPAPPRPSL QPHPRLLDHR   360
DSVEQVAVLA SLGILSFLGL VAGALALGLW LRLRRGGKDG SPKPGFLASV IPVDRRPGAP   420
NL                                                                 422

SEQ ID NO: 258              moltype = AA  length = 327
FEATURE                     Location/Qualifiers
source                      1..327
                            mol_type = protein
                            organism = Homo sapiens
SEQUENCE: 258
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 259              moltype = AA  length = 327
FEATURE                     Location/Qualifiers
source                      1..327
                            mol_type = protein
                            organism = synthetic construct
REGION                      1..327
                            note = Variant IgG4
SEQUENCE: 259
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327
```